(12) United States Patent
Nabhan et al.

(10) Patent No.: US 12,139,517 B2
(45) Date of Patent: *Nov. 12, 2024

(54) MODULATORS OF CHROMOSOME 9 OPEN READING FRAME 72 GENE EXPRESSION AND USES THEREOF

(71) Applicant: Sangamo Therapeutics, Inc., Brisbane, CA (US)

(72) Inventors: Joseph F. Nabhan, Arlington, MA (US); Amrutha Pattamatta, Watertown, MA (US); Mohammad Samie, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 16/856,774

(22) Filed: Apr. 23, 2020

(65) Prior Publication Data

US 2020/0339638 A1    Oct. 29, 2020

Related U.S. Application Data

(60) Provisional application No. 62/964,844, filed on Jan. 23, 2020, provisional application No. 62/837,523, filed on Apr. 23, 2019.

(51) Int. Cl.
*C07K 14/435*   (2006.01)
*A61P 25/00*    (2006.01)
(Continued)

(52) U.S. Cl.
CPC ............ *C07K 14/435* (2013.01); *A61P 25/00* (2018.01); *A61P 25/28* (2018.01); *C12N 15/86* (2013.01); *A61K 38/00* (2013.01); *A61K 48/00* (2013.01); *C07K 2319/81* (2013.01); *C12N 2750/14132* (2013.01); *C12N 2750/14143* (2013.01)

(58) Field of Classification Search
None
See application file for complete search history.

(56) References Cited

U.S. PATENT DOCUMENTS 5,420,032 A   5/1995   Marshall et al.
5,789,538 A   8/1998   Rebar et al.
(Continued)

FOREIGN PATENT DOCUMENTS

CN    109312339 A    2/2019
EP    2727600 B1    3/2019
(Continued)

OTHER PUBLICATIONS

Alisky, et al., "Gene Therapy for Amyotrophic Lateral Sclerosis and Other Motor Neuron Diseases," Hum. Gene Ther. (2000) 11:2315-29.
(Continued)

*Primary Examiner* — Aurora M Fontainhas
(74) *Attorney, Agent, or Firm* — ROTHWELL, FIGG, ERNST & MANBECK, P.C.

(57) ABSTRACT

The present disclosure provides compositions and methods for modulating transcription of mutant C9orf72 gene alleles in patients in need thereof, including patients having a C9orf72-related disease such as amyotrophic lateral sclerosis (ALS) or frontotemporal dementia (FTD).

21 Claims, 18 Drawing Sheets

Specification includes a Sequence Listing.

(51) Int. Cl.
*A61P 25/28* (2006.01)
*C12N 15/86* (2006.01)
*A61K 38/00* (2006.01)
*A61K 48/00* (2006.01)

(56) References Cited

U.S. PATENT DOCUMENTS

| | | | |
|---|---|---|---|
| 5,925,523 | A | 7/1999 | Dove et al. |
| 6,007,988 | A | 12/1999 | Choo et al. |
| 6,008,336 | A | 12/1999 | Hanson et al. |
| 6,013,453 | A | 1/2000 | Choo et al. |
| 6,140,081 | A | 10/2000 | Barbas |
| 6,200,759 | B1 | 3/2001 | Dove et al. |
| 6,309,634 | B1 | 10/2001 | Bankiewicz et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,746,838 | B1 | 6/2004 | Choo et al. |
| 6,824,978 | B1 | 11/2004 | Cox, III et al. |
| 6,833,252 | B1 | 12/2004 | Dujon et al. |
| 6,866,997 | B1 | 3/2005 | Choo et al. |
| 6,903,185 | B2 | 6/2005 | Kim et al. |
| 6,933,113 | B2 | 8/2005 | Case et al. |
| 6,953,575 | B2 | 10/2005 | Bankiewicz et al. |
| 6,979,539 | B2 | 12/2005 | Cox, III et al. |
| 7,013,219 | B2 | 3/2006 | Case et al. |
| 7,053,264 | B2 | 5/2006 | Wolffe |
| 7,074,596 | B2 | 7/2006 | Darzynkiewicz et al. |
| 7,153,949 | B2 | 12/2006 | Kim et al. |
| 7,163,824 | B2 | 1/2007 | Cox, III et al. |
| 7,182,944 | B2 | 2/2007 | Bankiewicz |
| 7,198,951 | B2 | 4/2007 | Gao et al. |
| 7,241,573 | B2 | 7/2007 | Choo et al. |
| 7,241,574 | B2 | 7/2007 | Choo et al. |
| 7,837,668 | B2 | 11/2010 | Gasmi et al. |
| 7,888,121 | B2 | 2/2011 | Urnov et al. |
| 7,914,796 | B2 | 3/2011 | Miller et al. |
| 8,034,598 | B2 | 10/2011 | Miller |
| 8,092,429 | B2 | 1/2012 | Gasmi et al. |
| 8,153,773 | B2 | 4/2012 | Jemielity et al. |
| 8,309,355 | B2 | 11/2012 | Bankiewicz et al. |
| 8,337,458 | B2 | 12/2012 | Bankiewicz et al. |
| 8,409,861 | B2 | 4/2013 | Guschin et al. |
| 8,586,526 | B2 | 11/2013 | Gregory et al. |
| 8,597,912 | B2 | 12/2013 | Collingwood et al. |
| 8,623,618 | B2 | 1/2014 | Doyon et al. |
| 8,703,489 | B2 | 4/2014 | Wang |
| 8,772,453 | B2 | 7/2014 | Paschon et al. |
| 8,841,260 | B2 | 9/2014 | Miller et al. |
| 8,956,828 | B2 | 2/2015 | Bonini et al. |
| 9,050,299 | B2 | 6/2015 | Bankiewicz |
| 9,089,667 | B2 | 7/2015 | Bankiewicz |
| 9,163,245 | B2 | 10/2015 | Paschon et al. |
| 9,200,266 | B2 | 12/2015 | Wang |
| 9,234,016 | B2 | 1/2016 | Gregory et al. |
| 9,458,205 | B2 | 10/2016 | Gregory et al. |
| 9,585,971 | B2 | 3/2017 | Deverman et al. |
| 9,624,498 | B2 | 4/2017 | Froelich et al. |
| 2002/0081614 | A1 | 6/2002 | Case et al. |
| 2005/0235369 | A1* | 10/2005 | Choo ............... A01K 67/0275 800/14 |
| 2006/0239966 | A1 | 10/2006 | Tornoe et al. |
| 2007/0117128 | A1 | 5/2007 | Smith et al. |
| 2009/0068164 | A1 | 3/2009 | Segal et al. |
| 2009/0111119 | A1 | 4/2009 | Doyon et al. |
| 2009/0215878 | A1 | 8/2009 | Tan et al. |
| 2011/0082093 | A1 | 4/2011 | Gregory et al. |
| 2011/0201055 | A1 | 8/2011 | Doyon et al. |
| 2012/0195936 | A1 | 8/2012 | Rudolph et al. |
| 2013/0196373 | A1 | 8/2013 | Gregory et al. |
| 2013/0253040 | A1 | 9/2013 | Miller et al. |
| 2015/0056705 | A1 | 2/2015 | Conway et al. |
| 2015/0079038 | A1 | 3/2015 | Deverman et al. |
| 2015/0267205 | A1 | 9/2015 | Froelich et al. |
| 2015/0335708 | A1 | 11/2015 | Froelich et al. |
| 2015/0353917 | A1 | 12/2015 | Miller |
| 2016/0355796 | A1 | 12/2016 | Davidson et al. |
| 2017/0145394 | A1 | 5/2017 | Yeo et al. |
| 2018/0057838 | A1 | 3/2018 | Khalil et al. |
| 2018/0087072 | A1 | 3/2018 | Miller et al. |
| 2018/0153921 | A1 | 6/2018 | Ledeboer et al. |
| 2019/0167815 | A1 | 6/2019 | Holmes et al. |
| 2021/0260219 | A1 | 8/2021 | Cowan et al. |

FOREIGN PATENT DOCUMENTS

| | | |
|---|---|---|
| WO | WO 95/19431 | 7/1995 |
| WO | WO 96/06166 | 2/1996 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/27878 | 5/2000 |
| WO | 2001025255 A2 | 4/2001 |
| WO | WO 01/60970 | 8/2001 |
| WO | WO 01/88197 | 11/2001 |
| WO | WO 02/016536 | 2/2002 |
| WO | WO 02/099084 | 12/2002 |
| WO | WO 03/016496 | 2/2003 |
| WO | WO 2010/079430 | 7/2010 |
| WO | WO 2011/139349 | 11/2011 |
| WO | 2014/134351 A2 | 9/2014 |
| WO | 2015/070212 A1 | 5/2015 |
| WO | WO 2015/153760 A2 | 10/2015 |
| WO | 2016063264 A1 | 4/2016 |
| WO | WO 2017/040813 | 3/2017 |
| WO | 2018002762 A1 | 1/2018 |
| WO | WO 2018/035423 | 2/2018 |
| WO | WO 2018/102665 | 7/2018 |

OTHER PUBLICATIONS

Ansseau, et al., "Antisense Oligonucleotides Used to Target the DUX4 mRNA as Therapeutic Approaches in Facioscapulohumeral Muscular Dystrophy (FSHD)," Genes (2017) 8(3):93.

Argast et al., "I-Ppol and I-Crel Homing Site Sequence Degeneracy Determined by Random Mutagenesis and Sequential in Vitro Enrichment," J Mol Biol. (1998) 280:345-53.

Ashworth, et al., "Computational Redesign of Endonuclease DNA Binding and Cleavage Specificity," Nature (2006) 441:656-59.

Bailus, et al., "Protein Delivery of an Artificial Transcription Factor Restores Widespread Ube3A Expression in an Angelman Syndrome Mouse Brain," Mol Ther. (2016) 24(3):548-55.

Bannister, et al., "Regulation of Chromatin by Histone Modifications," Cell Research (2011) 21(3):381-95.

Bao, et al., "Targeting mRNA for the Treatment of Facioscapulohumeral Muscular Dystrophy," Intractable Rare Dis Res. (2016) 5(3):168-76.

Beerli et al., "Positive and Negative Regulation of Endogenous Genes by Designed Transcription Factors," PNAS (2000) 97(4):1495-500.

Belfort et al., "Homing Endonucleases: Keeping the House in Order," Nucleic Acids Res. (1997) 25(17):3379-88.

Benussi et al., "Phenotypic Heterogeneity of Monogenic Frontotemporal Dementia," Front Aging Neurosci. (2015) 7:171.

Beurdeley, et al., "Compact Designer TALENs for Efficient Genome Engineering," Nat Comm. (2013) 4(1762):1-8.

Bevan, et al., "Systemic Gene Delivery in Large Species for Targeting Spinal Cord, Brain, and Peripheral Tissues for Pediatric Disorders," Mol Ther. (2011) 19(11):1971-980.

Bird et al., "Methylation-Induced Repression—Belts, Braces, and Chromatin," Cell (1999) 99:451-54.

Bird, "Angelman Syndrome: Review of Clinical and Molecular Aspects," Appl Clin Genet. (2014) 7:93-104.

(56) References Cited

OTHER PUBLICATIONS

Bitinaite, et al., "Fok1 Dimerization is Required for DNA Cleavage," Proc. Natl. Acad Sci USA (1998) 95:10,570-10,575.
Boch et al., "Breaking the Code of DNA Binding Specificity of TAL-type III Effectors," Science (2009) 326:1509-512.
Boissel, et al., "megaTALs: A Rare-Cleaving Nuclease Architecture for Therapeutic Genome Engineering," Nucleic Acids Research (2013) 42(4):2591-601.
Bonas, et al., "Genetic and Structural Characterization of the Avirulence Gene AVRBS3 From Xanthomonas Campestris Pv. Vesicatoria," Mol Gen Genet. (1989) 218:127-36.
Brouns, et al., "Small CRISPR RNAs Guide Antiviral Defense in Prokaryotes," Science (2008) 321:960-64.
Burstein, et al., "New CRISPR-Cas Systems from Uncultivated Microbes," Nature (2017) 542(7640):237-41.
Cebrian-Serrano, et al., "CRISPR-Cas Orthologues and Variants: Optimizing the Repertoire, Specificity and Delivery of Genome Engineering Tools," Mamm Genome (2017) 28(7):247-61.
Cedar, et al., "Linking DNA Methylation and Histone Modification: Patterns and Paradigms," Nature Rev Gene. (2009) 10:295-304.
Chen et al., "Cerebrospinal Fluid Inflammatory Cytokine Aberrations in Alzheimer's Disease, Parkinson's Disease and Amyotrophic Lateral Sclerosis: a Systematic Review and Meta-Analysis," Front Immunol. (2018) 9(2122):1-12.
Chern et al., "The Regulator of MAT2 (ROM2) Protein Binds to Early Maturation Promoters and Represses PvALF-Activated Transcription," Plant Cell (1996) 8:305-21.
Chevalier, et al., "Design, Activity, and Structure of a Highly Specific Artificial Endonuclease," Molec Cell (2002) 10:895-905.
Clayton-Smith, et al., "Angelman Syndrome: A Review of the Clinical and Genetic Aspects," J Med Genet. 40(2):87-95 (2003).
Cong, et al., "Multiplex Genome Engineering Using CRISPR/Cas Systems," Science (2013) 339(6121):819-23.
Davidson et al., "A Model System for in Vivo Gene Transfer into the Central Nervous System Using an Adenoviral Vector," Nat Genet. (1993) 3:219-23.
Davidson et al., "Recombinant Adeno-Associated Virus Type 2, 4, and 5 Vectors: Transduction of Variant Cell Types and Regions in the Mammalian Central Nervous System," PNAS (2000) 97(7):3428-432.
Daxinger, et al., "Genetic and Epigenetic Contributors to FSHD," Curr Opin Genet Dev. (2015) 33:56-61.
Douglas, "Non-Coding RNA in C9orf72-Related Amyotrophic Lateral Sclerosis and Frontotemporal Dementia: a Perfect Storm of Dysfunction," Non-coding RNA Res. (2018) 3:178-87.
Dujon et al., "Mobile Introns: Definition of Terms and Recommended Nomenclature," Gene (1989) 82:115-18.
Epinat, et al., "A Novel Engineered Meganuclease Induces Homologous Recombination in Yeast and Mammalian Cells," Nucleic Acids Res. (2003) 31(11):2952-962.
Esvelt, et al., "Orthogonal CAS9 Proteins for RNA-Guided Gene Regulation and Editing," Nature Methods (2013) 10(11):1116.
Fagerlund, et al., "The Cpf1 CRISPR-Cas Protein Expands Genome-Editing Tools," Genom Bio. (2015) 16:251.
Fonfara, et al., "Phylogeny of Cas9 Determines Functional Exchangeability of Dual-RNA and Cas9 Among Orthologous Type II CRISPR-Cas Systems," Nucleic Acids Research (2013) 42(4):2577-590.
Freibaum, et al., "The Role of Dipeptide Repeats in C9ORF72-Related ALS-FTD," Front Mol Neurosci. (2017) 10:35.
Fu, et al., "Improving CRISPR-Cas Nuclease Specificity Using Truncated Guide RNAs," Nature Biotechnol. (2014) 32(3):279-84.
Gendron et al., "Antisense Transcripts of the Expanded C9ORF72 Hexanucleotide Repeat Form Nuclear RNA Foci and Undergo Repeat-Associated Non-ATG Translation in c9FTD/ALS," Acta Neuropathol. (2013) 126:829-44.
Gersbach et al., "Synthetic Zinc Finger Proteins: the Advent of Targeted Gene Regulation and Genome Modification Technologies," Accounts of Chemical Research (2014) 47(8):2309-18.
Ghosh, et al., "Gene Suppression Approaches to Neurodegeneration," Alzheimer's Research & Therapy (2017) 9(1):1-13.
Gimble et al., "Substrate Recognition and Induced DNA Distortion by the PI-ScelEndonuclease, an Enzyme Generated by Protein Splicing," J Mol Biol. (1996) 263:163-80.
Godde, et al., "The Repetitive DNA Elements Called CRISPRs and Their Associated Genes: Evidence of Horizontal Transfer Among Prokaryotes," J Mol Evol. (2006) 62:718-29.
Guilinger, et al., "Fusion of Catalytically Inactive Cas9 to Fok1 Nuclease Improves the Specificity of Genome Modification," Nature Biotech. (2014) 32(6):577-82.
Guo, et al., "Directed Evolution of an Enhanced and Highly Efficient Fok1 Cleavage Domain for Zinc Finger Nucleases," J. Mol. Biol. (2010) 400(1):96-107.
Gurda, et al., "Evaluation of AAV-Mediated Gene Therapy for Central Nervous System Disease in Canine Mucopolysaccharidosis VII," Molecular Therapy (2016) 24(2):206-16.
Hadaczek et al., "Eight Years of Clinical Improvement in MPTP-Lesioned Primates After Gene Therapy with AAV2-hAADC," Mol Ther. (2010) 18(8):1458-461.
Haft, et al., "A Guild of 45 CRISPR-Associated (Cas) Protein Families and Multiple CRISPR/Cas Subtypes Exist in Prokaryotic Genomes," PLoS Computational Biology (2005) 1(6)e60:474-83.
Hale, et al., "Prokaryotic Silencing (psi)RNAs in Pyrococcus Furiosus," RNA (2008) 14:2572-579.
Heuer, et al., "Repeat Domain Diversity of AVRBS3-Like Genes in Ralstonia Solanacearum Strains and Association with Host Preferences in the Field," Applied and Environmental Microbiology (2007) 73(13):4379-384.
Hilton, et al., "Epigenome Editing by a CRISPR/Cas9-Based Acetyl Transferase Activates Genes from Promoters and Enhancers," Nat Biotechnol. (2015) 33(5):510-17.
Hsiao, et al., "Upregulation of Haploinsufficient Gene Expression in the Brain by Targeting a Long Non-Coding RNA Improves Seizure Phenotype in a Model of Dravet Syndrome," EBioMedicine (2016) 9:257-77.
Hsu, et al., "DNA Targeting Specificity of RNA-Guided Cas9 Nucleases," Nat Biotechnol. (2013) 31(9):827-32.
Hwang et al., "Efficient in Vivo Genome Editing Using RNA-Guided Nucleases," Nature Biotechnology (2013) 31(3):227-29.
Iascone, et al., "Spinal Muscular Atrophy: from Tissue Specificity to Therapeutic Strategies," F1000 Pri Rep. (2015) 7:04.
Jackson, et al., "Initial Gene Vector Dosing for Studying Symptomatology of Amyotrophic Lateral Sclerosis in Non-Human Primates," J. Med Primatol. (2015) 44(2):66-75.
Jansen, et al., "Identification of Genes that are Associated with DNA Repeats in Prokaryotes," Molecular Microbiology (2002) 43(6):1565-575.
Jasin, "Genetic Manipulation of Genomes with Rare-Cutting Endonucleases," Trends Genet. (1996) 12(6):224-28.
Jinek et al., "A Programmable Dual-RNA-Guided DNA Endonuclease in Adaptive Bacterial Immunity," Science (2012) 337:816-21.
Johnston, et al., "Symptomatic Models of Parkinson's Disease and L-DOPA-Induced Dyskinesia in Non-Human Primates," Curr Top Behav Neurosci. (2015) 22:221-35.
Kabadi, et al., "Engineering Synthetic TALE and CRISPR/ Cas9 Transcription Factors for Regulating Gene Expression," Methods (2014) 69(2):188-97.
Kadiyala, et al., "Spatiotemporal Differences in the c-fos Pathway Between C57BL/6J and DBA/2J Mice Following Flurothyl-Induced Seizures: A Dissociation of Hippocampal Fos from Seizure Activity," Epilepsy Res. (2015) 109:193-96.
Kay et al., "A Bacterial Effector Acts as a Plant Transcription Factor and Induces a Cell Size Regulator," Science (2007) 318:648-51.
Kleinstiver, et al., "High-Fidelity CRISPR-Cas9 Variants with Undetectable Genome-Wide Off-Targets," Nature (2016) 529(7587):490-95.
Knoepfler et al., "Sin Meets NuRD and Other Minireview Tails of Repression," Cell (1999) 99:447-50.
Kormann et al., "Expression of Therapeutic Proteins After Delivery of Chemically Modified mRNA in Mice," Nature Biotechnology (2011) 29(2):154-57.
Kouzarides, "Chromatin Modifications and Their Function," Cell (2007) 128:693-705.

(56) References Cited

OTHER PUBLICATIONS

Laganiere, et al., "An Engineered Zinc Finger Protein Activator of the Endogenous Glial Cell Line-Derived Neurotrophic Factor Gene Provides Functional Neuroprotection in a Rat Model of Parkinson's Disease," Journal of Neuroscience (2010) 30(49):16469-6474.

Lagier-Tourenne et al., "Targeted Degradation of Sense and Antisense C9orf72 RNA Foci as Therapy for ALS and Frontotemporal Degeneration," PNAS (2013) 110(47):E4530-39.

Li, et al., "Application of APP/PS1 Transgenic Mouse Model for Alzheimer's Disease," J Alzheimers Dis Parkin. (2015) 5(3):201.

Lillestøl, et al., "A Putative Viral Defense Mechanism in Archaeal Cells," Archaea (2006) 2:59-72.

Lister, et al., "Human DNA Methylomes at Base Resolution Show Widespread Epigenomic Differences," Nature (2009) 462(7271):315-22.

Liu et al., "C9orf72 BAC Mouse Model with Motor Deficits and Neurodegenerative Features of ALS/FTD," Neuron (2016) 90(3):521-34.

Liu, et al., "Regulation of an Endogenous Locus Using a Panel of Designed Zinc Finger Proteins Targeted to Accessible Chromatin Regions," Journal of Biological Chemistry (2001) 276(14):11323-1334.

Ma, et al., "Rational Design of Mini-Cas9 for Transcriptional Activation," ACS Synth Biol. (2018) 7(4):978-85.

Maarel, et al., "Facioscapulohumeral Muscular Dystrophy and DUX4: Breaking the Silence," Trends Mol Biol. (2011) 17(5):252-58.

Makarova, et al., "A DNA Repair System Specific for Thermophilic Archaea and Bacteria Predicted by Genomic Context Analysis," Nucleic Acids Research (2002) 30(2):482-96.

Makarova, et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biology Direct. (2006) 1(7):1-26.

McCaffery, et al., "CRISPR-CAS9 D10A Nickase Target-Specific Fluorescent Labeling of Double Strand DNA for Whole Genome Mapping and Structural Variation Analysis," Nucleic Acids Res. (2016) 44(2).

Meng, et al., "Ube3a-ATS is an Atypical RNA Polymerase II Transcript that Represses the Paternal Expression of Ube3A," Hum Mol Genet. (2012) 21(13):3001-012.

Miller et al., "A Tale Nuclease Architecture for Efficient Genome Editing," Nat Biotech. (2011) 29(2):143-50.

Moscou, et al., "A Simple Cipher Governs DNA Recognition by TAL Effectors," Science (2009) 326:1501.

Mottamal, et al., "Histone Deacetylase Inhibitors in Clinical Studies as Templates for New Anticancer Agents," Molecules (2015) 20(3):3898-941.

Niblock et al., "Retention of Hexanucleotide Repeat-Containing Intron in C9orf72 mRNA: Implications for the Pathogenesis of ALS FTD," Acta Neuropathologica Communications (2016) 4(1):1-12.

Niwa et al., "Efficient Selection for High-Expression Transfectants with a Novel Eukaryotic Vector," Gene (1991) 108(2):193-99.

Ong, et al., "Enhancer Function: New Insights into the Regulation of Tissue-Specific Gene Expression," Nat Rev Genetics (2011) 12(4):283-93.

Paques, et al., "Meganucleases and DNA Double-Strand Break-Induced Recombination: Perspectives for Gene Therapy," Current Gene Therapy (2007) 7:49-66.

Park, et al., "Quantitative Expression Analysis of APP Pathway and Tau Phosphorylation-Related Genes in the ICV STZ-Induced Non-Human Primate Model of Sporadic Alzheimer's Disease," Int J Mol Sci. (2015) 16(2):2386-402.

Perler et al., "Protein Splicing Elements: Inteins and Exteins a Definition of Terms and Recommended Nomenclature," Nucleic Acids Res. (1994) 22(7):1125-127.

Pribadi et al., "CRISPR-Cas9 Targeted Deletion of the C9orf72 Repeat Expansion Mutation Corrects Cellular Phenotypes in Patient-Derived iPS Cells," bioRxiv (2016) 1-32.

Ramalingam et al., "A CRISPR Way to Engineer the Human Genome," Genome Biol. (2013) 14:107.

Remacle et al., "New Mode of DNA Binding of Multi-Zinc Finger Transcription Factors: deltaEF1 Family Members Bind with Two Hands to Two Target Sites," EMBO J. (1999) 18(18):5073-084.

Renton et al., "A Hexanucleotide Repeat Expansion in C9ORF72 is the Cause of Chromosome 9p21-Linked ALS-FTD," Neuron (2011) 72:257-68.

Riemslagh et al., "HR23B Pathology Preferentially Co-Localizes with p62, pTDP-43 and Poly-GA in C9ORF72-Linked Frontotemporal Dementia and Amyotrophic Lateral Sclerosis," Acta Neuropathol Commun. (2019) 7:39.

Rizzu et al., "C9orf72 is Differentially Expressed in the Central Nervous System and Myeloid Cells and Consistently Reduced in C9orf72, MAPT and GRN Mutation Carriers," Acta Neuropathologica Communications (2016) 4:37.

Robertson et al., "DNMT1 Forms a Complex with Rb, E2F1 and HDAC1 and Represses Transcription from E2F-Responsive Promoters," Nature Genet. (2000) 25:338-42.

Sander, et al., "CRISPR-Cas Systems for Genome Editing, Regulation and Targeting," Nature Biotechnol. (2014) 32(4):347-55.

Schornack et al., "Gene-for-Gene-Mediated Recognition of Nuclear-Targeted AvrBs3-like Bacterial Effector Proteins," J Plant Physiol. (2006) 163(3):256-72.

Schutt, et al., "Dogs with Cognitive Dysfunction as a Spontaneous Model for Early Alzheimer's Disease: A Translational Study of Neuropathological and Inflammatory Markers," J Alzheimer's Dis. (2016) 52(2):433-49.

Sheng, et al., "Structure-Based Cleavage Mechanism of Thermus Thermophilus Argonaute DNA Guide Strand-Mediated DNA Target Cleavage," Proc. Natl. Acad. Sci. USA. (2014) 111(2):652-57.

Shirvanian, "Sangamo and Pfizer Announce Collaboration for Development of Zinc Finger Protein Gene Therapy for ALS," Pfizer Press Release (2018) 1-4. Retrieved from the Internet:https://www.pfizer.com/news/press-release/press-release-detail/sangamo_and_pfizer_announce_collaboration_for_development_of_zinc_finger_protein_gene_t_herapy_for_als.

Sorek, et al., "CRISPR—A Widespread System that Provides Acquired Resistance Against Phages in Bacteria and Archaea," Nature Reviews Microbiology (2008) 6:181-86.

Stein et al., "Systemic and Central Nervous System Correction of Lysosomal Storage in Mucopolysaccharidosis Type VII mice," J Vir. (1999) 73(4):3424-429.

Stewart, et al., "Establishment and Functions of DNA Methylation in the Germline," Epigenomics (2016) 8(10):1399-413.

Swarts, et al., "DNA-Guided DNA Interference by a Prokaryotic Argonaute," Nature (2014) 507(7491):258-61.

Talbot, et al., "The Clinical Landscape for SMA in a New Therapeutic Era," Gene Ther. (2017) 24(9):529-33.

Tang, et al., "Identification of 86 Candidates for Small Non-Messenger RNAs from the Archaeon Archaeoglobus Fulgidus," Proc. Natt. Acad. Sci. (2002) 99(11):7536-541.

Tang, et al., "Identification of Novel Non-Coding RNAs as Potential Antisense Regulators in the Archaeon Sulfolobus Solfataricus," Molecular Microbiology (2005) 55(2):469-81.

Taylor, et al., "Neurodegenerative Diseases: G-Quadruplex Poses Quadruple Threat," Nature (2014) 507:175.

Troung, et al., "Development of an Intein-Mediated Split-Cas9 System for Gene Therapy," Nucl Acid Res. (2015) 43(13):6450-458.

Tyler et al., "The 'Dark Side' of Chromatin Remodeling: Repressive Effects on Transcription," Cell (1999) 99:443-46.

Van Blitterswijk et al., "Novel Clinical Associations with Specific C9ORF72 Transcripts in Patients with Repeat Expansions in C9ORF72," Acta Neuropathol. (2015) 130(6): 863-76.

Varatharajah, et al., "Seizure Forecasting and the Preictal State in Canine Epilepsy," Int J Neural Syst. (2017) 27(1):1650046.

Webster, et al., "Using Mice to Model Alzheimer's Dementia: An Overview of the Clinical Disease and the Preclinical Behavioral Changes in 10 Mouse Models," Front Genet. (2014) 5(88):1-23.

Wilen et al., "Engineering HIV-Resistant Human CD4+ T Cells with CXCR4– Specific Zinc-Finger Nucleases," PLoS (2011) 7(4):e1002020.

(56) References Cited

OTHER PUBLICATIONS

Wirth, et al., "Combinatory Biomarker Use of Cortical Thickness, Munix, and ALSFRS-R at Baseline and in Longitudinal Courses of Individual Patients with Amyotrophic Lateral Sclerosis," Front Neurol. (2018) 9:614.

Wu et al., "Functional Analysis of HD2 Histone Deacetylase Homologues in *Arabidopsis thaliana*," Plant J. (2000) 22(1):19-27.

Wu, et al., "Genome-Wide Binding of the Crispr Endonuclease Cas9 in Mammalian Cells," Nature Biotechnology (2014).

Yang, et al., "Towards a Transgenic Model of Huntington's Disease in a Non-Human Primate," Nature (2008) 453(7197):921-24.

Zaiss, et al., "Immunity to Adeno-Associated Virus Vectors in Animals and Humans: a Continued Challenge," Gene Ther. (2008) 15:808-16.

Zeitler, et al., "Allele-Selective Transcriptional Repression of Mutant HTT for the Treatment of Huntington's Disease," Nature Medicine (2019) 25(7):1131-42.

Zetsche, et al., "A Split-Cas9 Architecture for Inducible Genome Editing and Transcription Modulation," Nat Biotechnol. (2015) 33(2):139-42.

Zhang, et al., "A Designed Zinc-Finger Transcriptional Repressor of Phospholamban Impoves Function of the Failing Heart," Mol Ther. (2012) 20(8):1508-515.

Garriga-Canut, et al., "Synthetic Zinc Finger Repressors Reduce Mutant Huntingtin Expression in the Brain of R6/2 Mice," PNAS (2012) E3136-145.

Wu, et al., "Custom-designed Zinc Finger Nucleases: What is next", Cell Mol Life Sci. (2007) 64(22):2933-44.

U.S. Appl. No. 16/169,420, filed Oct. 24, 2018, Michael C. Holmes.

Samie, et al., "Selective Repression of C9ORF72 Repeat Expansion-Containing Transcripts for the Treatment of ALS," Molecular Therapy (2019) 27(4S1):260-1.

Kuznezova, "Parenthesis in an Official Document Text as a Linguo-cognitive Phenomenon," Vestnik MSOU. Series: Russian Philology (2015) 3:37-43.

Badri et al., "Optimization of Radiation Dosing Schedules for Proneural Glioblastoma," J. Math. Bio. (2016) 72(5):1301-36.

Baylot et al., "TCTP Has a Crucial Role in the Different Stages of Prostate Cancer Malignant Progression," Results Probl Cell Differ (2017) 64:255-61.

Barbara Celona et al., "Suppression of C9orf72 RNA repeat-induced neurotoxicity by the ALS-associated RNA-binding protein Zfp106," elife, 2017, vol. 6, doi: 10.7554/e Life. 19032, 17 pages.

Office Action issued for the Chinese Patent Application No. 202080031118.4 dated Jun. 19, 2024, 25 pages.

Office Action issued for the Colombian Patent Application No. 12396 dated Jul. 16, 2024, 14 pages.

\* cited by examiner

74960: Negative control – Minimal repression
74967: Positive control – Full repression
GFP: transfection controls

SEQUENCE LISTING

```
<160> NUMBER OF SEQ ID NOS: 85

<210> SEQ ID NO 1
<211> LENGTH: 6
<212> TYPE: DNA
<213> ORGANISM: Homo sapiens

<400> SEQUENCE: 1 ggggcc                                                                 6

<210> SEQ ID NO 2
<211> LENGTH: 6
<212> TYPE: DNA
<213> ORGANISM: Homo sapiens

<400> SEQUENCE: 2 gggccg                                                                 6

<210> SEQ ID NO 3
<211> LENGTH: 6
<212> TYPE: DNA
<213> ORGANISM: Homo sapiens

<400> SEQUENCE: 3 ggccgg                                                                 6

<210> SEQ ID NO 4
<211> LENGTH: 6
<212> TYPE: DNA
<213> ORGANISM: Homo sapiens

<400> SEQUENCE: 4 gccggg                                                                 6

<210> SEQ ID NO 5
<211> LENGTH: 6
<212> TYPE: DNA
<213> ORGANISM: Homo sapiens

<400> SEQUENCE: 5 ccgggg                                                                 6
```

-continued

```
<210> SEQ ID NO 6
<211> LENGTH: 6
<212> TYPE: DNA
<213> ORGANISM: Homo sapiens

<400> SEQUENCE: 6 cggggc                                                              6

<210> SEQ ID NO 7
<211> LENGTH: 6
<212> TYPE: DNA
<213> ORGANISM: Homo sapiens

<400> SEQUENCE: 7 ggcccc                                                              6

<210> SEQ ID NO 8
<211> LENGTH: 6
<212> TYPE: DNA
<213> ORGANISM: Homo sapiens

<400> SEQUENCE: 8 gccccg                                                              6

<210> SEQ ID NO 9
<211> LENGTH: 6
<212> TYPE: DNA
<213> ORGANISM: Homo sapiens

<400> SEQUENCE: 9 ccccgg                                                              6

<210> SEQ ID NO 10
<211> LENGTH: 6
<212> TYPE: DNA
<213> ORGANISM: Homo sapiens

<400> SEQUENCE: 10 cccggc                                                              6

<210> SEQ ID NO 11
<211> LENGTH: 6
<212> TYPE: DNA
<213> ORGANISM: Homo sapiens

<400> SEQUENCE: 11 ccggcc                                                              6

<210> SEQ ID NO 12
<211> LENGTH: 6
<212> TYPE: DNA
<213> ORGANISM: Homo sapiens

<400> SEQUENCE: 12 cggccc                                                              6

<210> SEQ ID NO 13
<211> LENGTH: 96
<212> TYPE: PRT
<213> ORGANISM: Homo sapiens

<400> SEQUENCE: 13

Asp Ala Lys Ser Leu Thr Ala Trp Ser Arg Thr Leu Val Thr Phe Lys
1               5                   10                  15
```

```
Asp Val Phe Val Asp Phe Thr Arg Glu Glu Trp Lys Leu Leu Asp Thr
            20                  25                  30

Ala Gln Gln Ile Val Tyr Arg Asn Val Met Leu Glu Asn Tyr Lys Asn
        35                  40                  45

Leu Val Ser Leu Gly Tyr Gln Leu Thr Lys Pro Asp Val Ile Leu Arg
    50                  55                  60

Leu Glu Lys Gly Glu Glu Pro Trp Leu Val Gly Arg Glu Ile His Gln
65                  70                  75                  80

Glu Thr His Pro Asp Ser Glu Thr Ala Phe Glu Ile Lys Ser Ser Val
                85                  90                  95

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Gly Gly Gly Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Glu Lys Pro
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Arg Gln Lys Asp Gly Glu Arg Pro
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Arg Arg
1

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 18

Gly Gly Arg Arg Gly Gly Gly Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Arg Gln Arg Asp Gly Glu Arg Pro
1               5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Arg Gln Lys Asp Gly Gly Gly Ser Glu Arg Pro
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Arg Gln Lys Asp Gly Gly Ser Gly Gly Ser Glu Arg Pro
1               5                   10                  15

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Gly Ser Gln Lys Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser
1               5

<210> SEQ ID NO 24

```
<211> LENGTH: 28
<212> TYPE: DNA
<213> ORGANISM: Homo sapiens

<400> SEQUENCE: 24 tagggggccgg ggccggggcc ggggcgtg                                    28

<210> SEQ ID NO 25
<211> LENGTH: 28
<212> TYPE: DNA
<213> ORGANISM: Homo sapiens

<400> SEQUENCE: 25
cacgccccgg ccccggcccc ggcccta                                      28

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Arg Gln Lys Asp Ala Ala Arg Gly Ser
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Arg Ser Asp Leu Ser Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ser Thr His Leu Val Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Ala His Leu Ser Arg
1               5

<210> SEQ ID NO 30
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 30

Glu Arg Gly Asp Leu Lys Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Arg Gly Thr Leu Ala Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ser Ala Asp Leu Ser Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ser Asp His Leu Ser Glu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asp Arg Ser His Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ser Asp His Leu Ser Gln
1               5
```

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asn Ser His Arg Thr Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Asn Gly His Leu Leu Asp
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Ala His Leu Ser Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp His Leu Ser Arg
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Trp Thr Thr Arg Arg Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 41

His Arg Lys Ser Leu Ser Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Ser Ser Asp Arg Lys Lys
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Ser Ser Thr Arg Arg Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Asp Arg Lys Thr
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ser Ala Asp Arg Lys Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Asn Ala Asp Arg Ile Thr
1               5

<210> SEQ ID NO 47
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Arg Arg Ala Thr Leu Leu Asp
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ser Asp Thr Leu Ser Val
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Thr Ser Thr Arg Thr Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ser Ala Thr Leu Ser Glu
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His His Arg Ser Leu His Arg
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ser Ser Asp Arg Thr Lys
1               5
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Asp Arg Ser His Leu Thr Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ser Ser Thr Arg Lys Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Lys Arg Asp Leu Ala Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Ser Arg Tyr Arg Thr Lys
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Glu Gln Asp Leu Lys Gln
1               5

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 58
ctatgtgtgt ggtgggatat gg                                              22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctccaggtta tgtgaagcag aa                                              22

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
aggcctgcta aaggattcaa ctggaa                                          26

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccctctctcc ccactacttg                                                 20

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctacaggctg cggttgtttc c                                               21

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
tctcacagta ctcgctgagg gtga                                            24

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 64
ctctagcgac tggtggaatt g                                              21

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gtgcatggca actgtttgaa ta                                             22

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
caaagcctgg tggtgttcaa                                                20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ggacatgacc tggttgcttc                                                20

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
cgcggccaga tagacccaat gagca                                          25

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
actacttgct ctcacagtac tcg                                            23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
```
tagcgcgcga ctcctgagtt cc                                          22

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
agggaaacaa ccgcagcctg tagcaagctc                                  30

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgtgacagtt ggaatgcagt ga                                          22

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gccacttaaa gcaatctctg tcttg                                       25

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
tcgactcttt gcccaccgcc a                                           21

<210> SEQ ID NO 75
<211> LENGTH: 16
<212> TYPE: DNA
<213> ORGANISM: Homo sapiens

<400> SEQUENCE: 75
ccggggccgg ggccgg                                                 16

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Arg Gln Lys Asp Ala Ala Arg Gly Ser Gly Gly
1               5                   10

```
<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Arg Arg Asp Leu Arg Arg
1               5

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cagcttcggt cagagaaatg ag                                            22

<210> SEQ ID NO 79
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aagaggcgcg ggtagaa                                                  17

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
ctctcctcag agctcgacgc attt                                          24

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
agtcgctaga ggcgaaagc                                                19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cgagtgggtg agtgaggag                                                19
```

```
<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
aagaggcgcg ggtagaagcg ggggc                                              25

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ggccccggcc ccggcccc                                                      18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
ggggccgggg ccggggcc                                                      18
```

MODULATORS OF CHROMOSOME 9 OPEN READING FRAME 72 GENE EXPRESSION AND USES THEREOF

CROSS REFERENCE TO RELATED APPLICATIONS

This application claims priority from U.S. Patent Applications 62/837,523, filed Apr. 23, 2019, and 62/964,844, filed Jan. 23, 2020. The disclosures of these priority applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 21, 2020, is named 025297_US017_SL.txt and is 18,362 bytes in size.

BACKGROUND OF THE INVENTION

The chromosome 9 open reading frame 72 (C9orf72) gene encodes a protein that is found abundantly in neurons. The C9orf72 protein is thought to play an important role in endosomal trafficking. Although the function of the C9orf72 protein is not well understood, recent data suggest that it plays a role in membrane trafficking along the endolysosomal pathways by regulating the function of Rab proteins.

The C9orf72 gene contains in intron 1 a hexanucleotide segment ($G_4C_2$; SEQ ID NO:1). This segment can repeat in tandem up to 30 times with no discernible biological effect. However, repeats of more than 30 times, a phenomenon called hexanucleotide expansion, can lead to C9orf72-related disorders (Renton et al., *Neuron* (2011) 72:257-68; Douglas, *Non-coding RNA Res.* (2018) 3:178-87). This expansion results in an autosomal dominant phenotype, and patients typically are heterozygous for the expanded allele. It appears that hexanucleotide expansion causes formation of RNA foci within the cell, leading to sequestration of RNA-binding proteins and disruption of RNA metabolism. It also appears that through non-AUG dependent translation, the hexanucleotide expansion leads to production of unnatural proteins containing dipeptide repeats (DPR) from potentially all six frames in both the sense and antisense directions (Freibaum and Taylor, *Front Mol Neurosci.* (2017) 10:35; Douglas, supra). These proteins are prone to aggregation (Gendron et al., *Acta Neuropathol.* (2013) 126:829). DPRs have been reported as inclusions in post-mortem brain material of patients with C9orf72-related diseases (Riemslagh et al., *Acta Neuropathol Commun.* (2019) 7:39).

C9orf72-related disorders include amyotrophic lateral sclerosis (ALS) and C9 familial frontotemporal dementia (C9FTD). ALS is characterized by progressive muscle weakness, a loss of muscle mass, and a gradually declined ability to move, speak, swallow, and/or breathe. ALS has an annual incidence rate of 1-3 cases per 100,000 people and is the most common adult-onset motor neuron disorder. This disease is fatal to most patients within three to five years of the first symptoms. Mutations in the C9orf72 gene are responsible for about 30 to 40 percent of familial ALS in the United States and Europe, and account for 5-10% of sporadic ALS. Some patients with C9orf72-related ALS also develop a condition called C9 frontotemporal dementia (FTD) or C9FTD, a neurodegenerative disease that affects personality, behavior, and language (Benussi et al., *Front Aging Neurosci.* (2015) 7:171). Individuals who develop both conditions are diagnosed as having ALS-FTD.

There has been no effective treatment for C9orf72-related disorders. Thus, there is an urgent need to develop efficacious therapies for these disorders.

SUMMARY OF THE INVENTION

The present disclosure provides zinc finger protein-based transcription modulators of human C9orf72 and use of these modulators in treating C9orf72-related disorders. In one aspect, the present disclosure provides a fusion protein comprising a zinc finger protein (ZFP) domain and a transcription repressor domain, wherein the ZFP domain binds to a target region in an intronic segment (intron 1a) between exons 1a and 1b of a mutant allele of a human C9orf72 gene. The mutant allele has an expanded $G_4C_2$ (SEQ ID NO:1) repeat region in intron 1a, and the fusion protein targets this expanded repeat region. A mutant allele may comprise more than 30 tandem $G_4C_2$ repeats (e.g., more than 100, 200, 300, 400, 500, 600, 700, 800, 900, or 1000 repeats). A wildtype allele may comprise no more than 30 such repeats (e.g., no more than 25, 20, 15, 10, or 5 repeats).

In some embodiments, the fusion protein represses transcription of repeat-containing RNA transcripts (e.g., mRNA) from the mutant allele and does not repress transcription of wildtype RNA transcripts (e.g., mRNA) from the gene.

In some embodiments, the ZFP domain binds to a sense sequence in the target region, wherein the sense sequence comprises one to three tandem repeats of hexanucleotide GGGGCC (SEQ ID NO:1), GGGCCG (SEQ ID NO:2), GGCCGG (SEQ ID NO:3), GCCGGG (SEQ ID NO:4), CCGGGG (SEQ ID NO:5), or CGGGGC (SEQ ID NO:6). In certain embodiments, the fusion protein represses sense transcription from the mutant allele in a human cell. In particular embodiments, the fusion protein represses sense transcription from the C9orf72 1a promoter and does not repress sense transcription from the C9orf72 1b promoter.

In some embodiments, the ZFP domain binds to an antisense sequence in the target region, wherein the antisense sequence comprises one to three tandem repeats of hexanucleotide GGCCCC (SEQ ID NO:7), GCCCCG (SEQ ID NO:8), CCCCGG (SEQ ID NO:9), CCCGGC (SEQ ID NO:10), CCGGCC (SEQ ID NO:11), or CGGCCC (SEQ ID NO:12). In certain embodiments, the fusion protein represses antisense transcription from the mutant allele in a human cell.

In some embodiments, the fusion protein represses both sense transcription and antisense transcription from the mutant C9orf72 allele in a human cell. In some embodiments, the fusion protein preferentially represses a mutant C9orf72 allele as compared to a wildtype C9orf72 allele.

In further embodiments, the fusion protein represses sense and/or antisense transcription from the mutant allele by at least about 30%, 40%, 75%, 90%, or 95%.

In some embodiments, the fusion protein has one or more ZFP domains each of which optionally comprises six zinc fingers; binds to a target sequence shown in Table 1; and/or comprises the six zinc fingers (ordered F1 to F6), each zinc finger comprising a DNA-binding (recognition) helix sequences shown in a single row of Table 1, optionally comprising one or more mutations to residues outside the recognition helix regions as indicated in Table 1. In further embodiments, the fusion protein binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 78021, 75114, 75115, 74969, 79895, 79898, 74986, 79899, 79901, 79902, 79904, 79916, 75027, or 79921.

In some embodiments, the fusion protein has one or more transcription repressor domains each of which optionally comprises a KRAB domain amino acid sequence from human KOX1 such as those described further below. In particular embodiments, the ZFP domain is linked to the transcription repressor domain through a peptide linker.

In another aspect, the present disclosure provides a nucleic acid construct comprising a coding sequence for one or more of the fusion proteins described herein, wherein the coding sequence is optionally linked operably to a transcription regulatory element. In some embodiments, the transcription regulatory element comprises a mammalian promoter that is constitutively active or inducible in a brain cell, and wherein the promoter is optionally a human synapsin I promoter. In some embodiments, the construct is a recombinant adeno-associated viral ("AAV" or "rAAV") construct. Also provided are rAAVs comprising the recombinant AAV constructs and capsids of serotypes 1-10 (e.g., AAV2, AAV6, or AAV9), or of pseudotypes derived therein (e.g., AAV2/9, AAV2/6, or AAV2/6/9).

In another aspect, the present disclosure provides a host cell comprising one or more fusion proteins and/or one or more nucleic acid constructs as described herein. The host cell may be, for example, a human cell, such as a neuron or a pluripotent stem cell (e.g., embryonic stem cell or an inducible pluripotent stem cell).

Also provided are pharmaceutical compositions comprising one or more of the fusion proteins, one or more nucleic acid constructs (e.g., AAV constructs), recombinant viruses comprising the nucleic acid constructs (e.g., rAAVs), and/or one or more host cells as described herein, typically in combination with one or more pharmaceutically acceptable excipients.

In yet another aspect, the present disclosure provides a method of inhibiting transcription of a mutant C9orf72 allele in a human cell (e.g., a neuron, a glial cell, an ependymal cell, or a neuroepithelial cell), wherein the mutant allele comprises an expanded $G_4C_2$ repeat region in intron 1a, the method comprising introducing to the cell one or more fusion proteins, one or more nucleic acid constructs (e.g., AAVs), one or more recombinant viruses, one or more host cells and/or one or more pharmaceutical compositions as described herein. In some embodiments, the cell is in the brain or spinal cord of a patient suffering from a C9orf72-related disorder such as ALS or C9FTD.

In a related aspect, the present disclosure provides a method of treating a patient suffering from a C9orf72-related disorder optionally selected from amyotrophic lateral sclerosis (ALS) and C9 familial frontotemporal dementia (C9FTD), the method comprising introducing to the patient one or more fusion proteins, one or more nucleic acid constructs (e.g., AAVs), one or more host cells and/or one or more pharmaceutical compositions as described herein.

In the present treatment methods, the fusion protein may be introduced using a recombinant virus that expresses the fusion protein (e.g., AAV vectors). In some embodiments, the recombinant virus is administered via an intracerebroventricular, intrathecal, intracranial, retro-orbital (RO), intravenous, intranasal and/or intracisternal route to the patient. In some embodiments, two or more different fusion proteins of the present disclosure are introduced, wherein the coding sequences for the two or more fusion proteins may be carried on the same or different recombinant viral vectors.

Also provided in the present disclosure are one or more fusion proteins, and/or one or more nucleic acid constructs, one or more recombinant viruses, and one or more pharmaceutical compositions for use in the treatment methods described herein and use of the fusion proteins, nucleic acid constructs, and recombinant viruses for the manufacture of a medicament for use in the treatment methods described herein.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

BRIEF DESCRIPTION OF THE FIGURES

FIG. 1A shows the structure of both the wildtype C9orf72 allele and the expanded mutant C9orf72 allele. The location of the $G_4C_2$ expansion on the expanded mutant allele is indicated (in the genomic region between exons 1a and 1b, i.e., intron 1a). Exons are shown as boxes. Adapted from Douglas, supra; see also Rizzu et al. (2016) *Acta Neuropathologica Communications* 4:37.

FIG. 1B is an enlarged view of the region on the mutant expanded C9orf72 allele near the $G_4C_2$ expansion and depicts the promoters and transcripts associated with the expanded allele. Shown are the promoters involved in sense strand transcription (solid arrows) and the approximate location of promoters involved in antisense transcription (hollow arrows). Also shown are the 5 different sense transcripts that have been previously described, and the approximate location and transcripts that are in the antisense direction. Ibid.

FIG. 1C shows a model of repression of the 1a promoter and the antisense promoter by a ZFP-TF targeting the expanded region, wherein the ZFP-TF binds in a position that is downstream of both promoters and optimal for promoter regulation. The 1b promoter in this model is not repressed because binding of the ZFP-TF is upstream of the 1b promoter.

FIG. 2A illustrates the PCR assays used for the Total C9 assay and the sense and antisense repeat-containing isoform specific assays. The top of the figure depicts the genomic structure of the wildtype and expanded alleles, while the bottom of the figure shows the mRNA products made from each allele. Arrow sets on the mRNA drawings depict the PCR targets used in the Total C9 assay.

FIGS. 2B-D are graphs showing the results of the C9orf72 expression assays for different exemplary ZFP-TFs in a wildtype cell line derived from a healthy individual and an ALS patient-derived fibroblast cell line "C9." The C9 cell line is characterized as "5/850", which refers to the numbers of $G_4C_2$ repeats on the wildtype allele (5) and the expanded allele (850). Left most graphs: total C9orf72 expression ("Total C9") in wildtype cells in a 3$^{rd}$ round of screening ("Round 3"). Graphs second from the left: Total C9 in C9 cells in Round 3. Graphs second from the right: Total C9 in C9 cells in a 2$^{nd}$ round of screening ("Round 2"). Right most graphs: expression from the expanded C9orf72 allele as determined by an isoform-specific C9orf72 assay. The Round 2 screen was done in C9 cells to evaluate isoform (or disease) specific C9orf72 transcript levels vs. Total C9 transcript levels following ZFP-TF treatment. In Round 3, Total C9 was determined in C9 cells and wildtype cells in order to evaluate the ZFP-TFs' effects on the C9 cells' wildtype (WT) allele. For each ZFP-TF, concentrations of 1, 3, 10, 30, 100 and 300 ng mRNA are shown from left to right. FIG. 2B shows results for ZFP-TFs 74949, 74951, 74954, 74955 and 74964 in the top graphs and 74969, 74971, 74973, 74978 and 74979 in the bottom graphs. FIG. 2B discloses SEQ ID NOs:1, 1 and 3, respectively, in order of appearance. FIG. 2C shows results for ZFP-TFs 74983, 74984, 74986, 74987 and 74988 in the top graphs and 74997, 74998, 75001 and 75003 in the bottom graphs. FIG. 2C discloses SEQ ID NOs:4 and 5, respectively, in order of appearance. FIG. 2D shows results for ZFP-TFs 75023, 75027, 75031, 75032, 75055 and 75078 in the top graphs and 75090, 75105, 75109, 75114 and 75115 in the bottom graphs. FIG. 2D discloses SEQ ID NOs:8-11, respectively, in order of appearance. The sequence at the bottom of the graphs represents the DNA binding motif for that ZFP-TF. Each ZFP-TF binds to the three hexanucleotide repeat containing that motif. The transcript levels were normalized against those of green fluorescent protein (GFP) expressed from GFP mRNA transfected with ZFP-TF mRNAs. The horizontal dotted line in the graphs shows 50% or 70% repression as indicated. For example for ZFP-TF 75115, there was approximately 50% repression of the total isoform transcripts and about 70% repression of the repeat containing isoform specific transcripts in C9 line while there was minimal repression of total isoform in WT line. The graph indicates that 30% of the transcript remains, which indicates that 70% was repressed.

FIG. 4A shows that only cDNA template C9-AS produces a PCR product, indicating the specificity of the primers for detection of anti-sense pre-mRNA. FIG. 4B extends the experiment in FIG. 4A to 7 different C9orf72 patient-derived cell lines with different $G_4C_2$ repeat lengths and to 6 different healthy control lines.

FIG. 5A shows three experiments where ZFP-TFs 74949, 74978, 75003, 75027, 75109, 75114, 75115, 74960, and 74967 were given at three different doses (30, 100, or 300 ng) and then the amount of disease sense transcript was measured. FIG. 5B shows three experiments measuring the disease antisense transcript. FIG. 5C shows three runs measuring the total C9orf72 transcript.

FIG. 8A shows the results of microarray analysis in patient-derived primary fibroblast cells (C9021) using the Thermo Fisher Clariom™ S assay, which contains 21,000 well annotated genes in its database. Analysis was performed 24 hours after administration to C9021 cells of the repressors in mRNA form at 300 ng. The graphs illustrate genes that were up- or down-regulated in response to the indicated ZFP-TFs.

FIG. 8B shows the results of microarray analysis in mouse primary neurons using the Thermo Fisher Clariom™ D assay, which contains 140,000 annotated and unannotated coding and non-coding transcripts in its database. Analysis was performed 7 days after AAV transduction. All cells were transduced at the MOI of 3,000. The graphs illustrate genes that were up- or down-regulated in response to the indicated ZFP-TFs.

FIG. 8C shows the results of microarray analysis in human primary neurons using the Thermo Fisher Clariom™ D assay. Analysis was performed 19 days after AAV transduction of the cells at the MOI of 3,000. The graphs illustrate genes that were up- or down-regulated in response to the indicated ZFP-TFs.

DETAILED DESCRIPTION OF THE INVENTION

Figure 1A:
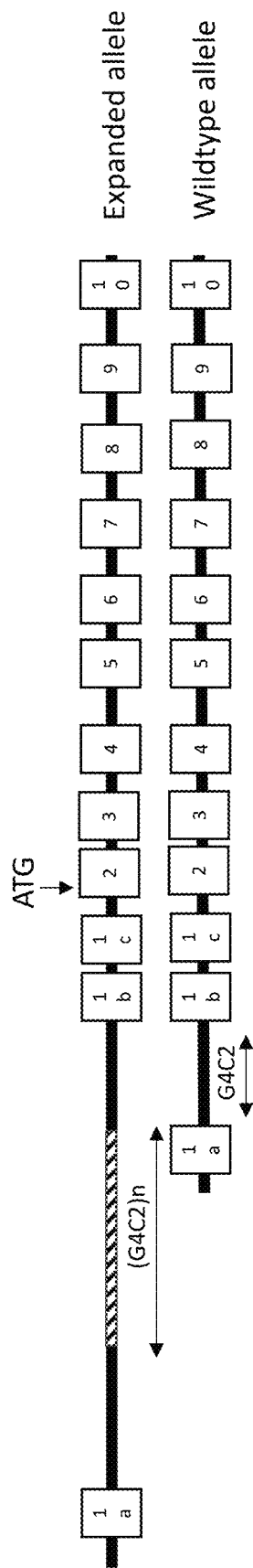
FIGS. 1A-C depict schematics of the C9orf72 gene and transcripts that are produced.

The present disclosure provides zinc finger protein-based transcription factors (ZFP-TFs) that preferentially target human C9orf72 gene alleles having an expanded $G_4C_2$ repeat region and repress the transcription of these mutant alleles into RNA. Such an expanded region may have more than 30 $G_4C_2$ repeats. The present ZFP-TFs are fusion proteins containing (i) at least one zinc finger protein (ZFP) domain that binds specifically to DNA motifs within the repeats on either the sense or antisense strand of a mutant allele, and (ii) at least one transcription repressor domain that reduces transcription of the allele in either or both of the sense and antisense directions. Reducing the level of mutant C9orf72 transcripts in neurons by introducing the ZFP-TFs into the nervous system (e.g., brain and spinal cord) of a patient is expected to inhibit (e.g., reduce or stop) the formation of disease-causing cytotoxic materials within the cells. The present ZFP-TFs can be used for treatment, including prevention and alleviation, of C9orf72-related disorders such as ALS and C9FTD.

Disclosed herein are methods and compositions for diagnosing, preventing and/or treating ALS and FTD. In particular, provided herein are methods and compositions for modifying (e.g., modulating expression of) specific genes so as to treat these diseases including the use of engineered transcription factor repressors and nucleases. In some embodiments, modulation of expression comprises modulating both sense and/or antisense expression.

Thus, described herein are methods (in vivo, ex vivo and/or in vitro) of repressing sense and/or anti-sense transcription of the repeat expanded mutant alleles of the C9orf72 gene in a cell (e.g., a neuron). The methods comprise treating the cells with one or more repressors of the mutant C9orf72 gene alleles, the one or more repressors comprising a transcriptional repression domain and a DNA-binding domain that binds to a target site in the mutant C9orf72 gene alleles. The repressor(s) can comprise one or more zinc finger protein transcription factors (ZFP-TF comprising a ZFP DNA-binding domain), one or more TAL-effector domain transcription factors (TALE-TF comprising a TAL-effector domain DNA-binding domain) and/or one or more CRISPR/Cas transcription factor systems (comprising a single guide RNA DNA-binding domain). In certain embodiments, two or more different repressors (e.g., one or more pharmaceutical compositions comprising the two or more different repressors) are used. In certain embodiments, the C9orf72 gene comprises a mutant allele comprising one or more ($G_4C_2$) repeats, optionally wherein the target site bound by the DNA-binding domain of the repressor is within the one or more ($G_4C_2$) repeats. Therefore, the invention provides use of one or more ZFP-TF, TALE-TF or CRISPR/Cas TF repressors (e.g., formulated into one or more pharmaceutical compositions comprising the one or more repressors) that bind to a mutant C9orf72 expanded allele comprising one or more ($G_4C_2$) repeats for repressor of sense and/or antisense transcription (e.g., by 50%, 70% or more as compared to an untreated cell/subject) in a subject in need thereof (e.g., a subject with ALS and/or FTD where the disease is treated and/or the symptoms ameliorated). In certain embodiments, sense and/or antisense transcription is not repressed to more than 90% of normal (control) levels. In certain embodiments, both antisense and sense transcription are repressed at the same or different levels (e.g., antisense and sense transcription are similarly repressed); antisense transcription is repressed more than sense transcription or sense transcription is repressed more than antisense transcription. In certain embodiments, specific sense transcripts are repressed while others are not. In some embodiments, transcription from the promoter in the 1b intron segment is not repressed while transcription from the promoter in the 1a intron and antisense transcripts are repressed. In certain embodiments, transcripts comprising the expanded repeat are selectively repressed (e.g., antisense transcription is repressed, sense transcription from the 1a promoter is repressed and/or sense transcription from the 1b promoter is not repressed). In certain embodiments, one or more ZFP-TF repressors comprising the recognition helix regions as shown in Table 1 are used in the methods and uses described herein, optionally in combination with one or more different repressors (e.g., additional different ZFP-TFs, for example, one or more additional ZFP-TFs comprising a ZFP as shown in Table 1). In certain embodiments, one or more of the repressors are administered to the cell using one or more non-viral vectors (e.g., as mRNA) and/or viral vectors (e.g., AAV such as AAV2/9). Multiple copies of the one or more modulators (e.g., repressors) may be administered using the same or different modalities (e.g., mRNA and/or AAV). In certain embodiments, the same or different modalities may be used to deliver one or more different modulators (e.g., repressors). In vivo methods and uses in live subjects (e.g., humans) can involve administration (e.g., of one or more pharmaceutical compositions comprising the repressors and/or polynucleotides encoding the repressor) by any suitable means, including but not limited to, intracerebroventricular, intrathecal, intracranial, retro-orbital (RO), intravenous, intranasal and/or intracisternal intravenously. Brain administration may be unilateral or bilateral (e.g., to the hippocampus). Any amount (dosage) may be administered, for example 1E10 to 1E13 (e.g., 6E11) vg/hemisphere. In any of the methods and uses described herein, ALS and/or FTD is treated (and/or one or more symptoms of these diseases are treated) in the subject.

Provided herein is a genetic modulator of a C9orf72 gene, the modulator comprising a DNA-binding domain (e.g., zinc finger protein (ZFP), a TAL-effector domain protein (TALE) or single guide RNA) that binds to a target site of at least 12 nucleotides in the C9orf72 gene; and a transcriptional regulatory domain (e.g., repression domain). One or more polynucleotides (e.g., viral or nonviral gene delivery vehicle, for example, an AAV vector) encoding one or more of the genetic modulators described herein are also provided. In other aspects, described herein are pharmaceutical compositions comprising one or more polynucleotides and/or one or more gene delivery vehicles as provided herein. In some embodiments, the genetic modulator comprises a regulator domain, the genetic modulator (and pharmaceutical composition comprising the one or more genetic modulators or polynucleotides encoding the one or more genetic modulators) modulates (e.g., represses or activates) the expression of the C9orf72 gene. Sense and/or antisense strands of the gene may be bound and/or modulated. Also provided herein are isolated cells (including cell populations) comprising one or more genetic modulators; one or more polynucleotides; one or more gene delivery vehicles; and/or one or more pharmaceutical compositions as described herein. Methods and uses for modulating expressing (e.g., repressing) a C9orf72 gene in a cell (in vitro, in vivo or ex vivo) are also provided, the methods comprising administering (via any method including but not limited to intracerebroventricular, intrathecal, intracranial, retro-orbital (RO), intravenous or intracisternal) one or more genetic modulators; one or more polynucleotides; one or more gene delivery vehicles; and/or one or more pharmaceutical compositions as described herein to the cells. The methods can be used for the treatment and/or prevention of amyotrophic lateral sclerosis (ALS) or frontotemporal dementia (FTD) in a subject. Uses of one or more one or more genetic modulators; one or more polynucleotides; one or more gene delivery vehicles; and/or one or more pharmaceutical compositions for the treatment and/or prevention of ALS or FTD in a subject are also provided. Also provided is a kit comprising one or more genetic modulators; one or more polynucleotides; one or more gene delivery vehicles; and/or one or more pharmaceutical compositions as described herein and, optionally, instructions for use.

Thus, in one aspect, engineered (non-naturally occurring) genetic modulators (e.g., repressors) of one or more genes are provided. These genetic modulators may comprise systems (e.g., zinc finger proteins, TAL effector (TALE) proteins or CRISPR/dCas-TF) that modulate (e.g., repress) expression of an allele. Expression of wild-type and/or mutant alleles may be modulated together or separately. In certain embodiments, the modulation of the mutant allele is at a greater level than the wild-type allele (e.g., wild-type allele is repressed no more than 50% of normal but a mutant allele is repressed by at least 70% as compared to untreated control). In some embodiments, modulation of expression may comprise modulating both sense and antisense transcripts of the C9orf72 gene. In some embodiments, modulation of expression may predominantly modulate sense transcripts, while in other embodiments, modulation of expression may predominantly modulate antisense transcripts.

An expansion mutation in a C9orf72 allele leads to expression of both a sense and anti-sense RNA product associated with ALS and FTD, so in one embodiment, provided are engineered transcription factors designed to repress expression of these mutant C9orf72 alleles for the treatment of ALS or FTD. Engineered zinc finger proteins or TALEs are non-naturally occurring zinc finger or TALE proteins whose DNA binding domains (e.g., recognition helices or RVDs) have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). In certain embodiments, the ZFP-TFs comprise a ZFP having the recognition helix regions as shown in a single row of Table 1. Similarly, any of the TALE proteins described herein may include any number of TALE RVDs. In some embodiments, at least one RVD has non-specific DNA binding. In some embodiments, at least one recognition helix (or RVD) is non-naturally occurring. In certain embodiments, the TALE-TF comprises a TALE that binds to at least 12 base pairs of a target site as shown in Table 1. A CRISPR/Cas-TF includes a single guide RNA that binds to a target sequence. In certain embodiments, the engineered transcription factor binds to (e.g., via a ZFP, TALE or sgRNA DNA binding domain) an at least 9-12 base pair target site in a disease associated gene, for example a target site comprising at least 9-20 base pairs (e.g., 9, 10, 11, 12, 13, 14, 15, 16, 17, 18, 19, 20 or more), including contiguous or non-contiguous sequences within these target sites (e.g., a target site as shown in Table 1). In certain embodiments, the genetic modulator comprises a DNA-binding molecule (ZFP, TALE, single guide RNA) as described herein operably linked to a transcriptional repression domain (to form a genetic repressor).

Thus, the zinc finger proteins (ZFPs), Cas protein of a CRISPR/Cas system or TALE proteins as described herein can be placed in operative linkage with a regulatory domain (or functional domain) as part of a fusion molecule. The functional domain can be, for example, a transcriptional activation domain, a transcriptional repression domain and/or a nuclease (cleavage) domain. By selecting either an activation domain or repression domain for use with the DNA-binding molecule, such molecules can be used either to activate or to repress gene expression. In certain embodiments, the functional or regulatory domains can play a role in histone post-translational modifications. In some instances, the domain is a histone acetyltransferase (HAT), a histone deacetylase (HDAC), a histone methylase, or an enzyme that sumolyates or biotinylates a histone or other enzyme domain that allows post-translation histone modification regulated gene repression (Kousarides, (2007) Cell 128:693-705). In some embodiments, a molecule comprising a ZFP, dCas or TALE targeted to a gene (e.g., C9orf72) as described herein fused to a transcriptional repression domain that can be used to down-regulate gene expression is provided. In some embodiments, the methods and compositions of the invention are useful for treating eukaryotes. In certain embodiments, the activity of the regulatory domain is regulated by an exogenous small molecule or ligand such that interaction with the cell's transcription machinery will not take place in the absence of the exogenous ligand. Such external ligands control the degree of interaction of the ZFP-TF, CRISPR/Cas-TF or TALE-TF with the transcription machinery. The regulatory domain(s) may be operatively linked to any portion(s) of one or more of the ZFPs, dCas or TALEs, including between one or more ZFPs, dCas or TALEs, exterior to one or more ZFPs, dCas or TALEs and any combination thereof. In preferred embodiments, the regulatory domain results in a repression of gene expression of the targeted gene (e.g., C9orf72). Any of the fusion proteins described herein may be formulated into a pharmaceutical composition.

In some embodiments, the artificial regulator binds to a promoter region upstream (e.g., 5' of) of the transcriptional start site (TSS) of the gene. In some embodiments, the artificial regulator binds to a region downstream of the TSS. In preferred embodiments, the artificial regulator preferentially binds to an expanded repeat region in a C9orf72 gene. In some embodiments, binding of the artificial regulator to the C9orf72 gene represses expression of the promoter in the 1a intron. In some embodiments, binding of the artificial regulator to the C9orf72 gene represses expression of the promoter in the 1b intron. In some embodiments, binding of the artificial regulator represses expression from the 1a promoter and an antisense promoter, but does not repress the 1b promoter. See also FIGS. 1B and 1C.

In some embodiments, the methods and compositions of the invention include use of two or more fusion molecules as described herein, for instance two or more C9orf72 modulators (artificial transcription factors). The two or more fusion molecules may bind to different target sites and comprise the same or different functional domains. Alternatively, the two or more fusion molecules as described herein may bind to the same target site but include different functional domains. In some instances, three or more fusion molecules are used, in others, four or more fusion molecules are used, while in others, 5 or more fusion molecules are used. In some embodiments, the two or more, three or more, four or more, or five or more fusion molecules (or components thereof) are delivered to the cell as nucleic acids. In preferred embodiments, the fusion molecules cause a repression of the expression of the targeted gene. In some embodiments, two fusion molecules are given at doses where each molecule is active on its own but in combination the repression activity is additive. In some embodiments, two fusion molecules are given at doses where neither is active on its own, but in combination, the repression activity is synergistic.

In yet another aspect, a polynucleotide encoding any of the DNA binding domains described herein is provided.

In some embodiments, the polynucleotide encoding the DNA binding protein is an mRNA. In some aspects, the mRNA may be chemically modified (e.g., Kormann et al., (2011) *Nature Biotechnology* 29(2):154-7). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In yet another aspect, a gene delivery vector comprising any of the polynucleotides (e.g., repressors) as described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). In certain embodiments, the AAV vector is an AAV2, AAV6, AAV8 or AAV9 vector or pseudotyped AAV vector such as AAV2/8, AAV2/5, AAV2/9 and AAV2/6. In some embodiments, the AAV vector is an AAV vector capable of crossing the blood-brain barrier (e.g. U.S. Patent Publication No. 2015/0079038). In other embodiments, the AAV is a self-complementary AAV (sc-AAV) or single stranded (ss-AAV) molecule. Also provided herein are adenovirus (Ad) vectors, LV or adenovirus associate viral vectors (AAV) comprising a sequence encoding at least one nuclease (ZFN or TALEN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments, the vector is pseudo-typed with a VSV-G envelope, or with other envelopes.

Additionally, pharmaceutical compositions comprising the nucleic acids, and/or fusions such as artificial transcription factors (e.g., ZFPs, Cas or TALEs or fusion molecules comprising the ZFPs, Cas or TALEs) are also provided. For example, certain compositions include a nucleic acid comprising a sequence that encodes one of the ZFPs, Cas or TALEs described herein operably linked to a regulatory sequence, combined with a pharmaceutically acceptable carrier or diluent, wherein the regulatory sequence allows for expression of the nucleic acid in a cell. In certain embodiments, the ZFPs, Cas, CRISPR/Cas or TALEs encoded modulate a wild-type and/or mutant allele. In some embodiments, the mutant allele is preferentially modulated, e.g., is repressed, more than the wild-type allele. In some embodiments, pharmaceutical compositions comprise ZFPs, CRISPR/Cas or TALEs that preferentially modulate a mutant allele and ZFPs, CRISPR/Cas or TALEs that modulate a neurotrophic factor. Protein based compositions include one of more ZFPs, CRISPR/Cas or TALEs as disclosed herein and a pharmaceutically acceptable carrier or diluent.

In yet another aspect also provided is an isolated cell comprising any of the proteins, fusion molecules, polynucleotides and/or compositions as described herein. The isolated cell may be used for non-therapeutic uses such as the provision of cell or animal models for diagnostic and/or screening methods and/or for therapeutic uses such as ex vivo cell therapy.

In yet another aspect, also provided are pharmaceutical compositions comprising one or more genetic modulators, one or more polynucleotides (e.g., gene delivery vehicles) and/or one or more (e.g., a population of) isolated cells as described herein. In certain embodiments, the pharmaceutical composition comprises two or more genetic modulators. For example, certain compositions include a nucleic acid comprising a sequence that encodes one or more genetic modulators of one of the genes associated with the rare disease (e.g., C9orf72) as described herein. In certain embodiments, the genetic modulator(s) (e.g., comprising ZFPs, Cas or TALEs described herein) are operably linked to a regulatory sequence, combined with a pharmaceutically acceptable carrier or diluent, where the regulatory sequence allows for expression of the nucleic acid in a cell. In certain embodiments, the ZFPs, CRISPR/Cas or TALEs encoded are specific for a mutant or wildtype allele (e.g., C9orf72). In some embodiments, pharmaceutical compositions comprise ZFP-TFs, CRISPR/Cas-TFs or TALE-TFs that modulate a mutant and/or wildtype allele (e.g., C9orf72), including TFs that preferentially modulate (e.g., repress at greater levels) the mutant allele as compared to the wild-type allele. Protein-based compositions include one of more genetic modulators as disclosed herein and a pharmaceutically acceptable carrier or diluent. In certain embodiments, the compositions comprising two or more genetic modulators (carried on the same or different type of vector, for example on AAV vectors) are used, optionally wherein one of the genetic modulators comprises a ZFP-TF repressor comprising a ZFP designated 74949, 74978, 75027 or 75109.

The invention also provides methods and uses for repressing gene expression in a subject in need thereof (e.g., a subject with a rare disease as described herein), including by providing to the subject one or more polynucleotides, one or more gene delivery vehicles, and/or a pharmaceutical composition as described herein. In certain embodiments, the compositions described herein are used to repress mutant C9orf72 expression in the subject, including for treatment and/or prevention of ALS or FTD. The compositions described herein repress gene expression for sustained periods of time (4 weeks, 3 months, 6 months to year or more) in the brain (including but not limited to the frontal cortical lobe including but not limited to the prefrontal cortex, parietal cortical lobe, occipital cortical lobe, temporal cortical lobe including but not limited to the entorhinal cortex, hippocampus, brain stem, striatum, thalamus, midbrain, cerebellum) and spinal cord (including but not limited to lumbar, thoracic and cervical regions). The compositions described herein may be provided to the subject by any administration means, including but not limited to, intracerebroventricular, intrathecal, intracranial, intravenous, orbital (retro-orbital (RO)), intranasal and/or intracisternal administration. Kits comprising one or more of the compositions (e.g., genetic modulators, polynucleotides, pharmaceutical compositions and/or cells) as described herein as well as instructions for use of these compositions are also provided.

In another aspect, provided herein are methods for treating and/or preventing a CNS (e.g., ALS and/or FTD) using the methods and compositions described herein. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations comprising an artificial transcription factor (e.g., ZFP-TF, TALE-TF, or dCas-TF). Administration of compositions as described herein (proteins, polynucleotides, cells and/or pharmaceutical compositions comprising these proteins, polynucleotides and/or cells) result in a therapeutic (clinical) effect, including, but not limited to, amelioration or elimination of any the clinical symptoms associate with ALS and/or FTD as well as an increase in function and/or number of CNS cells (e.g., neurons, astrocytes, myelin, etc.). In certain embodiments, the compositions and methods described herein reduce expression of sense and/or antisense transcripts for a target gene (e.g., C9orf72), as compared to controls not receiving the artificial repressors as described herein, by at least 30% or 40%, e.g., by at least 50%, at least 70%, at least 80%, at least 90%, at least 95%, or greater that 95%. In some embodiments, at least 50% reduction is achieved. In certain embodiments, the artificial repressor preferentially represses a mutant allele (for example, an expanded allele) as compared to a wild-type allele, for example by at least 20% (e.g., represses the wild-type allele no more than 50% and the mutant allele by at least 70%). In some embodiments, the repressor preferentially represses a sense transcript on a mutant allele, while in other embodiments, the repressor preferentially represses an antisense transcript on a mutant allele. In some embodiments, the repressor represses the sense and antisense transcripts on a mutant allele.

In a still further aspect, described here is a method of delivering a gene repressor to the brain of the subject using a viral or non-viral vector. In certain embodiments, the viral vector is an AAV9 vector. Delivery may be to any brain region, for example, the hippocampus or entorhinal cortex by any suitable means including via the use of a cannula. Any AAV vector that provides widespread delivery of the genetic modulator (e.g., repressor) to brain of the subject, including via anterograde and retrograde axonal transport to brain regions not directly administered the vector (e.g., delivery to the putamen results in delivery to other structures such as the cortex, substantia nigra, thalamus, etc.). In certain embodiments, the subject is a human and in other embodiments, the subject is a non-human primate. The administration may be in a single dose, or in a series of doses given at the same time, or in multiple administrations (at any timing between administrations).

Thus, in other aspects, described herein is a method of preventing and/or treating a disease (e.g., ALS and/or FTD) in a subject, the method comprising administering a repressor of a gene to the subject using AAV. In certain embodiments, the repressor is administered to the CNS (e.g., hippocampus and/or entorhinal cortex) or PNS (e.g., spinal cord/fluid) of the subject. In other embodiments, the repressor is administered intravenously. In certain embodiments, described herein is a method of preventing and/or treating ALS or FTD in a subject, the method comprising administering a repressor of a C9orf72 allele (wild-type and/or mutant) to the subject using one or more AAV vectors. In certain embodiments, the AAV encoding the genetic modulator is administered to the CNS (brain and/or CSF) via any delivery method including but not limited to, intracerebroventricular, intrathecal, intracranial, intravenous, intranasal, retro-orbital, or intracisternal delivery. In other embodiments, the AAV encoding the repressor is administered directly into the parenchyma (e.g., hippocampus and/or entorhinal cortex) of the subject. In other embodiments, the AAV encoding the repressor is administered intravenously (IV). In any of the methods described herein, the administering may be done once (single administration) or may be done multiple times (with any time between administrations) at the same or different doses per administration.

When administered multiple times, the same or different dosages and/or delivery vehicles of modes of administration may be used (e.g., different AAV vectors administered IV and/or ICV). The methods include methods of reducing the loss of muscle function, the loss of physical coordination, stiffening of muscles, muscle spasms, loss of speech functions, difficulty of swallowing, cognitive impairment, method of reducing loss of motor function, and/or methods of reducing loss of one or more cognitive functions in ALS subjects, all in comparison with a subject not receiving the method, or in comparison to the subject themselves prior to receiving the methods. Thus, the methods described herein result in reduction in biomarkers and/or symptoms of rare diseases such as ALS or FTD, including one or more the following: the loss of muscle function, the loss of physical coordination, stiffening of muscles, muscle spasms, loss of speech functions, difficulty of swallowing, cognitive impairment, changes in blood and/or cerebral spinal fluid chemistries associated with ALS, including G-CSF, IL-2, IL-15, IL-17, MCP-1, MIP-1α, TNF-α, and VEGF levels (see Chen et al., *Front Immunol.* (2018) 9:2122), and/or other biomarkers known in the art. In certain embodiments, the methods may further comprise administering one or more genetic repressors of tau (MAPT), for example in subjects with FTD. See, e.g., U.S. Patent Publication No. 2018/0153921.

In any of the methods described herein, the repressor of the targeted allele may be a ZFP-TF, for example a fusion protein comprising a ZFP that binds specifically to an allele and a transcriptional repression domain (e.g., KOX, KRAB, etc.). In other embodiments, the repressor of the targeted allele may be a TALE-TF, for example a fusion protein comprising a TALE polypeptide that binds specifically to a gene allele and a transcriptional repression domain (e.g., KOX, KRAB, etc.). In some embodiments, the targeted allele repressor is a CRISPR/Cas-TF where the nuclease domains in the Cas protein have been inactivated such that the protein no longer cleaves DNA. The resultant Cas RNA-guided DNA binding domain is fused to a transcription repressor (e.g., KOX, KRAB, etc.) to repress the targeted allele. In some embodiments, the engineered transcription factor is able to repress expression of a mutated allele but not the wildtype allele. In further embodiments, the DNA binding molecule preferentially recognizes a hexameric GGGGCC (SEQ ID NO:1) expansion.

In some embodiments, the sequence encoding a genetic repressor as described herein (e.g., ZFP-TF, TALE-TF or CRISPR/Cas-TF) is inserted (integrated) into the genome while in other embodiments the sequence encoding the repressor is maintained episomally. In some instances, the nucleic acid encoding the TF fusion is inserted (e.g., via nuclease-mediated integration) at a safe harbor site comprising a promoter such that the endogenous promoter drives expression. In other embodiments, the repressor (TF) donor sequence is inserted (via nuclease-mediated integration) into a safe harbor site and the donor sequence comprises a promoter that drives expression of the repressor. In some embodiments, the promoter sequence is broadly expressed while in other embodiments, the promoter is tissue or cell/type specific. In preferred embodiments, the promoter sequence is specific for neuronal cells. In other embodiments, the promoter sequence is specific for muscle cells. In some embodiments, the promoter chosen is characterized in that it has low expression. Non-limiting examples of useful promoters include the neural specific promoters NSE, synapsin, CAMKiia and MECPs. Non-limiting examples of ubiquitous promoters include CMV, CAG and Ubc. Further embodiments include the use of self-regulating promoters as described in U.S. Patent Publication No. 2015/0267205. Further embodiments include the use of self-regulating promoters as described in U.S. Patent Publication No. 2015/0267205.

In any of the methods described herein, the method can yield about 50% or greater, 55% or greater, 60% or greater, 65% or greater, about 70% or greater, about 75% or greater, about 85% or greater, about 90% or greater, about 92% or greater, or about 95% or greater repression, 98% or greater, or 99% or greater of the target alleles (e.g., mutant or wild-type C9orf72) in one or more neurons of a subject (e.g., a subject with ALS). In certain embodiments, expression of the wild-type allele is repressed no more than 50% in the subject (as compared to untreated subjects) while the mutant allele is repressed at least 70% (70% or any value thereabove) in the subject (as compared to untreated subjects). In some embodiments, the expression of an antisense promoter is repressed at least 70%. In certain embodiments, the expression of the antisense promoters found in the region of the C9orf72 intron 1a, 1b and/or 1c is repressed at least 70% while the expression of the sense promoter in the region of the C9orf72 intron 1b is repressed no more than 50%.

In any of the methods described herein, the regulator (e.g., repressor or activator) may be delivered to the subject as a protein, polynucleotide or any combination of protein and polynucleotide. In certain embodiments, the one or more repressor are delivered using an AAV vector. In other embodiments, at least one component of the regulator (e.g., sgRNA of a CRISPR/Cas system) is delivered as an RNA form. In other embodiments, the regulator(s) is(are) delivered using a combination of any of the expression constructs described herein, for example one repressor (or portion thereof) on one expression construct (AAV9) and one repressor (or portion thereof) on a separate expression construct (AAV or other viral or non-viral construct).

Furthermore, in any of the methods described herein, the regulator (e.g., repressor) can be delivered to a cell (ex vivo or in vivo) at any concentration (dose) that provides the desired effect. In some embodiments, the regulator is delivered using an adeno-associated virus (AAV) vector at 10,000-500,000 vector genome/cell (or any value therebetween). In certain embodiments, the regulator is delivered using a lentiviral vector at MOI between 250 and 1,000 (or any value therebetween). In other embodiments, the regulator is delivered using a plasmid vector at 0.01-1,000 ng/100,000 cells (or any value therebetween). In other embodiments, the repressor is delivered as mRNA at 150-1,500 ng/100,000 cells (or any value therebetween). Furthermore, for in vivo uses, in any of the methods described herein, the genetic modulator(s) (e.g., repressors) can be delivered at any concentration (dose) that provides the desired effect in a subject in need thereof. In some embodiments, the repressor is delivered using an adeno-associated virus (AAV) vector at 10,000-500,000 vector genome/cell (or any value therebetween). In certain embodiments, the repressor is delivered using a lentiviral vector at MOI between 250 and 1,000 (or any value therebetween). In other embodiments, the repressor is delivered using a plasmid vector at 0.01-1,000 ng/100,000 cells (or any value therebetween). In other embodiments, the repressor is delivered as mRNA at 0.01-3000 ng/number of cells (e.g., 50,000-200,000 (e.g., 100,000) cells (or any value therebetween). In other embodiments, the repressor is delivered using an adeno-associated virus (AAV) vector at a fixed volume of 1-300 µL to the brain parenchyma at 1E11-1E14 Vg/mL. In other embodiments, the repressor is delivered using an adeno-associated virus (AAV) vector at a fixed volume of 0.5-10 mL to the CSF at 1E11-1E14 Vg/mL.

In any of the methods described herein, the method can yield about 50% or greater, 55% or greater, 60% or greater, 65% or greater, about 70% or greater, about 75% or greater, about 85% or greater, about 90% or greater, about 92% or greater, or about 95% or greater modulation (e.g., repression) of the targeted allele(s) in one or more cells of the subject. In some embodiments, wild-type and mutant alleles are modulated differently, for example the mutant allele is preferentially modified as compared to the wild-type allele (e.g., mutant allele repressed by at least 70% and the wild-type allele is repressed by no more than 50%).

In any of the methods described herein, the method can yield about 50% or greater, 55% or greater, 60% or greater, 65% or greater, about 70% or greater, about 75% or greater, about 85% or greater, about 90% or greater, about 92% or greater, or about 95% or greater modulation (e.g., repression) of the antisense expression of the targeted allele(s) in one or more cells of the subject. In some embodiments, sense expression and antisense expression in the mutant alleles are modulated differently, for example expression of the antisense transcripts are preferentially modulated as compared to expression of the sense transcripts in the mutant allele (e.g., antisense expression is repressed by at least 70% and sense expression is repressed by no more than 50%).

In further aspects, the transcription factors as described herein, such as transcription factors comprising one or more of a zinc finger protein (ZFP-TFs), a TALEs (TALE-TF), and a CRISPR/Cas-TFs for example, ZFP-TFs, TALE-TFs or CRISPR/Cas-TFs, are used to repress expression of a mutant and/or wildtype allele (e.g., C9orf72) in of the brain (e.g., neuron), of a subject. The repression can be about 50% or greater, 55% or greater, 60% or greater, 65% or greater, 70% or greater, about 75% or greater, about 85% or greater, about 90% or greater, about 92% or greater, or about 95% or greater repression of the targeted alleles in the one or more cells of the subject as compared to untreated (wild-type) cells of the subject. In certain embodiments, repression of the wild-type allele is not more than 50% (as compared to untreated cells or subjects) and repression of the mutant (diseased or isoform variant) is at least 70% (as compared to untreated cells or subjects). In certain embodiments, antisense transcription is completely (fully) repressed. In certain embodiments, repression of a sense transcript is not more than 50% (as compared to untreated cells or subjects) and repression of the antisense transcript is at least 70% (as compared to untreated cells or subjects). In certain embodiments, the targeted-modulating transcription factor can be used to achieve one or more of the methods described herein.

Thus, described herein are methods and compositions for modulating expression of genes associated with the rare disorders disclosed herein, including repression with or without expression of an exogenous sequence (such as an artificial TF). The compositions and methods can be for use in vitro (e.g., for the provision of cells for the study of the target gene via its modulation; for drug discovery; and/or to make transgenic animals and animal models), in vivo or ex vivo, and comprise administering an artificial transcription factor or nuclease that includes a DNA-binding molecule targeted to the gene associated with the rare disease, optionally in the case of a nuclease with a donor that is integrated into the gene following cleavage by the nuclease. In some embodiments, the donor gene (transgene) is maintained extrachromosomally in a cell. In certain embodiments, the cell is in a patient with the disease. In other embodiments, the cell is modified by any of the methods described herein, and the modified cell is administered to a subject in need thereof (e.g., a subject with the rare disease). Genetically modified cells (e.g., stem cells, precursor cells, T cells, muscle cells, etc.) comprising a genetically modified gene (e.g., an exogenous sequence) are also provided, including cells made by the methods described herein. These cells can be used to provide therapeutic protein(s) to a subject with the rare disease, for example, by administering the cell(s) to a subject in need thereof or, alternatively, by isolating the protein produced by the cell and administering the protein to the subject in need thereof (enzyme replacement therapy).

Also provided is a kit comprising one or more of the genetic modulators (e.g., repressors) and/or polynucleotides comprising components of and/or encoding the target-modulators (or components thereof) as described herein. The kits may further comprise cells (e.g., neurons or muscle cells), reagents (e.g., for detecting and/or quantifying a protein, for example in CSF) and/or instructions for use, including the methods as described herein.

The present methods and compositions are further described in detail below.

I. Zinc-Finger Protein Transcription Factors

The present ZFP-TFs are fusion proteins containing a DNA-binding zinc finger protein (ZFP) domain and a transcription repressor domain, wherein the two domains may be associated with each other by a direct peptidyl linkage or a peptide linker, or by dimerization (e.g., through a leucine zipper, a STAT protein N-terminal domain, or an FK506 binding protein). As used herein, a "fusion protein" refers to a polypeptide with covalently linked domains as well as a complex of polypeptides associated with each other through non-covalent bonds. The transcription repressor domain can be associated with the ZFP domain at any suitable position, including the C- or N-terminus of the ZFP domain.

In some embodiments, the present ZFP-TFs repress transcription of a human mutant C9orf72 gene by 45% or more (e.g., by 50%, 60%, 70%, 80%, 90%, or 95% or more). In some embodiments, two or more of the present ZFP-TFs are used concurrently in a patient, where the ZFP-TFs bind to different DNA motifs in the sense and/or antisense strands of the expanded C9orf72 region, so as to achieve optimal repression of mutant C9orf72 transcription.

A. Targets of the ZFP Domains

Figure 1B:
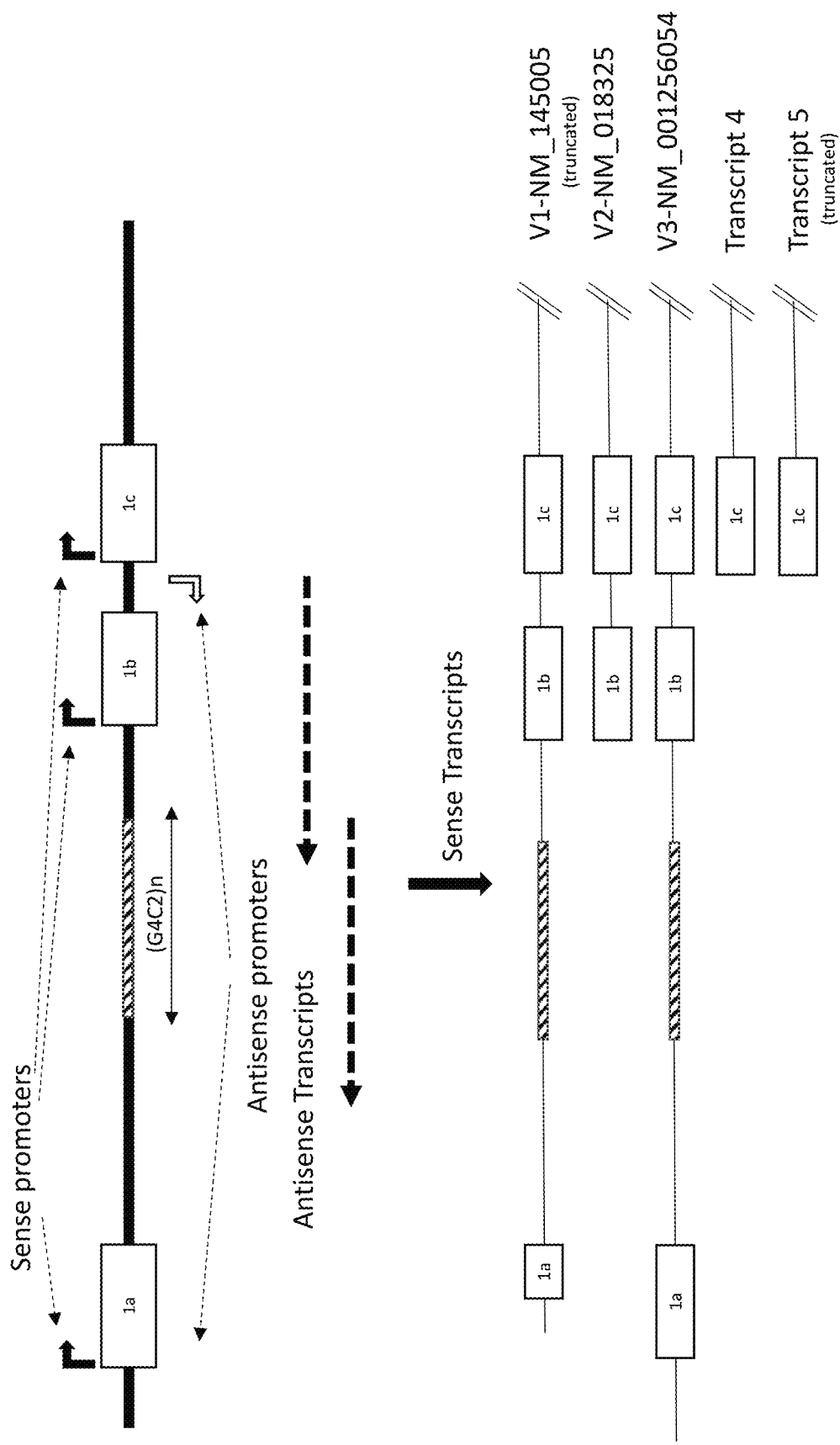
Figure 1C:
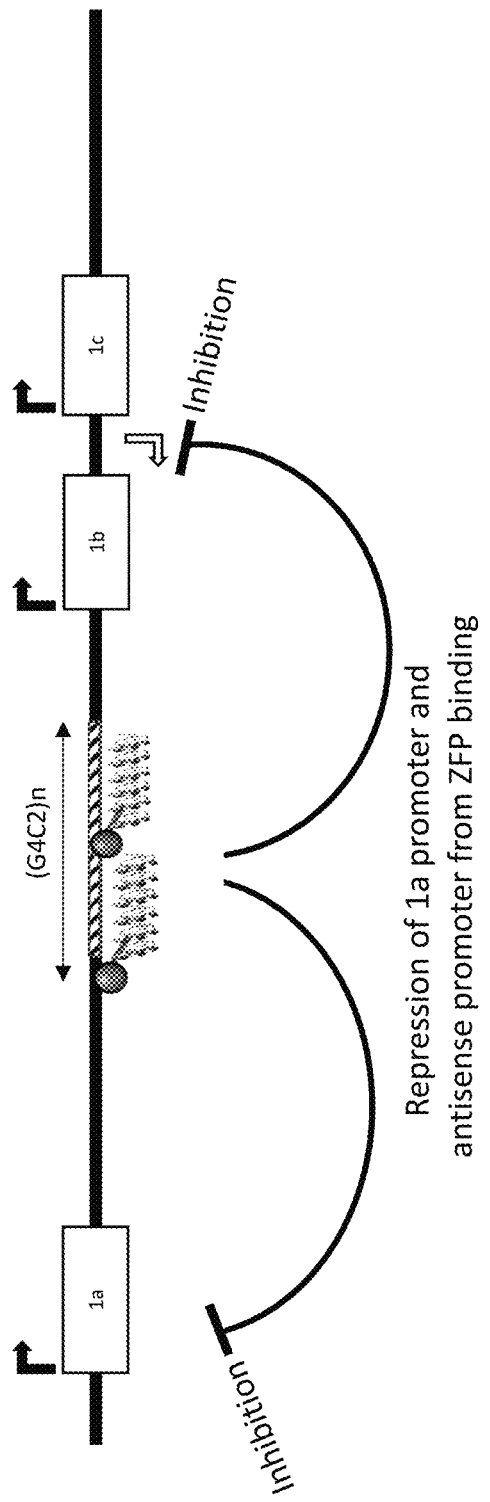

The ZFP domains of the present fusion proteins bind preferentially to the expanded region in a mutant human C9orf72 gene allele. The human C9orf72 gene is located at the short (p) arm of chromosome 9 at position 21.2 (9p21.2). It spans base pairs 27,546,546 to 27,573,866 on the chromosome. The genomic structure of human C9orf72 is shown in FIG. 1A. The DNA-binding ZFP domain of a ZFP-TF directs the fusion protein to the expanded repeat region of the mutant C9orf72 gene and brings the transcription repressor domain of the fusion protein to the target region. The repressor domain then represses C9orf72 gene transcription by RNA polymerase.

In some embodiments, the target sequence in the expanded region is at least 8 bps in length. For example, the target sequence may be 8 bps to 40 bps in length, such as 12, 15, 16, 17, 18, 19, 20, 21, 24, 27, 30, 33, or 36 bps in length. In certain embodiments, the target sequence of the present ZFP-TFs is 12-20 (e.g., 12-18, 15-19, 15, 18, or 19) bps in length. In some embodiments, the target sequence comprises subsequences that are not contiguous.

The $G_4C_2$ repeats give rise to the following hexanucleotide DNA motifs in the sense and antisense strands of the gene:

Motifs in the sense C9orf72 strand:

(i) GGGGCC (SEQ ID NO: 1)

(ii) GGGCCG (SEQ ID NO: 2)

(iii) GGCCGG (SEQ ID NO: 3)

(iv) GCCGGG (SEQ ID NO: 4)

(v) CCGGGG (SEQ ID NO: 5)

(vi) CGGGGC (SEQ ID NO: 6)

Motifs in the antisense C9orf72 strand:

(vii) GGCCCC (SEQ ID NO: 7)

(viii) GCCCCG (SEQ ID NO: 8)

(ix) CCCCGG (SEQ ID NO: 9)

(x) CCCGGC (SEQ ID NO: 10)

(xi) CCGGCC (SEQ ID NO: 11)

(xii) CGGCCC (SEQ ID NO: 12)

In some embodiments, the target sequence of the present ZFP-TF comprises one or more (e.g., 2, 3, or 4) tandem repeats of these DNA motifs. In some embodiments, the target sequence consists of three tandem repeats of one of the motifs. In some embodiments, the target sequence comprises one or more (e.g., 2 or 3) tandem repeats of a motif plus a few (e.g., 1, 2, 3, 4, or 5) nucleotides from an upstream and/or downstream adjacent sequence (e.g., $CC(G_4C_2)_2GG$) (SEQ ID NO:75).

The target sequence may be on the sense strand of the gene, or the antisense strand of the gene. In certain embodiments, ZFP-TFs used in a patient bind both the sense and antisense strands of the mutant allele. To ensure targeting accuracy and to reduce off-target binding by the ZFP-TFs, the sequence of the selected C9orf72 target region preferably has less than 75% homology (e.g., less than 70%, less than 65%, less than 60%, or less than 50% homology) to sequences in other genes in the genome.

Other criteria for further evaluating target segments include the prior availability of ZFPs binding to such segments or related segments, ease of designing new ZFPs to bind a given target segment, and off-target binding risk.

B. Zinc Finger Protein Domains

A "zinc finger protein" or "ZFP" refers to a protein having DNA-binding domains that are stabilized by zinc. ZFPs bind to DNA in a sequence-specific manner. The individual DNA-binding domains are referred to as "fingers." A ZFP has at least one finger, each finger binds from two to four base pairs of DNA, typically three or four base pairs of DNA. Each zinc finger typically comprises approximately 30 amino acids and chelates zinc. An engineered ZFP can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers that bind the particular triplet or quadruplet sequence. See, e.g., ZFP design methods described in detail in U.S. Pat. Nos. 5,789,538; 5,925,523; 6,007,988; 6,013,453; 6,140,081; 6,200,759; 6,453,242; 6,534,261; 6,979,539; 8,586,526; 8,841,260; 8,956,828; and 9,234,016; and International Patent Publications WO 95/19431; WO 96/06166; WO 98/53057; WO 98/53058; WO 98/53059; WO 98/53060; WO 98/54311; WO 00/27878; WO 01/60970; WO 01/88197; WO 02/016536; WO 02/099084; and WO 03/016496.

The ZFP domain of the present ZFP-TFs may include at least three (e.g., four, five, six, seven, eight, nine, ten, eleven, twelve, thirteen, or more) zinc fingers. A ZFP domain having three fingers typically recognizes a target site that includes 9 to 12 nucleotides. A ZFP domain having four fingers typically recognizes a target site that includes 12 to 15 nucleotides. A ZFP domain having five fingers typically recognizes a target site that includes 15 to 18 nucleotides. A ZFP domain having six fingers can recognize target sites that include 18 to 21 nucleotides.

The target specificity of the ZFP domain may be improved by mutations to the ZFP backbone as described in, e.g., U.S. Pat. Pub. 2018/0087072. The mutations include those made to residues in the ZFP backbone that can interact non-specifically with phosphates on the DNA backbone but are not involved in nucleotide target specificity. In some embodiments, these mutations comprise mutating a cationic amino acid residue to a neutral or anionic amino acid residue. In some embodiments, these mutations comprise mutating a polar amino acid residue to a neutral or non-polar amino acid residue. In further embodiments, mutations are made at positions (−5), (−9) and/or (−14) relative to the DNA-binding helix. In some embodiments, a zinc finger may comprise one or more mutations at positions (−5), (−9) and/or (−14). In further embodiments, one or more zinc fingers in a multi-finger ZFP domain may comprise mutations at positions (−5), (−9) and/or (−14). In some embodiments, the amino acids at positions (−5), (−9) and/or (−14) (e.g., an arginine (R) or lysine (K)) are mutated to an alanine (A), leucine (L), Ser (S), Asp (N), Glu (E), Tyr (Y), and/or glutamine (Q). In some embodiments, the R residue at position (−5) is mutated to Q.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032 and 6,833,252; Belfort et al., *Nucleic Acids Res.* (1997) 25:3379-88; Dujon et al., *Gene* (1989) 82:115-8; Perler et al., *Nucleic Acids Res.* (1994) 22:1125-7; Jasin, *Trends Genet.* (1996) 12:224-8; Gimble et al., *J Mol Biol.* (1996) 263:163-80; Argast et al., *J Mol Biol.* (1998) 280:345-53; and the New England Biolabs catalogue.

In some embodiments, the present ZFP-TFs comprise one or more zinc finger domains. The domains may be linked together via an extendable flexible linker such that, for example, one domain comprises one or more (e.g., 4, 5, or 6) zinc fingers and another domain comprises additional one or more (e.g., 4, 5, or 6) zinc fingers. In some embodiments, the linker is a standard inter-finger linker such that the finger array comprises one DNA-binding domain comprising 8, 9, 10, 11 or 12 or more fingers. In other embodiments, the linker is an atypical linker such as a flexible linker. For example, two ZFP domains may be linked to a transcription repressor TF in the configuration (from N terminus to C terminus) ZFP-ZFP-TF, TF-ZFP-ZFP, ZFP-TF-ZFP, or ZFP-TF-ZFP-TF (two ZFP-TF fusion proteins are fused together via a linker).

In some embodiments, the ZFP-TFs are "two-handed," i.e., they contain two zinc finger clusters (two ZFP domains) separated by intervening amino acids so that the two ZFP domains bind to two discontinuous target sites. An example of a two-handed type of zinc finger binding protein is SIP1, where a cluster of four zinc fingers is located at the amino terminus of the protein and a cluster of three fingers is located at the carboxyl terminus (see Remacle et al., *EMBO J.* (1999) 18(18):5073-84). Each cluster of zinc fingers in these proteins is able to bind to a unique target sequence and the spacing between the two target sequences can comprise many nucleotides.

In alternative embodiments, the proteins that are similar to ZFP-TFs in function may be used in lieu of ZFP-TFs. For example, instead of ZFP domains, the transcription repressor fusion proteins may include a DNA-binding domain derived from a transcription activator like effectors (TALE) DNA-binding domain. See, e.g., U.S. Pat. Nos. 8,586,526 and 9,458,205; U.S. Patent Pubs. 2013/0196373 and 2013/0253040; WO 2010/079430; Schornack et al., *J Plant Physiol* (2006) 163(3):256-72); Kay et al., *Science* (2007) 318:648-51; Moscou and Bogdanove, *Science* (2009) 326: 1501; and Boch et al., *Science* (2009) 326:1509-12. In yet another example, the transcription repressor fusion proteins may include a DNA-binding domain that is a single-guide RNA of a CRISPR/Cas system. See, e.g., U.S. Patent Pub. 2015/0056705; Jinek et al., *Science* (2012) 337:816; Ramalingam et al., *Genome Biol.* (2013) 14:107; Hwang et al., (2013) *Nature Biotechnology* 31(3):227.

C. Transcription Repressor Domains

The present ZFP-TFs comprise one or more transcription repressor domains that dampen the transcription activity of the mutant C9orf72 allele. Non-limiting examples of transcription repressor domains are the KRAB domain of KOX1, KAP-1, MAD, FKHR, EGR-1, ERD, SID, TGF-beta-inducible early gene (TIEG), v-ERB-A, MBD2, MBD3, members of the DNMT family (e.g., DNMT1, DNMT3A, DNMT3B), Rb, and MeCP2. See, e.g., Bird et al., *Cell* (1999) 99:451-54; Tyler et al., *Cell* (1999) 99:443-46; Knoepfler et al., *Cell* (1999) 99:447-50; and Robertson et al., *Nature Genet.* (2000) 25:338-42. Additional exemplary repression domains include, but are not limited to, ROM2 and AtHD2A. See, e.g., Chem et al., *Plant Cell* (1996) 8:305-21; and Wu et al., *Plant J.* (2000) 22:19-27.

In some embodiments, the transcription repressor domain comprises a sequence from the Kruppel-associated box (KRAB) domain of the human zinc finger protein 10/KOX1

(ZNF10/KOX1) (e.g., GenBank No. NM_015394.4). An exemplary KRAB domain sequence is:

(SEQ ID NO: 13)
DAKSLTAWSR TLVTFKDVFV DFTREEWKLL DTAQQIVYRN

VMLENYKNLV SLGYQLTKPD VILRLEKGEE PWLVEREIHQ

ETHPDSETAF EIKSSV

Variants of this KRAB sequence may also be used so long as they have the same or similar transcription repressor function.

D. Peptide Linkers

The ZFP domain and the transcription repressor domain of the present ZFP-TFs and/or the zinc fingers within the ZFP domains may be linked through a peptide linker, e.g., a noncleavable peptide linker of about 5 to 200 amino acids (e.g., 5, 6, 7, 8, 9, 10, 11, 12, 13, 14, 15, 16, 17, 18, 19, 20 or more amino acids). Some preferred linkers are flexible amino acid sequences that are synthesized as a recombinant fusion protein. See, e.g., description above; and U.S. Pat. Nos. 6,479,626; 6,903,185; 7,153,949; 8,772,453; and 9,163,245; and WO 2011/139349. The proteins described herein may include any combination of suitable linkers. Non-limiting examples of linkers are DGGGS (SEQ ID NO:14), TGEKP (SEQ ID NO:15), LRQKDGERP (SEQ ID NO:16), GGRR (SEQ ID NO:17), GGRRGGGS (SEQ ID NO:18), LRQRDGERP (SEQ ID NO:19), LRQKDGGGSERP (SEQ ID NO:20), LRQKD($G_3$S)$_2$ERP (SEQ ID NO:21), TGSQKP (SEQ ID NO:22), LRQKDAARGS (SEQ ID NO:26), and LRQKDAARGSGG (SEQ ID NO:76).

In some embodiments, the peptide linker is 3 to 20 amino acid residues in length and is rich in G and/or S. Non-limiting examples of such linkers are $G_4S$-type linkers ("$G_4S$" disclosed as SEQ ID NO:23), i.e., linkers containing one or more (e.g., 2, 3, or 4) GGGGS (SEQ ID NO:23) motifs, or variations of the motif (such as ones that have one, two, or three amino acid insertions, deletions, and substitutions in the motif).

In some embodiments, the ZFP-TFs comprise nuclear localization signals (e.g., that from the SV40 medium T-antigen) and/or epitope tags (e.g., FLAG and hemagglutinin).

II. Expression of the ZFP-TFs

A ZFP-TF of the present disclosure may be introduced to a patient through a nucleic acid molecule encoding it. For example, the nucleic acid molecule is an RNA molecule, and the RNA molecule is introduced into the brain of the patient through injection of a composition comprising a lipid:nucleic acid complex (e.g., a liposome). Alternatively, the ZFP-TF may be introduced to the patient through a nucleic acid expression vector comprising a coding sequence for the ZFP-TF. The expression vectors may include expression control sequences such as promoters, enhancers, transcription signal sequences, and transcription termination sequences that allow expression of the coding sequences for the ZFP-TFs in the cells of the nervous system (e.g., central nervous system). In some embodiments, the expression vector remains present in the cell as a stable episome. In other embodiments, the expression vector is integrated into the genome of the cell.

In some embodiments, the promoter on the vector for directing the ZFP-TF expression in the brain is a constitutively active promoter or an inducible promoter. Suitable promoters include, without limitation, a Rous sarcoma virus (RSV) long terminal repeat (LTR) promoter (optionally with an RSV enhancer), a cytomegalovirus (CMV) promoter (optionally with a CMV enhancer), a CMV immediate early promoter, a simian virus 40 (SV40) promoter, a dihydrofolate reductase (DHFR) promoter, a β-actin promoter, a phosphoglycerate kinase (PGK) promoter, an EF1α promoter, a Moloney murine leukemia virus (MoMLV) LTR, a creatine kinase-based (CK6) promoter, a transthyretin promoter (TTR), a thymidine kinase (TK) promoter, a tetracycline responsive promoter (TRE), a hepatitis B virus (HBV) promoter, a human al-antitrypsin (hAAT) promoter, chimeric liver-specific promoters (LSPs), an E2 factor (E2F) promoter, the human telomerase reverse transcriptase (hTERT) promoter, a CMV enhancer/chicken β-actin/rabbit β-globin promoter (CAG promoter; Niwa et al., *Gene* (1991) 108(2):193-9), and an RU-486-responsive promoter. Neuron-specific promoters such as the synapsin I promoter, the calcium/calmodulin-dependent protein kinase II (CamKII) promoter, the methyl CpG-binding protein 2 (MeCP2) promoter, the choline acetyltransferase (ChAT) promoter, and the Calbindin (Calb) promoter may also be used. Astrocyte-specific promoters such as the glial fibrillary acidic protein (GFAP) promoter or the aldehyde dehydrogenase 1 family, member L1 (Aldh1L1) promoter may also be used. Oligodendrocyte-specific promoters such as the Olig2 promoter may also be used. In addition, the promoter may include one or more self-regulating elements whereby the ZFP-TF can bind to and repress its own expression level to a preset threshold. See U.S. Pat. No. 9,624,498.

Any method of introducing the nucleotide sequence into a cell may be employed, including but not limited to, electroporation, calcium phosphate precipitation, microinjection, cationic or anionic liposomes, liposomes in combination with a nuclear localization signal, naturally occurring liposomes (e.g., exosomes), or viral transduction.

For in vivo delivery of an expression vector, viral transduction may be used. A variety of viral vectors known in the art may be adapted for use in the present disclosure, for example, vaccinia vectors, adenoviral vectors, lentiviral vectors, poxyviral vectors, herpesviral vectors, adeno-associated viral (AAV) vectors, retroviral vectors, and hybrid viral vectors. In some embodiments, the viral vector used herein is a recombinant AAV (rAAV) vector. AAV vectors are especially suitable for central nervous system (CNS) gene delivery because AAVs infect both dividing and non-dividing cells and have very low immunogenicity, and the viral genomes exist as stable episomal structures for long term expression (Hadaczek et al., *Mol Ther*. (2010) 18:1458-61; Zaiss, et al., *Gene Ther*. (2008) 15:808-16). Any suitable AAV serotype may be used. For example, the AAV may be AAV1, AAV2, AAV3, AAV3b, AAV4, AAV5, AAV6, AAV7, AAV8, AAV8.2, AAV9, or AAVrh10, or of a pseudotype (e.g., AAV2/8, AAV2/5, AAV2/6, AAV2/9, or AAV2/6/9). See, e.g., U.S. Pat. Nos. 7,198,951 and 9,585,971.

In some embodiments, the expression vector is an AAV vector and is introduced to the target human cell by a recombinant AAV virion whose genome comprises the construct, including having the AAV Inverted Terminal Repeat (ITR) sequences on both ends to allow the production of the AAV virion in a production system such as an insect cell/baculovirus production system or a mammalian cell production system. The AAV may be engineered such that its capsid proteins have reduced immunogenicity or enhanced transduction ability in humans. In some embodiments, AAV9 is used. Viral vectors described herein may be produced using methods known in the art. Any suitable permissive or packaging cell type may be employed to produce the viral particles. For example, mammalian (e.g., 293) or insect (e.g., Sf9) cells may be used as the packaging cell line.

See also U.S. Pat. Nos. 6,309,634; 6,453,242; 6,503,717; 6,534,261; 6,599,692; 6,607,882; 6,689,558; 6,824,978; 6,933,113; 6,953,575; 6,979,539; 7,013,219; 7,163,824; 7,182,944; 8,309,355; 8,337,458; 8,586,526; 9,050,299; and 9,089,667 for methods of expressing therapeutic proteins, including ZFPs, in the nervous system of a patient in need thereof.

III. Pharmaceutical Applications

The present ZFP-TFs can be used to treat patients in need of downregulation of C9orf72 expression, especially downregulation of expression of mutant C9orf72 alleles. The patients suffer from, or are at risk of developing, C9orf72-related neurodegenerative diseases such as ALS and C9FTD. Patients at risk include those who are genetically predisposed, those who have suffered repeated brain injuries such as concussions, and those who have been exposed to environmental neurotoxins. The present disclosure provides a method of treating a C9orf72-related neurological disease (e.g., ALS and C9FTD) in a subject such as a human patient in need thereof, comprising introducing to the nervous system (e.g., CNS) of the subject a therapeutically effective amount (e.g., an amount that allows sufficient repression of the mutant C9orf72 allele expression) of the ZFP-TF (e.g., an rAAV vector expressing it). The term "treating" encompasses alleviation of symptoms, prevention of onset of symptoms, slowing of disease progression, improvement of quality of life, and increased survival.

The present disclosure provides a pharmaceutical composition comprising a viral vector such as an rAAV whose recombinant genome comprises an expression cassette for the ZFP-TFs. The pharmaceutical composition may further comprise a pharmaceutically acceptable carrier such as water, saline (e.g., phosphate-buffered saline), dextrose, glycerol, sucrose, lactose, gelatin, dextran, albumin, or pectin. In addition, the composition may contain auxiliary substances, such as, wetting or emulsifying agents, pH-buffering agents, stabilizing agents, or other reagents that enhance the effectiveness of the pharmaceutical composition. The pharmaceutical composition may contain delivery vehicles such as liposomes, nanocapsules, microparticles, microspheres, lipid particles, and vesicles.

The cells targeted by the therapeutics of the present disclosure are cells in the brain and/or the spinal cord, including, without limitation, a neuronal cell (e.g., a motor neuron, a sensory neuron, a dopaminergic neuron, a cholinergic neuron, a glutamatergic neuron, a GABAergic neuron, or a serotonergic neuron); a glial cell (e.g., an oligodendrocyte, an astrocyte, a pericyte, a Schwann cell, or a microglial cell); an ependymal cell; or a neuroepithelial cell. The brain regions targeted may be cortical regions, frontotemporal regions, the entorhinal cortex, the hippocampus, the cerebellum, the pons, and the medulla. These regions can be reached directly through intrahippocampal injection, intracerebral injection, intra-cisterna magna (ICM) injection, or more generally through intraparenchymal injection, intracerebroventricular (ICV) injection, intrathecal injection, or intravenous injection. Other routes of administration include, without limitation, intracerebral, intraventricular, intranasal, or intraocular administration. In some embodiments, the viral vector spreads throughout the CNS tissue following direct administration into the cerebrospinal fluid (CSF), e.g., via intrathecal and/or intracerebral injection, or intra-cisterna magna injection or intracerebroventricular injection. In other embodiments, the viral vectors cross the blood-brain barrier and achieve wide-spread distribution throughout the CNS tissue of a subject following intravenous administration. In other embodiments, the viral vectors are delivered directly to the target regions via intraparenchymal injections. In some cases, the viral vectors may undergo retrograde or anterograde transport to other brain regions following intraparenchymal delivery. In some aspects, the viral vectors have distinct CNS tissue targeting capabilities (e.g., CNS tissue tropisms), which achieve stable and nontoxic gene transfer at high efficiencies.

By way of example, the pharmaceutical composition may be provided to the patient through intraventricular administration, e.g., into a ventricular region of the forebrain of the patient such as the right lateral ventricle, the left lateral ventricle, the third ventricle, or the fourth ventricle. The pharmaceutical composition may be provided to the patient through intracerebral administration, e.g., injection of the composition into or near the cerebrum, medulla, pons, cerebellum, intracranial cavity, meninges, dura mater, arachnoid mater, or pia mater of the brain. Intracerebral administration may include, in some cases, administration of an agent into the cerebrospinal fluid (CSF) of the subarachnoid space surrounding the brain.

In some cases, intracerebral administration involves injection using stereotaxic procedures. Stereotaxic procedures are well known in the art and typically involve the use of a computer and a three-dimensional scanning device that are used together to guide injection to a particular intracerebral region, e.g., a ventricular region. Micro-injection pumps (e.g., from World Precision Instruments) may also be used. In some cases, a microinjection pump is used to deliver a composition comprising a viral vector. In some cases, the infusion rate of the composition is in a range of 1 µl/min to 100 µl/min. As will be appreciated by the skilled artisan, infusion rates will depend on a variety of factors, including, for example, age of the subject, weight/size of the subject, serotype of the AAV, dosage required, and intracerebral region targeted. Thus, other infusion rates may be deemed by a skilled artisan to be appropriate in certain circumstances.

Delivery of rAAVs to a subject may be accomplished, for example, by intravenous administration. In certain instances, it may be desirable to deliver the rAAVs locally to the brain tissue, the spinal cord, cerebrospinal fluid (CSF), neuronal cells, glial cells, meninges, astrocytes, oligodendrocytes, interstitial spaces, and the like. In some cases, recombinant AAVs (e.g., $10^7$-$10^{15}$ Vg/dose) may be delivered directly to the CNS by injection into the ventricular region, and/or to the hippocampus, cortex, cerebellar lobule, or other brain region. AAVs may be delivered with a needle, a catheter or a related device, using neurosurgical techniques known in the art, such as by stereotactic injection. See, e.g., Stein et al., *J Vir.* (1999) 73:3424-9; Davidson et al., *PNAS.* (2000) 97:3428-32; Davidson et al., *Nat Genet.* (1993) 3:219-223; and Alisky and Davidson, *Hum. Gene Ther.* (2000) 11:2315-29; U.S. Pat. Nos. 7,837,668 and 8,092,429.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of neurology, medicine, medicinal and pharmaceutical chemistry, and cell biology described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

In order that this invention may be better understood, the following embodiments and examples are set forth. These embodiments and examples are for purposes of illustration only and are not to be construed as limiting the scope of the invention in any manner.

IV. Exemplary Embodiments

Non-limiting exemplary embodiments of the present disclosure are described below.

1. A method of repressing sense and/or anti-sense transcription of a C9orf72 gene in a cell, the method comprising treating the cell with one or more repressors of the C9orf72 gene, the one or more repressors comprising a transcriptional repression domain and a DNA-binding domain that binds to a target site in the C9orf72 gene, optionally wherein the one or more repressors comprise one or more zinc finger protein transcription factors (ZFP-TF), one or more TAL-effector domain transcription factors (TALE-TF), and/or one or more CRISPR/Cas transcription factors.
2. The method of claim 1, wherein the C9orf72 gene comprises a mutant allele comprising one or more expanded ($G_4C_2$) repeats, optionally wherein the target site is within the one or more ($G_4C_2$) repeats.
3. Use of one or more ZFP-TF, TALE-TF and/or CRISPR/Cas TF repressors that bind to a mutant C9orf72 expanded allele comprising one or more ($G_4C_2$) repeats for repression of sense and/or antisense transcription in a subject in need thereof.
4. The method or use of any of the preceding embodiments, wherein antisense transcription is repressed by at least 50% as compared to untreated cells.
5. The method or use of any of the preceding embodiments, wherein antisense transcription is repressed by at least 70% as compared to untreated cells.
6. The method of use of any of the preceding embodiments, wherein transcripts comprising the expanded repeat are selectively repressed, optionally wherein antisense transcription is repressed, sense transcription from the 1a promoter is repressed and/or sense transcription from the 1b promoter is not repressed.
7. The method or use of any of the preceding embodiments, wherein the one or more ZFP-TF repressors comprise a ZFP having the recognition helix regions in the order shown in Table 1.
8. The method or use of any of the preceding embodiments, wherein the one or more ZFP-TF repressors are administered to the cell as mRNA or using a viral vector.
9. The method or use of embodiment 8, wherein the viral vector is an Ad or AAV vector.
10. The method or use of embodiment 9, wherein the AAV vector is an AAV2/9 vector.
11. The method or use of any of the preceding embodiments wherein the cell is in a live subject and the one or more ZFP-TF repressors are administered to the subject.
12. The method or use of embodiment 11, wherein the one or more ZFP-TF repressors are administered intracerebroventricular, intrathecal, intracranial, retro-orbital (RO), intravenous, intranasal and/or intracisternal intravenously to the subject.
13. The method or use of embodiment 12, wherein the ZFP-TF repressor is administered unilaterally or bilaterally to the hippocampus of the subject, optionally using an AAV vector at a dose of 1E10 to 1E13 (e.g., 6E11) vg/hemisphere.
14. The method or use of any of the preceding embodiments wherein the cell is a neuron.
15. The method or use of any of the previous embodiments, wherein two more ZFP-TF repressors are administered.
16. The method or use of embodiment 15, wherein the two or more ZFP-TF repressors are carried on the same or different non-viral or viral vector.
17. The method or use of any of the preceding embodiments, wherein ALS and/or FTD is treated in the subject.
18. The method or use of any of the preceding embodiments, wherein one or more symptoms of ALS and/or FTD are ameliorated in the subject.
19. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 78021.
20. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 75114.
21. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 75115.
22. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 74969.
23. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79895.

24. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79898.

25. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 74986.

26. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79899.

27. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79901.

28. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79902.

29. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79904.

30. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79916.

31. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 75027.

32. A ZFP-TF fusion protein that binds to a target sequence and comprises the zinc fingers corresponding to an SBS ID as shown in Table 1, the zinc fingers comprising the DNA-binding (recognition) helix sequences shown in a single row of Table 1 for the SBS ID, wherein the SBS ID is 79921.

33. The ZFP-TF fusion protein of any one of embodiments 19-32, wherein the ZFP-TF fusion protein comprises a transcription repressor domain comprising SEQ ID NO:13.

34. The ZFP-TF fusion protein of any one of embodiments 19-33, wherein the zinc finger domain and the transcription repressor domain are linked by a peptide linker comprising SEQ ID NO:26.

EXAMPLES

Example 1: Artificial Transcriptional Repressors

A panel of ZFP-TFs were generated to target expanded human C9orf72 alleles. Exemplary ZFP-TFs are shown in Table 1 below. These ZFP-TFs each contained a ZFP domain having six fingers and a KRAB domain as described above (SEQ ID NO:13). A peptide linker was used to link the ZFP domain to the KRAB domain. The linker had the following amino acid sequence: LRQKDAARGS (SEQ ID NO:26).

Table 1 shows the DNA sequence of the target site and the amino acid sequence of the DNA-binding helix of each zinc finger (F1 to F6) in each ZFP-TF. SEQ ID NOs are shown in parenthesis. The target sequence bound by the ZFP domain in the target site is shown in upper case, while flanking sequences are shown in lower case. SEQ ID NO:24 is the target site on the sense strand of the gene allele, while SEQ ID NO:25 is the target site on the antisense of the gene allele.

The DNA-binding helix is the variable part of a zinc finger and typically contains six or seven amino acid residues. The target specificity of the ZFP domain may be improved by mutations to the ZFP backbone as described in, e.g., U.S. Pat. Pub. 2018/0087072. The symbol "^" in the table indicates that arginine (R) residue at the 4th position upstream of the 1st amino acid in the indicated helix is changed to glutamine (Q). In each zinc finger helix sequence, the positions of the seven DNA-binding amino acids are numbered -1, +1, +2, +3, +4, +5, and +6. Thus, the position for the R-to-Q substitution is numbered as (-5).

TABLE 1

| Exemplary C9orf72 ZFP-TF | | | | | | | |
|---|---|---|---|---|---|---|---|
| | Target site | Zinc Finger DNA-Binding Helix Amino Acid Sequences (SEQ ID NO) | | | | | |
| SBS ID | (SEQ ID NO) | F1 | F2 | F3 | F4 | F5 | F6 |
| 74949 | taGGGGCCGGGGCCGGG GCCggggcgtg (24) | DRSDLSR (27) | RSTHLVR (28) | DRSDLSR (27) | RSTHLVR (28) | DRSDLSR (27) | RSTHLVR (28) |
| 74951 | taGGGGCCGGGGCCGGG GCCggggcgtg (24) | DRSDLSR (27) | RSAHLSR (29) | DRSDLSR (27) | RSAHLSR (29) | DRSDLSR (27) | RSAHLSR (29) |
| 74954 | taGGGGCCGGGGCCGGG GCCggggcgtg (24) | ERGDLKR (30) | RSAHLSR (29) | ERGDLKR (30) | RSAHLSR (29) | ERGDLKR (30) | RSAHLSR (29) |
| 74955 | taGGGGCCGGGGCCGGG GCCggggcgtg (24) | ERGTLAR (31) | RSAHLSR (29) | ERGTLAR (31) | RSAHLSR (29) | ERGTLAR (31) | RSAHLSR (29) |

TABLE 1-continued

Exemplary C9orf72 ZFP-TF

| SBS ID | Target site (SEQ ID NO) | Zinc Finger DNA-Binding Helix Amino Acid Sequences (SEQ ID NO) | | | | | |
|---|---|---|---|---|---|---|---|
| | | F1 | F2 | F3 | F4 | F5 | F6 |
| 74964 | tagGGGCCGGGGCCGGG GCCGgggcgtg (24) | RSADLSE (32) | RSAHLSR (29) | RSADLSE (32) | RSAHLSR (29) | RSADLSE (32) | RSAHLSR (29) |
| 74969 | tagGGGCCGGGGCCGGG GCCGGggcgtg (24) | RSDHLSE (33) | DRSHLAR (34) | RSDHLSE (33) | DRSHLAR (34) | RSDHLSE (33) | DRSHLAR (34) |
| 74971 | tagGGGCCGGGGCCGGG GCCGGggcgtg (24) | RSDHLSQ (35) | DNSHRTR (36) | RSDHLSQ (35) | DNSHRTR (36) | RSDHLSQ (35) | DNSHRTR (36) |
| 74973 | taggGGCCGGGGCCGGG GCCGGggcgtg (24) | RNGHLLD (37) | DRSHLAR (34) | RNGHLLD (37) | DRSHLAR (34) | RNGHLLD (37) | DRSHLAR (34) |
| 74978 | taggGGCCGGGGCCGGG GCCGGggcgtg (24) | RNGHLLD (37) | DNSHRTR (36) | RNGHLLD (37) | DNSHRTR (36) | RNGHLLD (37) | DNSHRTR (36) |
| 74979 | taggGGCCGGGGCCGGG GCCGGggcgtg (24) | RSAHLSE (38) | DNSHRTR (36) | RSAHLSE (38) | DNSHRTR (36) | RSAHLSE (38) | DNSHRTR (36) |
| 74983 | tagggCCGGGGCCGGG GCCGGGgcgtg (24) | RSAHLSR (29) | DRSDLSR (27) | RSAHLSR (29) | DRSDLSR (27) | RSAHLSR (29) | DRSDLSR (27) |
| 74984 | tagggGCCGGGGCCGGG GCCGGGgcgtg (24) | RSDHLSR (39) | DWTTRRR (40) | RSDHLSR (39) | DWTTRRR (40) | RSDHLSR (39) | DWTTRRR (40) |
| 74986 | tagggGCCGGGGCCGGG GCCGGGgcgtg (24) | RSAHLSR (29) | HRKSLSR (41) | RSAHLSR (29) | HRKSLSR (41) | RSAHLSR (29) | HRKSLSR (41) |
| 74987 | tagggGCCGGGGCCGGG GCCGGGgcgtg (24) | RSAHLSR (29) | DSSDRKK (42) | RSAHLSR (29) | DSSDRKK (42) | RSAHLSR (29) | DSSDRKK (42) |
| 74988 | tagggGCCGGGGCCGGG GCCGGGgcgtg (24) | RSAHLSR (29) | DSSTRRR (43) | RSAHLSR (29) | DSSTRRR (43) | RSAHLSR (29) | DSSTRRR (43) |
| 74997 | taggggCCGGGGCCGGG GCCGGGGcgtg (24) | RSAHLSR (29) | RSDDRKT (44) | RSAHLSR (29) | RSDDRKT (44) | RSAHLSR (29) | RSDDRKT (44) |
| 74998 | taggggCCGGGGCCGGG GCCGGGGcgtg (24) | RSAHLSR (29) | RSADRKT (45) | RSAHLSR (29) | RSADRKT (45) | RSAHLSR (29) | RSADRKT (45) |
| 75001 | taggggCCGGGGCCGGG GCCGGGGcgtg (24) | RSAHLSR (29) | RNADRIT (46) | RSAHLSR (29) | RNADRIT (46) | RSAHLSR (29) | RNADRIT (46) |
| 75003 | taggggCCGGGGCCGGG GCCGGGGcgtg (24) | RSAHLSR (29) | RRATLLD (47) | RSAHLSR (29) | RRATLLD (47) | RSAHLSR (29) | RRATLLD (47) |
| 75023 | cacGCCCCGGCCCCGGC CCCGgccccta (25) | RSDTLSV (48) | DTSTRTK (49) | RSDTLSV (48) | DTSTRTK (49) | RSDTLSV (48) | DTSTRTK (49) |
| 75027 | cacGCCCCGGCCCCGGC CCCGgccccta (25) | RNADRIT (46) | HRKSLSR (41) | RNADRIT (46) | HRKSLSR (41) | RNADRIT (46) | RNADRIT (46) |
| 75031 | cacGCCCCGGCCCCGGC CCCGgccccta (25) | RSADRKT (45) | HRKSLSR (41) | RSADRKT (45) | HRKSLSR (41) | RSADRKT (45) | HRKSLSR (41) |
| 75032 | cacGCCCCGGCCCCGGC CCCGgccccta (25) | RSATLSE (50) | HRKSLSR (41) | RSATLSE (50) | HRKSLSR (41) | RSATLSE (50) | HRKSLSR (41) |
| 75055 | cacGCCCCGGCCCCGGC CCCGgccccta (25) | RSADRKT (45) | DSSTRRR (43) | RSADRKT (45) | DSSTRRR (43) | RSADRKT (45) | DSSTRRR (43) |
| 75078 | cacGCCCCGGCCCCGGC CCCGgccccta (25) | RSADLSE (32) | HHRSLHR (51) | RSADLSE (32) | HHRSLHR (51) | RSADLSE (32) | HHRSLHR (51) |
| 75090 | cacgCCCCGGCCCCGGC CCCGgccccta (25) | RSDHLSE (33) | TSSDRTK (52) | RSDHLSE (33) | TSSDRTK (52) | RSDHLSE (33) | TSSDRTK (52) |
| 75105 | cacgcCCCGGCCCCGGC CCCGGCccta (25) | DRSHLTR (53) | DSSTRKT (54) | DRSHLTR (53) | DSSTRKT (54) | DRSHLTR (53) | DSSTRKT (54) |

TABLE 1-continued

Exemplary C9orf72 ZFP-TF

| SBS ID | Target site (SEQ ID NO) | Zinc Finger DNA-Binding Helix Amino Acid Sequences (SEQ ID NO) | | | | | |
|---|---|---|---|---|---|---|---|
| | | F1 | F2 | F3 | F4 | F5 | F6 |
| 75109 | cacgccCCGGCCCCGGC CCCGGCCccta (25) | DKRDLAR (55) | RSADRKT (45) | DKRDLAR (55) | RSADRKT (45) | DKRDLAR (55) | RSADRKT (45) |
| 75114 | cacgccCCGGCCCCGGC CCCGGCCccta (25) | ERGTLAR (31) | RSADRKT (45) | ERGTLAR (31) | RSADRKT (45) | ERGTLAR (31) | RSADRKT (45) |
| 75115 | cacgccCCGGCCCCGGC CCCGGCCccta (25) | ERRDLRR (77) | RSADRKT (45) | ERRDLRR (77) | RSADRKT (45) | ERRDLRR (77) | RSADRKT (45) |
| 74967 | tagggGGCCGGGGCCGGG GCCGGggcgtg (24) | RSDHLSE (33) | SSRYRTK (56) | RSDHLSE (33) | SSRYRTK (56) | RSDHLSE (33) | SSRYRTK (56) |
| 78021 | cacgcCCCGGCCCCGGC CCCGGCcccta (25) | DRSHLTR ^(53) | DSSTRKT (54) | DRSHLTR (53) | DSSTRKT (54) | DRSHLTR (53) | DSSTRKT (54) |
| 78025 | cacgccCCGGCCCCGGC CCCGGCCccta (25) | DKRDLAR ^(55) | RSADRKT (45) | DKRDLAR (55) | RSADRKT (45) | DKRDLAR (55) | RSADRKT (45) |
| 78029 | cacgccCCGGCCCCGGC CCCGGCCccta (25) | ERRDLRR ^(77) | RSADRKT (45) | ERRDLRR (77) | RSADRKT (45) | ERRDLRR (77) | RSADRKT (45) |
| 78033 | cacgccCCGGCCCCGGC CCCGGCCccta (25) | ERRDLRR ^(77) | RSADRKT (45) | ERRDLRR (77) | RSADRKT (45) | ERRDLRR (77) | RSADRKT (45) |
| 79895 | tagggGCCGGGGCCGGG GCCGGggcgtg (24) | RSDHLSE (33) | DRSHLAR ^(34) | RSDHLSE ^(33) | DRSHLAR (34) | RSDHLSE ^(33) | DRSHLAR (34) |
| 79897 | tagggGCCGGGGCCGGG GCCGGggcgtg (24) | RSDHLSE ^(33) | DRSHLAR ^(34) | RSDHLSE ^(33) | DRSHLAR (34) | RSDHLSE ^(33) | DRSHLAR (34) |
| 79898 | tagggGGCCGGGGCCGGG GCCGGggcgtg (24) | RSDHLSE ^(33) | DRSHLAR (34) | RSDHLSE ^(33) | DRSHLAR ^(34) | RSDHLSE (33) | DRSHLAR ^(34) |
| 79899 | tagggGCCGGGGCCGGG GCCGGGgcgtg (24) | RSAHLSR ^(29) | HRKSLSR (41) | RSAHLSR ^(29) | HRKSLSR (41) | RSAHLSR (29) | HRKSLSR (41) |
| 79901 | tagggGCCGGGGCCGGG GCCGGGgcgtg (24) | RSAHLSR (29) | HRKSLSR (41) | RSAHLSR ^(29) | HRKSLSR (41) | RSAHLSR ^(29) | HRKSLSR (41) |
| 79902 | tagggGCCGGGGCCGGG GCCGGGgcgtg (24) | RSAHLSR (29) | HRKSLSR (41) | RSAHLSR ^(29) | HRKSLSR (41) | RSAHLSR (29) | HRKSLSR ^(41) |
| 79903 | tagggGCCGGGGCCGGG GCCGGGgcgtg (24) | RSAHLSR (29) | HRKSLSR ^(41) | RSAHLSR ^(29) | HRKSLSR (41) | RSAHLSR ^(29) | HRKSLSR (41) |
| 79904 | tagggGCCGGGGCCGGG GCCGGGgcgtg (24) | RSAHLSR (29) | HRKSLSR ^(41) | RSAHLSR (29) | HRKSLSR ^(41) | RSAHLSR (29) | HRKSLSR ^(41) |
| 75025 | cacGCCCCGGCCCCGGC CCCGgccccta (25) | REQDLKQ (57) | HRKSLSR (41) | REQDLKQ (57) | HRKSLSR (41) | REQDLKQ (57) | HRKSLSR (41) |
| 79915 | cacGCCCCGGCCCCGGC CCCGgccccta (25) | REQDLKQ ^(57) | HRKSLSR ^(41) | REQDLKQ ^(57) | HRKSLSR ^(41) | REQDLKQ (57) | HRKSLSR (41) |
| 79916 | cacGCCCCGGCCCCGGC CCCGgccccta (25) | REQDLKQ (57) | HRKSLSR ^(41) | REQDLKQ (57) | HRKSLSR ^(41) | REQDLKQ (57) | HRKSLSR (41) |
| 79921 | cacGCCCCGGCCCCGGC CCCGgccccta (25) | RNADRIT ^(46) | HRKSLSR ^(41) | RNADRIT ^(46) | HRKSLSR (41) | RNADRIT ^(46) | HRKSLSR (41) |

The ZFP-TFs were evaluated by standard SELEX analysis (see, e.g., Miller et al., *Nat Biotech*. (2010) doi:10.1038/nbt.1755; Wilen et al., *PLoS* (2011) 7(4):e1002020). All were shown to bind to their target sites.

Five types of human cell lines and one mouse cell line were used in the study. The C9021 fibroblast cell line was obtained from The ALS Institute at Columbia University and was derived from an ALS-FTD patient. It contains 5 $G_4C_2$ repeats on its normal allele and approximately 850 repeats on its expanded allele. The wildtype fibroblast cell line (NDS00035), the 353TRAD and 204TDP fibroblast lines were obtained from the National Institute of Neurological Disorders and Stroke. The wildtype line contains two $G_4C_2$ repeats on each allele. 353TRAD line contains 5 repeats on one allele and 8 repeats on the other allele. 204TDP has 2 repeats on one allele and 20 repeats on the other allele. For all fibroblast experiments, human neurons were obtained from Cell Dynamics International (iCell GABANeurons Kit, 01434; Cat #R1013; Cell Lot #104901). Mouse cortex neurons were obtained from GIBCO (Cat #A15586). ZFP 74960, which binds to its target region but had no observable repression effect, was used as a negative control.

For all experiments done inpatient derived fibroblast cells, transfection of ZFP-TFs mRNAs into the cells was performed using 96-well Shuttle Nucleofector system from Lonza. 1, 3, 10, 30, 100, and 300 ng of ZFP-TF mRNA per 40,000 cells were transfected using Amaxa P2 Primary Cells Nucleofector kit using the CA-137 program. After overnight incubation, a Cells-to-Ct kit (Thermo Fisher Scientific) was used to generate cDNA from transfected cells followed by gene expression analysis using qRT-PCR.

For neuronal transduction, ZFPs were made into AAV6 plasmids. Neurons were transduced with AAV6-ZFP. All transductions were performed at 3,000 MOI. Mouse neurons were collected 7 days post transduction while human neurons were collected 19 days post transduction. After collecting the cells, they were processed for microarray analysis.

Screening analysis was performed in multiple rounds. In each round, ZFPs were tested at multiple concentrations to identify ZFP-TFs with suitable on target (selective repression) pattern. Round 2 of screening was done in C9 (C9021) cells to evaluate the levels of the expanded sense transcript (disease) C9orf72 vs. total C9orf72 ("total C9") mature mRNA following ZFP-TF treatment. The RT-PCR assay used a primer/probe set that targets intronic region 1a.

```
Expanded sense C9orf72 transcript:
Forward:
                                      (SEQ ID NO: 61)
5' CCCTCTCTCCCCACTACTTG 3'

Reverse:
                                      (SEQ ID NO: 62)
5' CTACAGGCTGCGGTTGTTTCC 3'

Probe:
                                      (SEQ ID NO: 63)
5' TCTCACAGTACTCGCTGAGGGTGA 3'
```

Figure 2A:
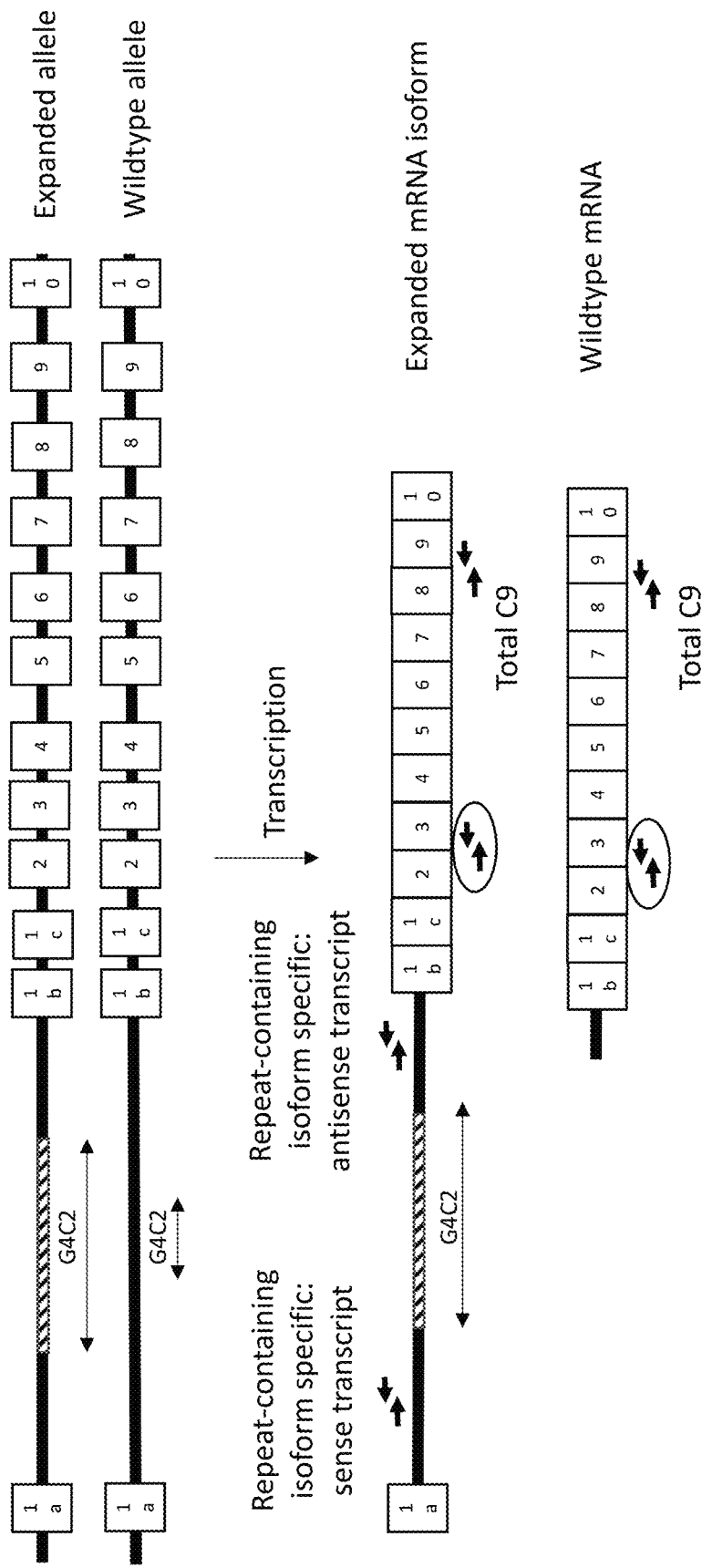
FIGS. 2A-D show repression of C9orf72 expression ("Total C9") in the indicated cell types using the indicated ZFP-TFs. In addition, the figures show repression of the expression of a longer mRNA isoform (expanded) comprising intron 1a, which is predominantly produced by the expanded, mutant allele ("Repeat-containing isoform specific"). The expanded isoform is predominantly expressed in C9 patient lines.
Figure 2B:
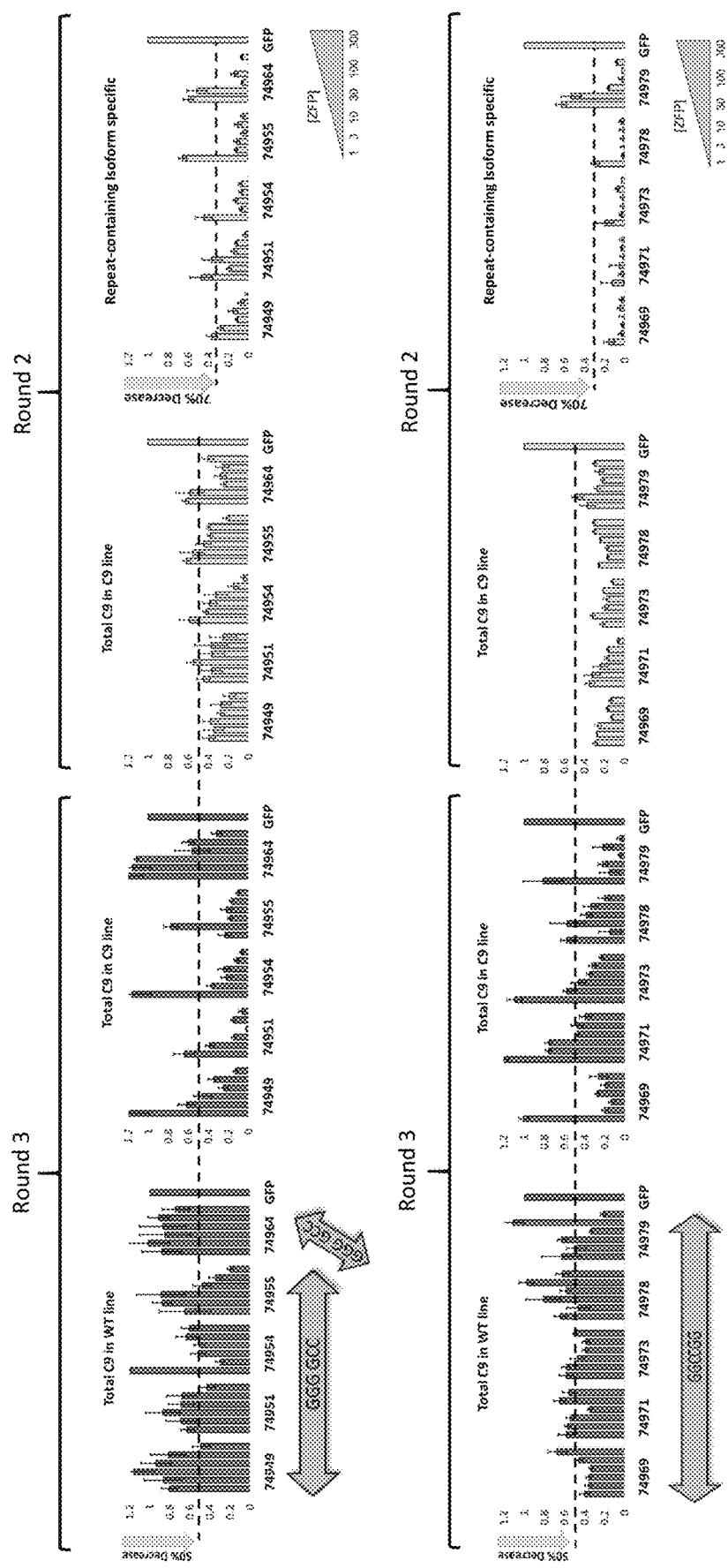
Figure 2C:
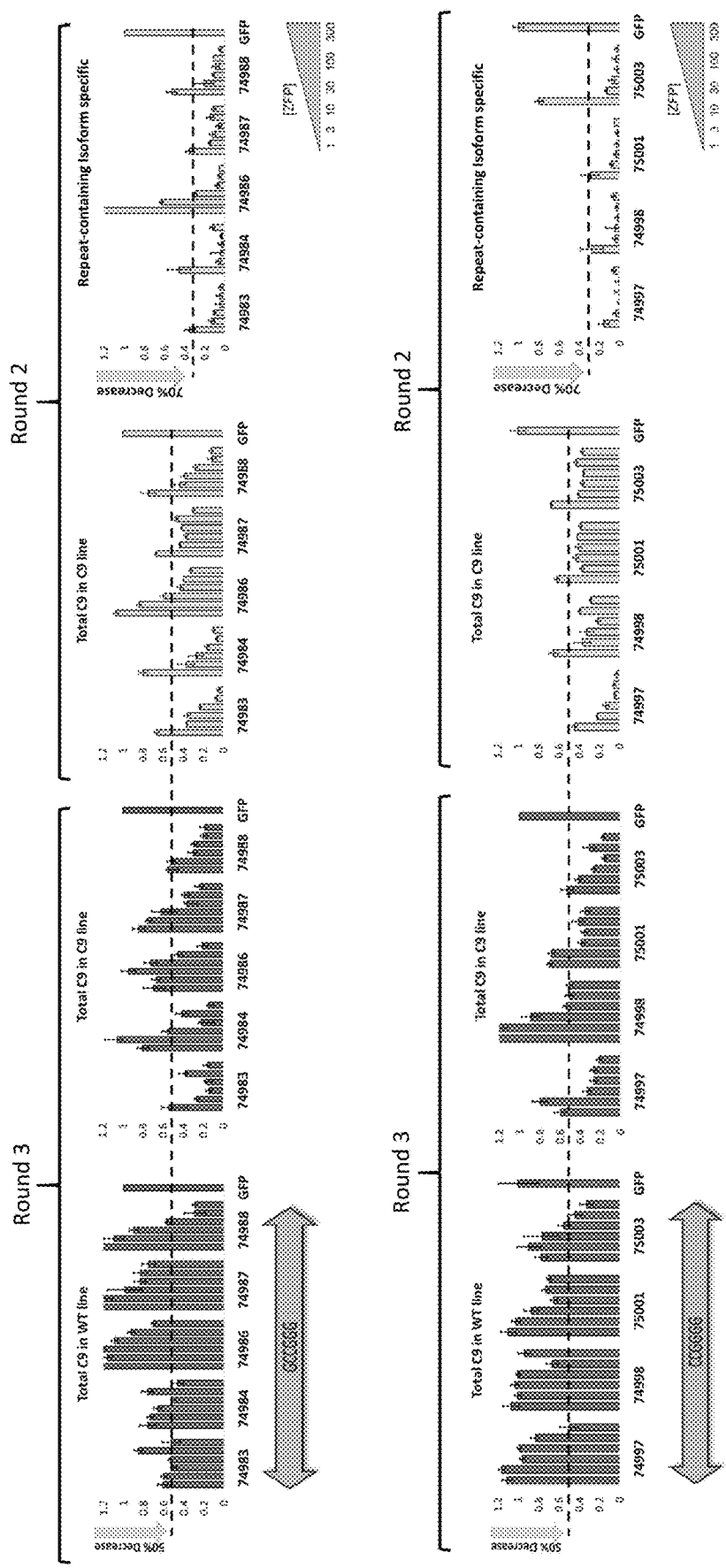
Figure 2D:
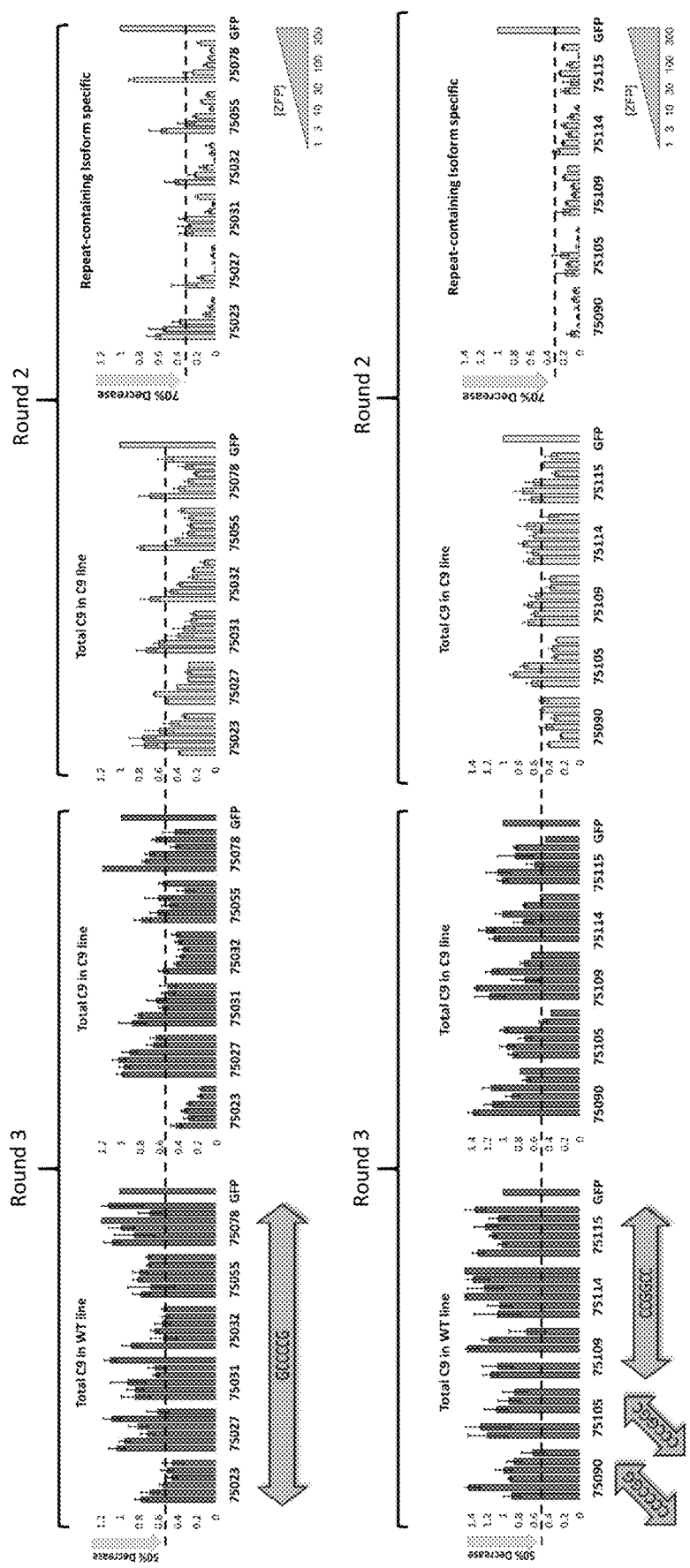

The $G_4C_2$ expansion leads to inefficient splicing and accumulation of the expansion-containing pre-mRNA (FIG. 2A). In contrast, the wild-type (WT) pre-mRNA, which is efficiently spliced, is present at very low levels. By using this assay in the C9021 cells, we showed that the tested ZFP-TFs displayed a wide range of repression of the expanded sense (disease) C9orf72 transcript. (FIGS. 2B-D).

In order to evaluate repression of total C9orf72 mRNA, a different primer/probe set, denoted as "Total C9" (FIG. 7A), was used:

```
Total C9orf72 mRNA:
Forward:
                                      (SEQ ID NO: 58)
5' CTATGTGTGTGGTGGGATATGG 3'

Reverse:
                                      (SEQ ID NO: 59)
5' CTCCAGGTTATGTGAAGCAGAA 3'

Probe:
                                      (SEQ ID NO: 60)
5' AGGCCTGCTAAAGGATTCAACTGGAA 3'
```

This primer/probe set could detect mRNAs comprising a region spanning exons 8 and 9. This region is present in all of the C9orf72 mRNA isoforms. As shown in FIG. 2b, many ZFP-TFs showed modest repression of total C9orf72 transcripts. For example, ZFP-TFs 75114 and 75115 repressed the expanded sense (disease) transcript by more than 70%, while preserving the expression of total C9orf72 mRNA by more than 50% (FIG. 2D, Round 2 data).

In Round 3, the total C9orf72 mRNA was evaluated and compared between C9021 cells and wildtype (WT) cells in order to further evaluate the effect of the tested ZFP-TFs on total C9orf72 mRNA levels. The data show that the total C9orf72 mRNA levels in the mutant cells decreased much more dramatically than those in the WT cells (FIGS. 2B-D) and were much less impacted in wildtype cells treated by the same ZFP-TFs. Overall data illustrate that for some ZFPs, such as 75109, 75114, and 75115, the expanded isoform is repressed significantly (about 70%) while maintaining about 50% of the total C9 transcript C9 patient fibroblast lines.

Figure 6:
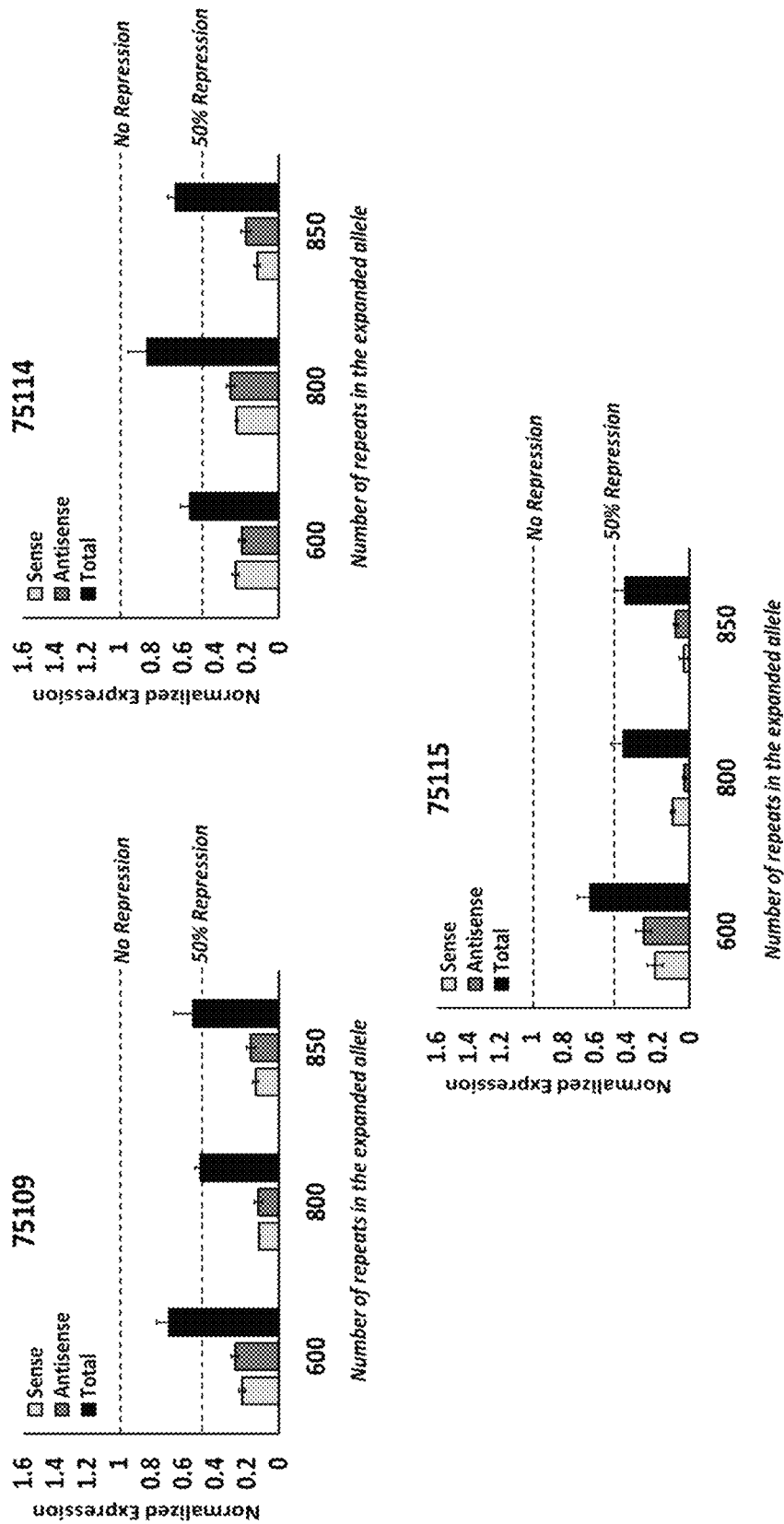
FIG. 6 shows the repression of total C9 transcript along with expanded sense and antisense transcripts (disease isoform) in three different fibroblast lines obtained from different ALS patients, each containing different $G_4C_2$ repeat numbers (about 600, 800, and 850 repeats, respectively) on their expanded allele. After the cells were exposed to 100 ng of ZFP-TFs 75109, 75114, and 75115, isoform selective assay was used to evaluate the levels of repression. All three ZFP-TFs maintained selective repression in all three cell lines.

The isoform selective repression of the ZFP-TFs 75109, 75114, and 75115 was evaluated in three different patient derived fibroblast cells containing different $G_4C_2$ expansion repeats on their expanded alleles (600, 800, and 850) (FIG. 6). All three ZFPs exhibited a similar behavior independent of the repeat expansion length, illustrating that the selective repression of the ZFP-TFs is independent from the $G_4C_2$ repeat length.

Figure 7:
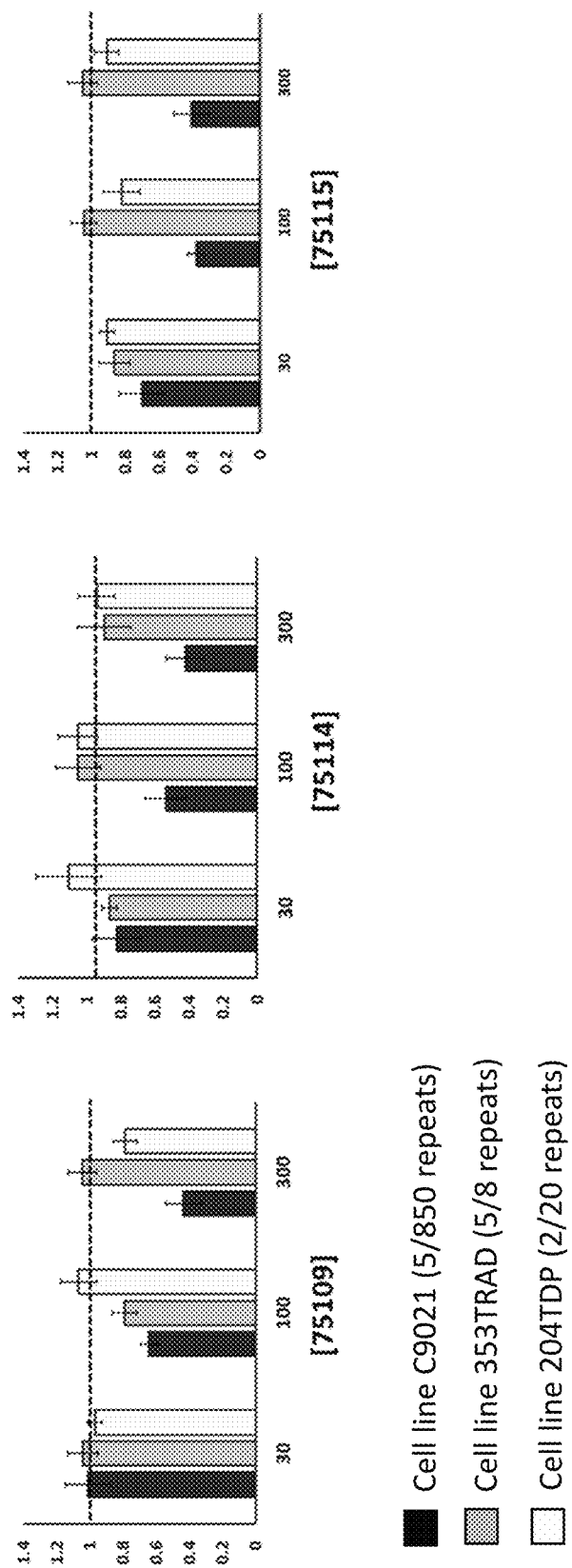
FIG. 7 shows the repression of total C9 transcript in two cell lines from healthy individuals with larger than typical $G_4C_2$ repeat numbers on their alleles. Healthy individuals typically have 2-5 $G_4C_2$ repeats on each of their C9orf72 alleles. However, some healthy individuals contain more repeats. To ensure that sufficient binding sites for the ZFP-TFs are provided, cell lines containing more than typical repeat numbers (5/8 and 5/20 repeats) were used. Total C9 transcript is minimally affected in these cell lines.

The repression of total C9 transcript in two cell lines from healthy individuals with larger than normal $G_4C_2$ repeat numbers on their alleles was evaluated (FIG. 7). Total C9 transcript is minimally affected in healthy cell lines. The ZFP mediated repression of the total C9 mRNA transcript in patient derived cell line (C9021) is not a true representation of the WT isoform levels because the PCR assay used to detect the total C9 mRNA transcript targets exons 8 and 9 which exits in both the expanded and non-expanded (WT) isoforms (FIG. 2A). The repression of the total C9 mRNA transcript in response to isoform selective ZFP-TFs (75109, 75114, and 75115) was evaluated in two different healthy lines with different $G_4C_2$ repeat length on their alleles (FIG. 7). Cell lines 353TREAD has 5 repeats on one allele and 8 repeats on the other allele, while cell line 204TDP has 2 repeats one allele and 20 repeats on the other allele. While total C9 mRNA transcript was repressed in a dose dependent manner in C9 line C921 (5 repeats on the non-expanded allele and 850 repeats on the expanded allele) but it was minimally affected in the two other cell lines without expanded allele, indicating that the repression of total C9 isoform in disease line (5/850) is a consequence of the repression of the expanded isoforms and the expression of the non-expanded isoform is not affected by the selective ZFP-TFs (FIG. 7).

Without being bound by theory, it is possible that the present ZFP-TFs are able to work in a cooperative manner in order to selectively repress the allele with numerous repeats. That may be mediated by higher-order complexes, e.g., through recruitment of a KAP1 co-repressor that associates with the ZFP-linked KRAB domains. Under this hypothesis, the KAP1/KRAB "scaffold" across multiple ZFP-TFs increases the stability of the transcription repression machinery and enables the preferential repression of the expanded C9orf72 allele over the wildtype allele.

Example 2: Specificity of C9orf72 Repression

The global specificity of the ZFP-TFs shown in Table 1 was evaluated by microarray analysis in 3 cell lines: C9021 fibroblast cells, primary mouse cortical neurons and human neurons. For C9021 cells, in brief, 100 ng of ZFP-TF encoding mRNA was transfected into 150,000 C9021 cells in quadruplicates. After 24 hours, total RNA was extracted and processed via the manufacturer's protocol (Affymetrix Genechip MTA1.0). Robust Multi-array Average (RMA)

was used to normalize raw signals from each probe set. Analysis was performed using Transcriptome Analysis Console 3.0 (Affymetrix) with the "Gene Level Differential Expression Analysis" option. ZFP-TF-transfected samples were compared to samples that had been treated with an irrelevant ZFP-TF (one that does not bind to a C9orf72 target site). Change calls were reported for transcripts (probe sets) with a >2 fold difference in mean signal relative to control, and a P-value <0.05 (one-way ANOVA analysis, unpaired T-test for each probe set). Similar procedure was also done for neurons, except they were transduced with AAV6 at MOI of 3000 and cultured for 7 days form mouse neurons and 19 days for human neurons before harvest.

Figure 8A:
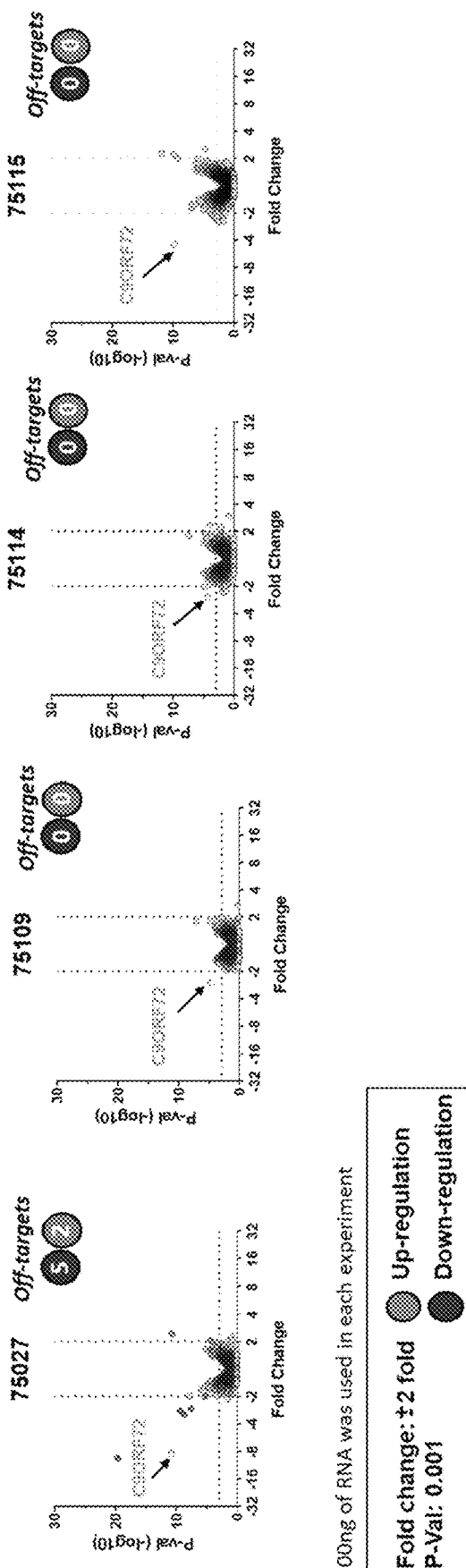
FIGS. 8A-8C show the results of microarray analysis in ALS patient-derived primary fibroblast cells (C921, also called C9021), in mouse primary neurons, and in human primary neurons showing specificity of the indicated repressors (75027, 75109, 75114, and 75115). ZFP-TF 75027 targets the repeated GCCCCG (SEQ ID NO:8) motif, while ZFP-TFs 75109, 75114, and 75115 target the CCGGCC (SEQ ID NO:11) motif in the antisense strand of the C9orf72 gene.
Figure 8B:
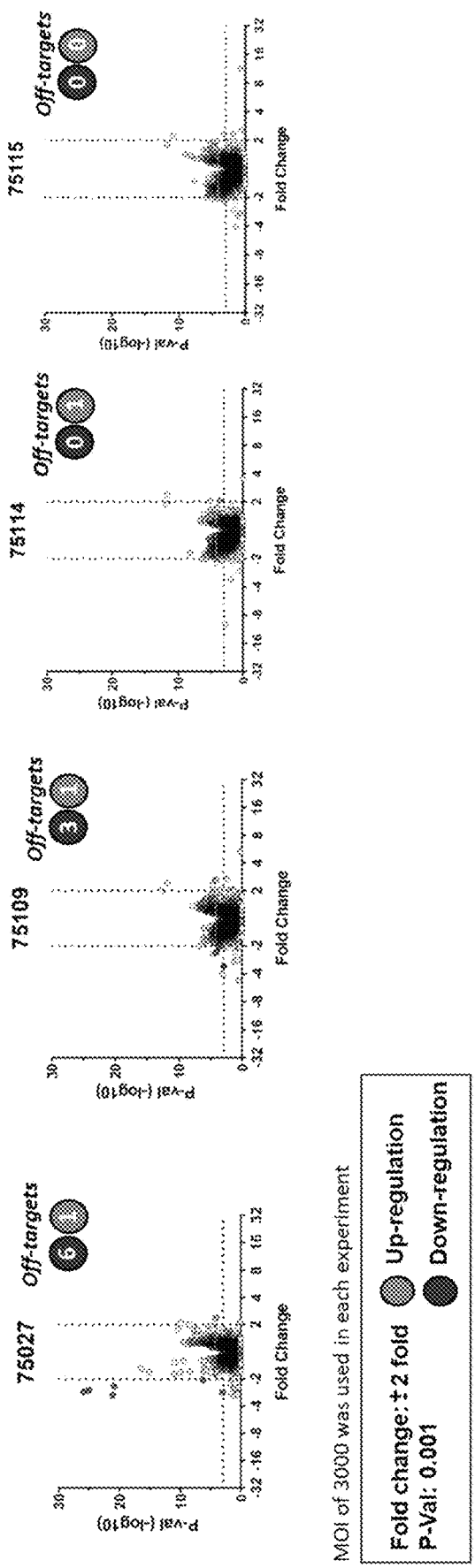
Figure 8C:
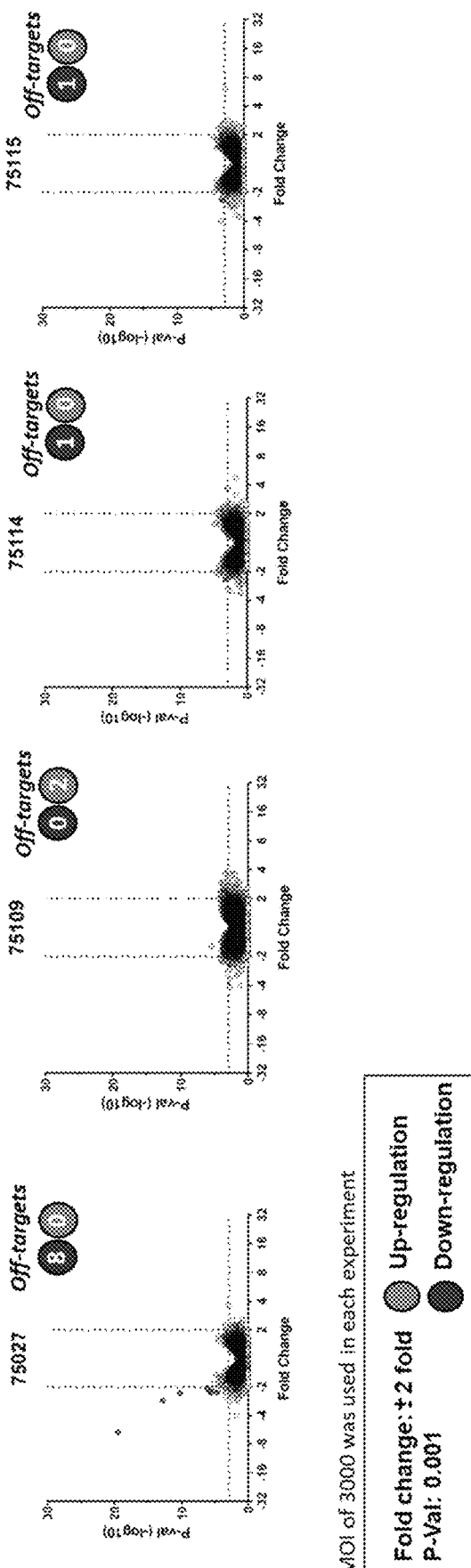

Exemplary data are shown in FIGS. 8A-8C. The data show that ZFP-TF 75027 exhibited several off-targets in addition to C9orf72 (shown circled) while ZFP-TFs 75109, 75114, and 75115 repressed only C9orf72 with minimal off-targets in both fibroblast and neurons in both human and mouse. These results demonstrate that the representative ZFP-TFs are highly specific for C9orf72.

Example 3: Detection of Antisense-Specific Repression

Because sense and antisense transcripts are encoded by overlapping regions of the DNA, we developed a detection strategy based on the differential processing of the transcripts. For the sense mRNA from an expanded allele, the intron containing an expanded region (intron 1a) is misspliced and retained, but all other introns are removed, including intron 1b. In contrast, the intron 1b region is a predicted exon in the antisense mRNA transcript and should be retained. Thus, we designed and tested primers located within intron 1b and demonstrated specific detection of the antisense transcripts as further described below.

To detect C9orf72 transcripts, we used droplet digital PCR (ddPCR). In brief, to create the sense or antisense cDNA templates, RNA was purified from C9orf72 patient and healthy control cells (C9orf72 lines: C9-3, C9-6, C9-7, C9-5, C9-10, C9-11, C9-2, C9-4; Control lines: KinALS6, Con3, Kin1ALS17, Con8, Con10, Con1; see Lagier-Tourenne et al., $PNAS$ (2013) 110(47):E4530-9) and used to synthesize cDNA using Superscript III (Thermo Fischer Scientific) first strand synthesis system as follows:
1) 0.5 µg of RNA, 0.5 µL of 10 mM strand specific primer and dNTPs mix were mixed and made up to 10 µL with water. For generation of the sense template, the primer 5' CTCTAGCGACTGGTGGAATTG 3' (SEQ ID NO:64) was used. To generate the antisense template, the primer 5' GTGCATGGCAACTGTTTGAATA 3' (SEQ ID NO:65) was used.
2) This reaction was incubated at 65° C. for 5 minutes for denaturation and placed on ice for at least 1 minute.
3) cDNA synthesis mix was prepared using these reagents: 10×RT buffer (2 µL); 25 mM MgCl2 (4 µL); 0.1 M DTT (2 µL); RNase OUT (1 µL); Superscript III (1 µL).
4) 10 µL of this reaction was added to the RNA mix and incubated at 50° C. for 50 minutes. The reaction was then inactivated by a 5 minute incubation at 85° C.

Figure 3:
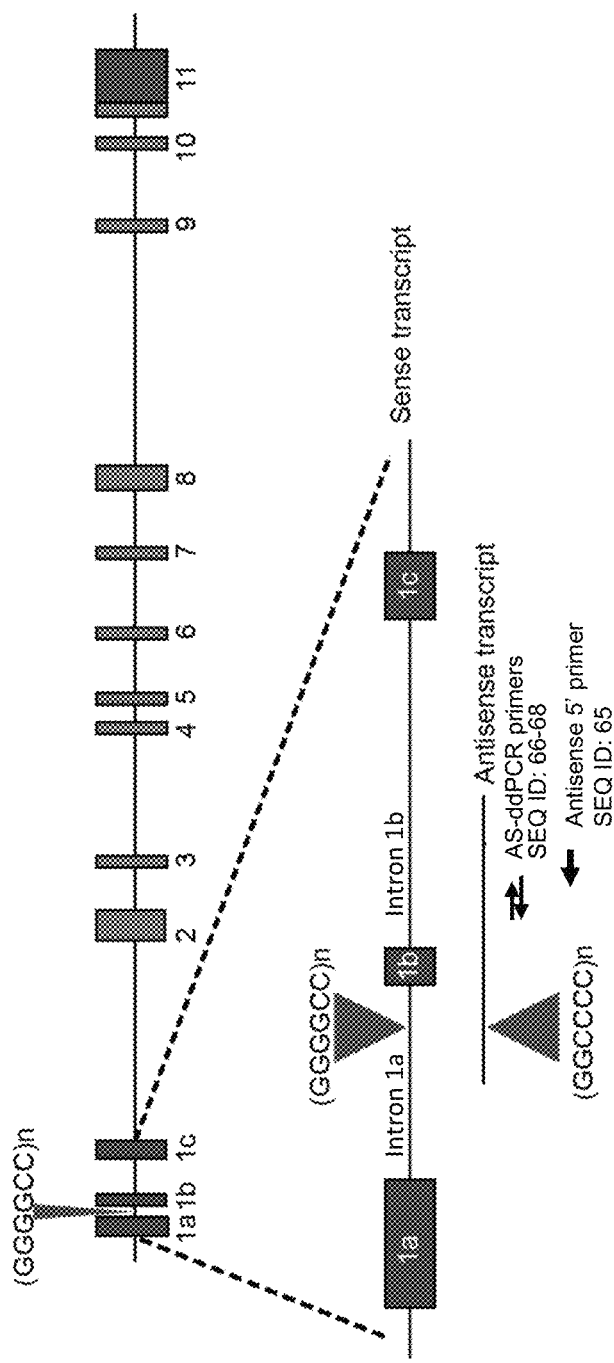
FIG. 3 shows a diagram of the promoter regions for the sense and antisense transcripts in the C9orf72 expanded allele. Indicated are the primer pairs for specific detection of the sense, total and antisense transcripts. AS: antisense. ddPCR: droplet digital PCR. The figure discloses SEQ ID NOs:1, 1 and 7, respectively, in order of appearance.

The template was then subjected to ddPCR using a labeled probe according to manufacturer's protocols. In brief, PCR reactions were done in an ABI PCR 96-well plate using dUTP-free ddPCR Supermix for Probes (Bio-Rad). The PCR Mastermix was prepared according to manufacturer's directions. The antisense primer-probe set located on the intron 1b region (FIG. 3) is shown below.

Forward:
(SEQ ID NO: 66)
5' CAAAGCCTGGTGGTGTTCAA 3'

Reverse:
(SEQ ID NO: 67)
5' GGACATGACCTGGTTGCTTC 3'

Probe:
(SEQ ID NO: 68)
5' CGCGGCCAGATAGACCCAATGAGCA 3'.

The reactions were set up as follows:
1) Complete Master mix was distributed evenly among 8 wells of ABI PCR plate.
2) 10 µL 1:10-diluted RT reactions or water were added to the sample wells.
3) 15 µL of Master Mix was transferred into RT-containing wells.
4) The plate was sealed, vortexed and spun down briefly.

To make the droplets, cartridges were used as follows:
1) 70 µL of probe oil was placed in the wells labeled oil on the cartridge and 20 µL of the ddPCR reactions were place in the wells labeled sample.
2) A rubber gasket was placed on top of the cartridge.
3) 40 µL of the droplets were transferred into a fresh Eppendorf 96 well plate.

The plate was sealed with aluminum foil and PCR was performed according to manufacturer's protocol.

Figures 4A, 4B:
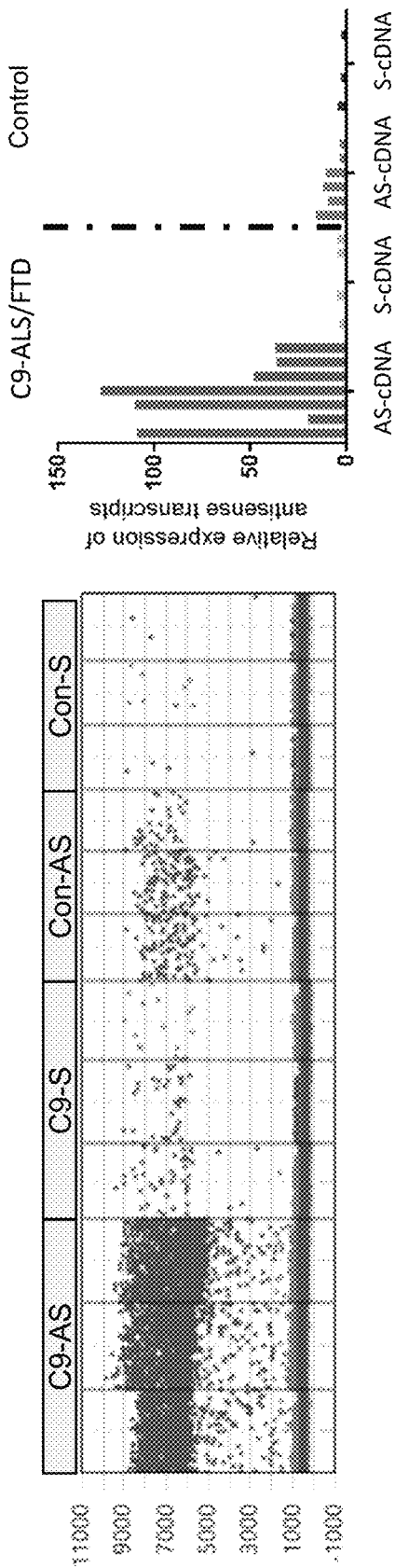
FIGS. 4A and 4B show that primers targeting intron 1b specifically detect the antisense pre-mRNA. Strand-specific PCR was used to generate sense (S) or antisense (AS) cDNA templates from healthy control (Con) or the C9 cells (C9). For example, C9-AS indicates the ddPCR results obtained with antisense cDNA templates produced from RNA isolated from C9 cells.

The data show that in C9orf72 fibroblast lines, these primers amplified an exon in the antisense expanded pre-mRNA (C9-AS) and that the complementary region was absent from the sense region (C9-S) (FIG. 4A). Thus, the ddPCR antisense primers herein specifically detected antisense pre-mRNA that were clearly elevated in 7 different C9 patient-derived fibroblasts as compared to 6 different control fibroblasts (FIG. 4B).

Example 4: Expanded Allele Sense and Antisense Pre-mRNA Repression

Figure 5A:
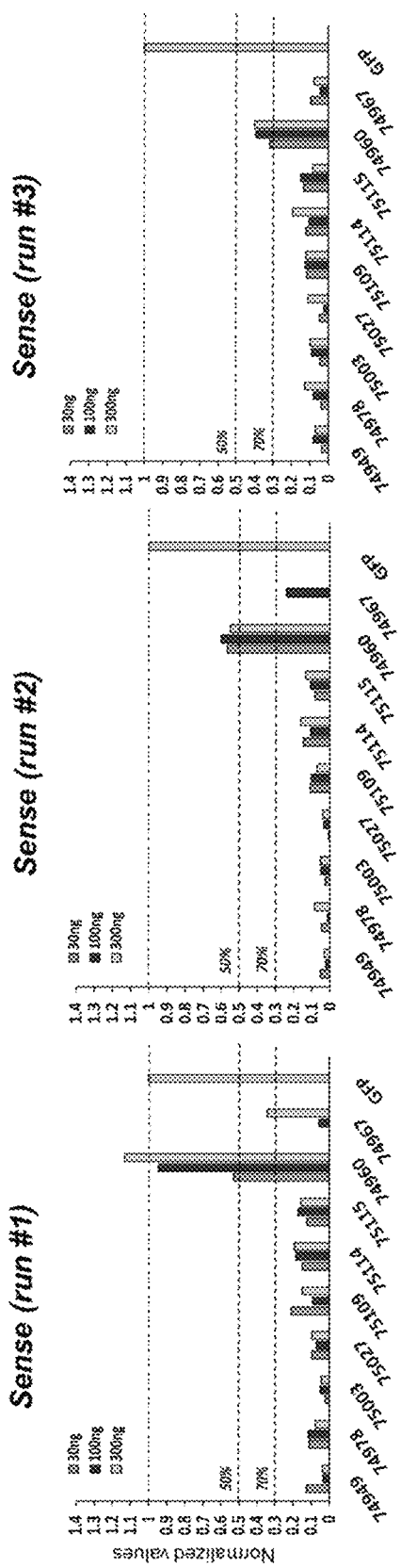
FIGS. 5A-C are graphs showing repression of the transcripts in C9 cells using repeat-containing isoform specific assays.
Figure 5B:
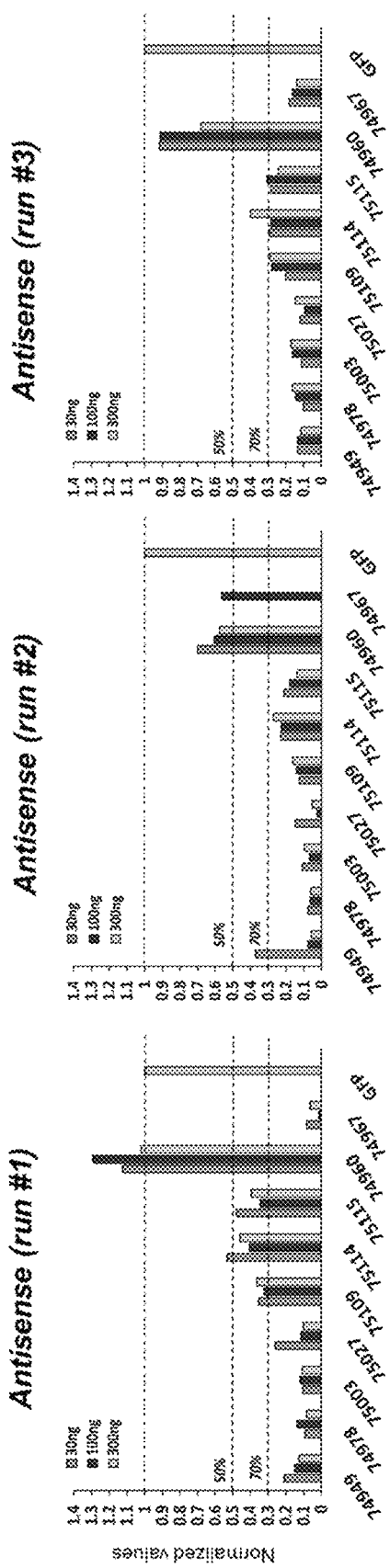
Figure 5C:
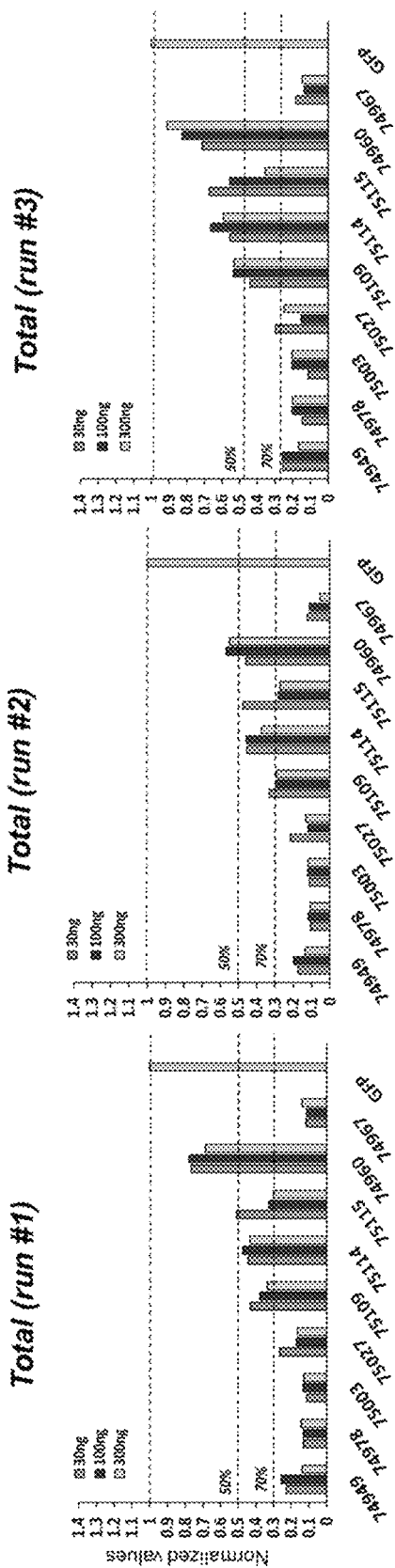

To test the activity of the ZFP-TF repressors on the expanded allele, the cells were treated with the ZFP-TFs 74949, 74978, 75003, 75027, 75109, 75114, 75115, 74967 (Table 1), or 74960 (negative control), as described above. Two separate PCR assays were used to assess the ZFP-TF mediated repression by investigators who were blinded to samples order. Each assay uses a different primer/probe (FIGS. 5A-5C).

For runs #1 and #2, assays to measure sense expanded, antisense expanded, and total C9 were performed as described above except that the amplification was performed with random hexamers according to standard protocols in the art and with the primers shown below:
Antisense expanded C9orf72 pre-mRNA (FIG. 5B): as shown in Example 3 above.
Sense expanded C9orf72 pre-mRNA (FIG. 5A): this primer/probe set could detect mRNAs comprising a region spanning exon 1a and intron 1a.

Forward:
(SEQ ID NO: 69)
5' ACTACTTGCTCTCACAGTACTCG 3'

Reverse:
(SEQ ID NO: 70)
5' TAGCGCGCGACTCCTGAGTTCC 3'

```
Probe:
                                                 (SEQ ID NO: 71)
5' AGGGAAACAACCGCAGCCTGTAGCAAGCTC 3'.
```

Total C9orf72 mRNA (FIG. 5C): this primer/probe set could detect mRNAs comprising a region within exon 2.

```
Forward:
                                                 (SEQ ID NO: 72)
5' TGTGACAGTTGGAATGCAGTGA 3'

Reverse:
                                                 (SEQ ID NO: 73)
5' GCCACTTAAAGCAATCTCTGTCTTG 3'

Probe:
                                                 (SEQ ID NO: 74)
5' TCGACTCTTTGCCCACCGCCA 3'.
```

Run #3 (FIGS. 5A and 5C) used the primers shown above in Example 1 (FIGS. 2B-2D). For antisense disease transcript, the following primer/probe was used for detecting intronic region 1b (FIG. 5B).

```
Forward:
                                                 (SEQ ID NO: 78)
5' CAGCTTCGGTCAGAGAAATGAG 3'

Reverse:
                                                 (SEQ ID NO: 79)
5' AAGAGGCGCGGGTAGAA 3'

Probe:
                                                 (SEQ ID NO: 80)
5' CTCTCCTCAGAGCTCGACGCATTT 3'
```

Despite the fact that different primer/probe sets, and different PCR assays were used (run #1 and run #2 were conducted by similar assays but different from run #3), data were consistent and the repression levels were comparable.

Taken together, all runs consistently demonstrated that some of the ZFP-TFs were capable of strongly suppressing all three transcripts (sense, antisense, and total) (e.g., ZFP-TFs 74978, 75003, and 75027), whereas some ZFP-TFs (e.g., ZFP-TFs 75109, 75114, and 75115) were selectively repressing the sense and antisense disease transcripts while preserving the total C9 transcript (selective repression).

Example 5: Modulation of Human C9orf72 in BAC C9orf72 Transgenic Mouse Neurons All repressors targeted to BAC mouse C9orf72 are cloned into rAAV6 vectors using a CMV promoter to drive expression. The recombinant AAV is produced in HEK293T cells, purified using a CsCl density-gradient, and titered by real time qPCR according to methods known in the art. The purified virus is used to infect cultured primary mouse cortical neurons at 3E5, 1E5, 3E4, and 1E4 Vg/cell. After 7 days, total RNA is extracted and the expression of C9orf72 sense and antisense transcripts as well as two reference genes (e.g. Atp5b and Eif4a2) are monitored using RT-qPCR.

All ZFP-TF-encoding AAV vectors will effectively repress their targets in the mouse cells over a broad range of infected doses, with some ZFPs reducing the target by greater than 95% at multiple doses. In contrast, no gene repression is observed for a CMV-GFP rAAV6 virus tested at equivalent doses, or mock-treated neurons.

Example 6: In Vivo Gene Repression Driven by AAV-Delivered ZFP-TFs

Figure 9:
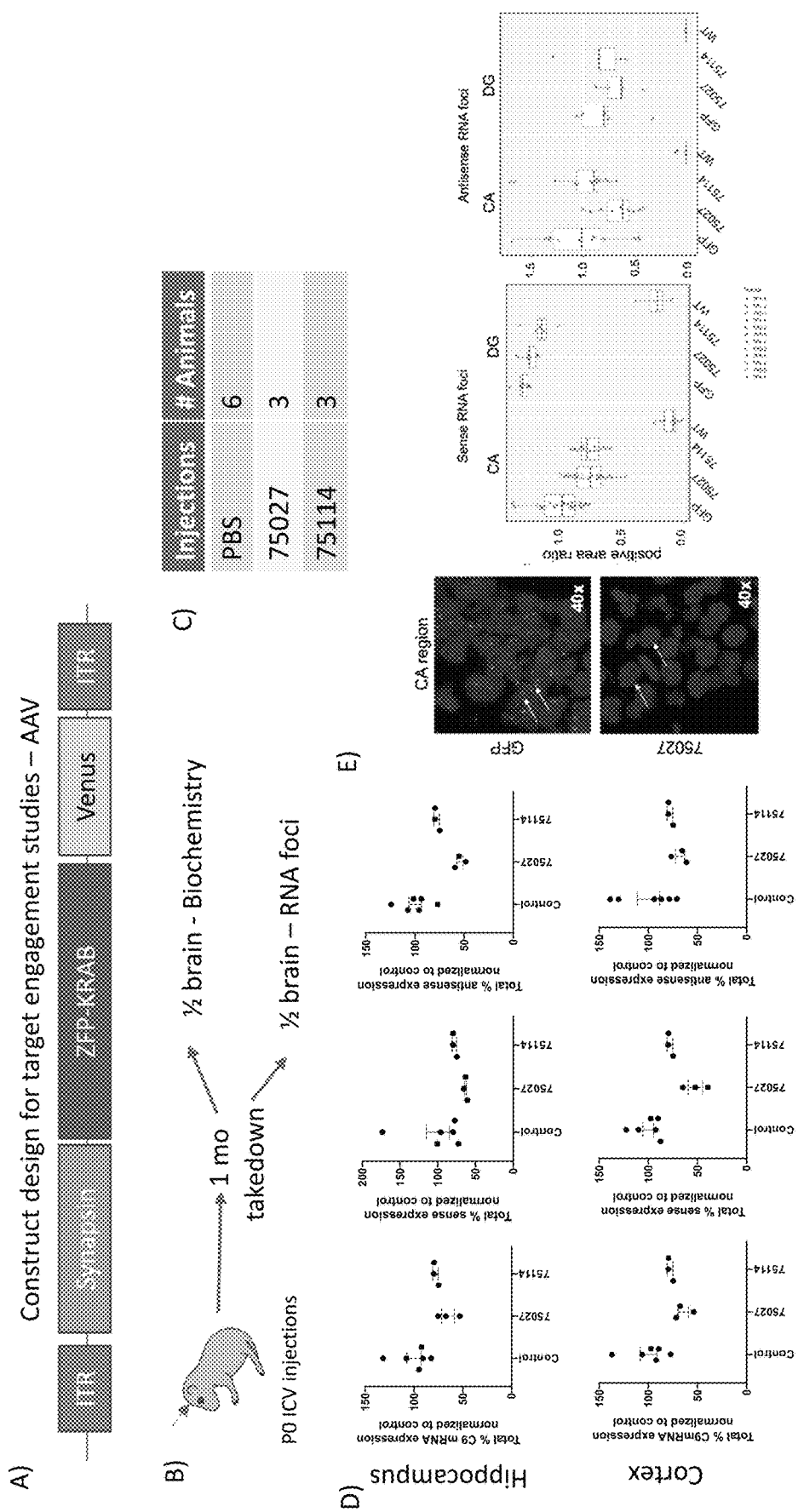
FIG. 9 shows in vivo target engagement of ZFPs in C9orf72 BAC transgenic mice. Panel A shows the AAV construct used for injections. The construct contains a synapsin promoter, ZFP-KRAB coding sequence, and a Venus tag. Panels B and C show the study design, under which neonates were injected intracerebroventricularly (ICV) with AAV containing the ZFP-KRAB expression construct and taken down one month post-injection for downstream analysis. Panel D shows the levels of sense, antisense and total C9 RNA in ZFP-KRAB (75027) injected animals in the hippocampus and cortex. Panel E shows representative images of sense and antisense RNA foci and quantification from the cornu ammonis (CA) and dentate gyrus (DG) regions of the hippocampus in ZFP-KRAB (75027) injected animals.

The C9orf72 BAC transgenic mice used for target engagement studies contain 98 kb of human transgene containing a full length C9orf72 gene allele having about 500 $G_4C_2$ repeats with substantial flanking sequence (Liu et al., Neuron (2016) 90(3):521-34). Two ZFP-TFs, ZFP-TF 75027 or ZFP-TF 75114, with different potencies (ZFP-TF 75027 being more potent; FIG. 2D), were selected for this study. The expression cassettes for the two fusion proteins were both cloned into rAAV vector containing a synapsin promoter to drive expression and a coding sequence for a self-cleavable peptide (e.g., a 2A peptide such as T2A or P2A) followed by a Venus tag to measure biodistribution (FIG. 9, Panel A). The rAAV was produced in HEK293T cells and titered by ddPCR using primers on the ITRs.

To evaluate the effect of ZFP-TF expression on the repression of expansion-containing sense and antisense transcripts in vivo, the ZFP-TF rAAVs were delivered into P0 C9-BAC or WT mice by intracerebroventricular (ICV) injections. Briefly, vehicle (PBS) or ZFP-TF 75027 rAAV or ZFP-TF 75114 rAAV (total dose of 2E10 Vgs per ventricle) was administered bilaterally (2 µl per ventricle) into neonatal C9-BAC mice (matched for repeat length) or WT mice (FIG. 9, Panel C). The animals were sacrificed four weeks post-injection and one hemisphere was embedded for RNA foci analysis and the other hemisphere was micro-dissected into cortex, hippocampus and cerebellum for further analysis (FIG. 9, Panel B). Quantitation of viral genomes and Venus mRNA and protein showed widespread biodistribution with equivalent transduction and expression of both ZFP-TF 75027 and ZFP-TF 75114.

Total RNA was extracted from cortex and hippocampus tissues and cDNA was made using iScript cDNA synthesis kit (BioRad). ddPCR was performed to measure the expression of sense and antisense expansion-containing transcripts and total C9 mRNA levels normalized to mouse TBP levels. The primers used for this assay were:

```
Total C9 mRNA:
Forward:
                                                 (SEQ ID NO: 72)
5' TGTGACAGTTGGAATGCAGTGA 3'

Reverse:
                                                 (SEQ ID NO: 73)
5' GCCACTTAAAGCAATCTCTGTCTTG 3'

Probe:
                                                 (SEQ ID NO: 74)
5' TCGACTCTTTGCCCACCGCCA 3'

Sense expanded pre-mRNA:
Forward:
                                                 (SEQ ID NO: 69)
5' ACTACTTGCTCTCACAGTACTCG 3'

Reverse:
                                                 (SEQ ID NO: 70)
5' TAGCGCGCGACTCCTGAGTTCC 3'

Probe:
                                                 (SEQ ID NO: 71)
5' AGGGAAACAACCGCAGCCTGTAGCAAGCTC 3'.
```

-continued

Antisense expanded pre-mRNA:
Forward:

(SEQ ID NO: 81)

5'AGTCGCTAGAGGCGAAAGC3'

Reverse:

(SEQ ID NO: 82)

5'CGAGTGGGTGAGTGAGGAG3'

Probe:

(SEQ ID NO: 83)

5'AAGAGGCGCGGGTAGAAGCGGGGGC3'

The data show that ZFP-TF 75027 repressed the levels of total C9 mRNA, sense and antisense expansion-containing transcripts in hippocampus and cortex of C9-BAC animals relative to PBS-injected controls (FIG. 9, Panel D). (No selective repression could be observed with this animal model because the transgenic mice do not contain a WT human C9orf72 allele and the moue C9orf72 gene does not contain $G_4C_2$ repeats). No repression was observed with ZFP-TF 75114.

In addition, fluorescent in situ hybridization was used to measure the levels of sense and antisense RNA aggregates (foci) found in the hippocampus after ZFP-TF injections (FIG. 9, Panel E). Briefly, 10 μm sections were hybridized with fluorophore-labeled probes: 5'GGCCCCGGCCCCGGCCCC-Cy3 (SEQ ID NO:84) was used to measure sense RNA foci and 5'GGGGCCGGGGCCGGGGCC-Cy3 (SEQ ID NO:85) was used to measure antisense RNA foci. Stack images were obtained on the confocal microscope (LSM880) at 40× zoom. The number of sense and antisense RNA foci normalized to the total number of cells were quantified from the cornu ammonis (CA) region of the hippocampus. Lower percentages of antisense RNA foci were observed in ZFP-TF 75027 injected animals.

These results show that a ZFP-TF targeting C9orf72 can effectively repress the expression of a disease-causing C9orf72 allele in vivo and that differences in the potencies of ZFP-TFs can be observed.

What is claimed is:

1. A fusion protein comprising a zinc finger protein (ZFP) DNA-binding domain and a transcription repressor domain, wherein the ZFP DNA-binding domain binds to a target site in a human C9orf72 gene, wherein the ZFP DNA-binding domain comprises six fingers (F) respectively comprising the recognition helix regions shown in a single row of the table below, wherein the SEQ ID NO of each sequence is indicated in parenthesis:

| F1 | F2 | F3 | F4 | F5 | F6 |
|---|---|---|---|---|---|
| DRSDLSR (27) | RSTHLVR (28) | DRSDLSR (27) | RSTHLVR (28) | DRSDLSR (27) | RSTHLVR (28) |
| DRSDLSR (27) | RSAHLSR (29) | DRSDLSR (27) | RSAHLSR (29) | DRSDLSR (27) | RSAHLSR (29) |
| ERGDLKR (30) | RSAHLSR (29) | ERGDLKR (30) | RSAHLSR (29) | ERGDLKR (30) | RSAHLSR (29) |
| ERGTLAR (31) | RSAHLSR (29) | ERGTLAR (31) | RSAHLSR (29) | ERGTLAR (31) | RSAHLSR (29) |
| RSADLSE (32) | RSAHLSR (29) | RSADLSE (32) | RSAHLSR (29) | RSADLSE (32) | RSAHLSR (29) |
| RSDHLSE (33) | DRSHLAR (34) | RSDHLSE (33) | DRSHLAR (34) | RSDHLSE (33) | DRSHLAR (34) |
| RSDHLSQ (35) | DNSHRTR (36) | RSDHLSQ (35) | DNSHRTR (36) | RSDHLSQ (35) | DNSHRTR (36) |
| RNGHLLD (37) | DRSHLAR (34) | RNGHLLD (37) | DRSHLAR (34) | RNGHLLD (37) | DRSHLAR (34) |
| RNGHLLD (37) | DNSHRTR (36) | RNGHLLD (37) | DNSHRTR (36) | RNGHLLD (37) | DNSHRTR (36) |
| RSAHLSE (38) | DNSHRTR (36) | RSAHLSE (38) | DNSHRTR (36) | RSAHLSE (38) | DNSHRTR (36) |
| RSAHLSR (29) | DRSDLSR (27) | RSAHLSR (29) | DRSDLSR (27) | RSAHLSR (29) | DRSDLSR (27) |
| RSDHLSR (39) | DWTTRRR (40) | RSDHLSR (39) | DWTTRRR (40) | RSDHLSR (39) | DWTTRRR (40) |
| RSAHLSR (29) | HRKSLSR (41) | RSAHLSR (29) | HRKSLSR (41) | RSAHLSR (29) | HRKSLSR (41) |
| RSAHLSR (29) | DSSDRKK (42) | RSAHLSR (29) | DSSDRKK (42) | RSAHLSR (29) | DSSDRKK (42) |
| RSAHLSR (29) | DSSTRRR (43) | RSAHLSR (29) | DSSTRRR (43) | RSAHLSR (29) | DSSTRRR (43) |
| RSAHLSR (29) | RSDDRKT (44) | RSAHLSR (29) | RSDDRKT (44) | RSAHLSR (29) | RSDDRKT (44) |
| RSAHLSR (29) | RSADRKT (45) | RSAHLSR (29) | RSADRKT (45) | RSAHLSR (29) | RSADRKT (45) |
| RSAHLSR (29) | RNADRIT (46) | RSAHLSR (29) | RNADRIT (46) | RSAHLSR (29) | RNADRIT (46) |
| RSAHLSR (29) | RRATLLD (47) | RSAHLSR (29) | RRATLLD (47) | RSAHLSR (29) | RRATLLD (47) |

-continued

| F1 | F2 | F3 | F4 | F5 | F6 |
|---|---|---|---|---|---|
| RSDTLSV (48) | DTSTRTK (49) | RSDTLSV (48) | DTSTRTK (49) | RSDTLSV (48) | DTSTRTK (49) |
| RNADRIT (46) | HRKSLSR (41) | RNADRIT (46) | HRKSLSR (41) | RNADRIT (46) | RNADRIT (46) |
| RSADRKT (45) | HRKSLSR (41) | RSADRKT (45) | HRKSLSR (41) | RSADRKT (45) | HRKSLSR (41) |
| RSATLSE (50) | HRKSLSR (41) | RSATLSE (50) | HRKSLSR (41) | RSATLSE (50) | HRKSLSR (41) |
| RSADRKT (45) | DSSTRRR (43) | RSADRKT (45) | DSSTRRR (43) | RSADRKT (45) | DSSTRRR (43) |
| RSADLSE (32) | HHRSLHR (51) | RSADLSE (32) | HHRSLHR (51) | RSADLSE (32) | HHRSLHR (51) |
| RSDHLSE (33) | TSSDRTK (52) | RSDHLSE (33) | TSSDRTK (52) | RSDHLSE (33) | TSSDRTK (52) |
| DRSHLTR (53) | DSSTRKT (54) | DRSHLTR (53) | DSSTRKT (54) | DRSHLTR (53) | DSSTRKT (54) |
| DKRDLAR (55) | RSADRKT (45) | DKRDLAR (55) | RSADRKT (45) | DKRDLAR (55) | RSADRKT (45) |
| ERGTLAR (31) | RSADRKT (45) | ERGTLAR (31) | RSADRKT (45) | ERGTLAR (31) | RSADRKT (45) |
| ERRDLRR (77) | RSADRKT (45) | ERRDLRR (77) | RSADRKT (45) | ERRDLRR (77) | RSADRKT (45) |
| RSDHLSE (33) | SSRYRTK (56) | RSDHLSE (33) | SSRYRTK (56) | RSDHLSE (33) | SSRYRTK (56) |
| REQDLKQ (57) | HRKSLSR (41) | REQDLKQ (57) | HRKSLSR (41) | REQDLKQ (57) | HRKSLSR (41) |
| RNADRIT (46) | HRKSLSR (41) | RNADRIT (46) | HRKSLSR (41) | RNADRIT (46) | HRKSLSR (41) |

2. The fusion protein of claim 1, wherein the fusion protein represses transcription of repeat-containing mRNA from the mutant allele and does not repress transcription of wildtype mRNA from the gene.

3. The fusion protein of claim 1, wherein the ZFP domain binds to a sense sequence in the target region, wherein the sense sequence comprises one to three tandem repeats of hexanucleotide GGGGCC (SEQ ID NO:1), GGGCCG (SEQ ID NO:2), GGCCGG (SEQ ID NO:3), GCCGGG (SEQ ID NO:4), CCGGGG (SEQ ID NO:5), or CGGGGC (SEQ ID NO:6).

4. The fusion protein of claim 1, wherein the fusion protein represses sense transcription from the mutant C9orf72 allele in a human cell.

5. The fusion protein of claim 4, wherein the fusion protein represses sense transcription from the C9orf72 1a promoter and does not repress sense transcription from the C9orf72 1b promoter.

6. The fusion protein of claim 1, wherein the ZFP domain binds to an antisense sequence in the target region, wherein the antisense sequence comprises one to three tandem repeats of hexanucleotide GGCCCC (SEQ ID NO:7), GCCCCG (SEQ ID NO:8), CCCCGG (SEQ ID NO:9), CCGGGC (SEQ ID NO:10), CCGGCC (SEQ ID NO:11), or CGGCCC (SEQ ID NO:12).

7. The fusion protein of claim 1, wherein the fusion protein represses antisense transcription from the mutant C9orf72 allele in a human cell.

8. The fusion protein of claim 1, wherein the fusion protein represses both sense transcription and antisense transcription from the mutant C9orf72 allele in a human cell.

9. The fusion protein of claim 1, wherein the fusion protein represses sense and/or antisense transcription from the mutant C9orf72 allele by at least about 30%, 40%, 75%, 90%, or 95%, optionally wherein the fusion protein does not repress sense transcription from the C9orf72 1b promoter.

10. The fusion protein of claim 1, wherein the transcription repressor domain comprises a KRAB domain amino acid sequence from human KOX1.

11. The fusion protein of claim 1, wherein the ZFP domain is linked to the transcription repressor domain through a peptide linker.

12. The fusion protein of claim 1, wherein the ZFP DNA-binding domain comprises the following F1 to F6 recognition helix regions and phosphate contact mutation(s):
DRSHLTR (SEQ ID NO:53), DSSTRKT (SEQ ID NO:54), DRSHLTR (SEQ ID NO:53), DSSTRKT (SEQ ID NO:54), DRSHLTR (SEQ ID NO:53), and DSSTRKT (SEQ ID NO:54), for F1 to F6, respectively, and an R-to-Q substitution at the −5 position of F1;
DKRDLAR (SEQ ID NO:55), RSADRKT (SEQ ID NO:45), DKRDLAR (SEQ ID NO:55), RSADRKT (SEQ ID NO:45), DKRDLAR (SEQ ID NO:55), and RSADRKT (SEQ ID NO:45), for F1 to F6, respectively, and an R-to-Q substitution at the −5 position of F1;
ERRDLRR (SEQ ID NO:77), RSADRKT (SEQ ID NO:45), ERRDLRR (SEQ ID NO:77), RSADRKT (SEQ ID NO:45), ERRDLRR (SEQ ID NO:77), and RSADRKT (SEQ ID NO:45), for F1 to F6, respectively, and an R-to-Q substitution at the −5 position of F1;
RSDHLSE (SEQ ID NO:33), DRSHLAR (SEQ ID NO:34), RSDHLSE (SEQ ID NO:33), DRSHLAR (SEQ ID NO:34), RSDHLSE (SEQ ID NO:33), and DRSHLAR (SEQ ID NO:34), for F1 to F6, respectively, and an R-to-Q substitution at the −5 position of F2, F3, and F5;
RSDHLSE (SEQ ID NO:33), DRSHLAR (SEQ ID NO:34), RSDHLSE (SEQ ID NO:33), DRSHLAR (SEQ ID NO:34), RSDHLSE (SEQ ID NO:33), and DRSHLAR (SEQ ID NO:34), for F1 to F6, respectively, and an R-to-Q substitution at the −5 position of F1, F2, F3, and F5;
RSDHLSE (SEQ ID NO:33), DRSHLAR (SEQ ID NO:34), RSDHLSE (SEQ ID NO:33), DRSHLAR (SEQ ID NO:34), RSDHLSE (SEQ ID NO:33), and DRSHLAR (SEQ ID NO:34), for F1 to F6, respectively, and an R-to-Q substitution at the −5 position of F1, F3, F4, and F6;
RSAHLSR (SEQ ID NO:29), HRKSLSR (SEQ ID NO:41), RSAHLSR (SEQ ID NO:29), HRKSLSR (SEQ ID NO:41), RSAHLSR (SEQ ID NO:29), and HRKSLSR (SEQ ID NO:41), for F1 to F6, respectively, and an R-to-Q substitution at the −5 position of F1 and F3;
RSAHLSR (SEQ ID NO:29), HRKSLSR (SEQ ID NO:41), RSAHLSR (SEQ ID NO:29), HRKSLSR (SEQ ID NO:41), RSAHLSR (SEQ ID NO:29), and HRKSLSR (SEQ ID NO:41), for F1 to F6, respectively, and an R-to-Q substitution at the −5 position of F3 and F5;
RSAHLSR (SEQ ID NO:29), HRKSLSR (SEQ ID NO:41), RSAHLSR (SEQ ID NO:29), HRKSLSR (SEQ ID NO:41), RSAHLSR (SEQ ID NO:29), and HRKSLSR (SEQ ID NO:41), for F1 to F6, respectively, and an R-to-Q substitution at the −5 position of F3 and F6;

RSAHLSR (SEQ ID NO:29), HRKSLSR (SEQ ID NO:41), RSAHLSR (SEQ ID NO:29), HRKSLSR (SEQ ID NO:41), RSAHLSR (SEQ ID NO:29), and HRKSLSR (SEQ ID NO:41), for F1 to F6, respectively, and an R-to-Q substitution at the −5 position of F2, F3, and F5;

RSAHLSR (SEQ ID NO:29), HRKSLSR (SEQ ID NO:41), RSAHLSR (SEQ ID NO:29), HRKSLSR (SEQ ID NO:41), RSAHLSR (SEQ ID NO:29), and HRKSLSR (SEQ ID NO:41), for F1 to F6, respectively, and an R-to-Q substitution at the −5 position of F2, F4, and F6;

REQDLKQ (SEQ ID NO:57), HRKSLSR (SEQ ID NO:41), REQDLKQ (SEQ ID NO:57), HRKSLSR (SEQ ID NO:41), REQDLKQ (SEQ ID NO:57), and HRKSLSR (SEQ ID NO:41), for F1 to F6, respectively, and an R-to-Q substitution at the −5 position of F1, F2, F3, and F4;

REQDLKQ (SEQ ID NO:57), HRKSLSR (SEQ ID NO:41), REQDLKQ (SEQ ID NO:57), HRKSLSR (SEQ ID NO:41), REQDLKQ (SEQ ID NO:57), and HRKSLSR (SEQ ID NO:41), for F1 to F6, respectively, and an R-to-Q substitution at the −5 position of F2 and F4; or RNADRIT (SEQ ID NO:46), HRKSLSR (SEQ ID NO:41), RNADRIT (SEQ ID NO:46), HRKSLSR (SEQ ID NO:41), RNADRIT (SEQ ID NO:46), and HRKSLSR (SEQ ID NO:41), for F1 to F6, respectively, and an R-to-Q substitution at the −5 position of F1, F2, F3, and F5.

13. The fusion protein of claim 1, wherein the ZFP DNA-binding domain comprises six fingers (F) respectively comprising SEQ ID NOs: 33, 34, 33, 34, 33, and 34.

14. The fusion protein of claim 1, wherein the ZFP DNA-binding domain comprises six fingers (F) respectively comprising SEQ ID NOs: 29, 41, 29, 41, 29, and 41.

15. The fusion protein of claim 1, wherein the ZFP DNA-binding domain comprises six fingers (F) respectively comprising SEQ ID NOs: 46, 41, 46, 41, and 46, and 46.

16. The fusion protein of claim 1, wherein the ZFP DNA-binding domain comprises six fingers (F) respectively comprising SEQ ID NOs: 53, 54, 53, 54, 53, and 54.

17. The fusion protein of claim 1, wherein the ZFP DNA-binding domain comprises six fingers (F) respectively comprising SEQ ID NOs: 55, 45, 55, 45, 55, and 45.

18. The fusion protein of claim 1, wherein the ZFP DNA-binding domain comprises six fingers (F) respectively comprising SEQ ID NOs: 77, 45, 77, 45, 77, and 45.

19. The fusion protein of claim 1, wherein the ZFP DNA-binding domain comprises six fingers (F) respectively comprising SEQ ID NOs: 33, 56, 33, 56, 33, and 56.

20. The fusion protein of claim 1, wherein the ZFP DNA-binding domain comprises six fingers (F) respectively comprising SEQ ID NOs: 57, 41, 57, 41, 57, and 41.

21. The fusion protein of claim 1, wherein the ZFP DNA-binding domain comprises six fingers (F) respectively comprising SEQ ID NOs: 46, 41, 46, 41, 46, and 41.

* * * * *